US008785400B2

(12) United States Patent
Levetan et al.

(10) Patent No.: US 8,785,400 B2
(45) Date of Patent: *Jul. 22, 2014

(54) METHODS AND COMPOSITIONS RELATING TO ISLET CELL NEOGENESIS

(75) Inventors: Claresa S. Levetan, Rosemont, PA (US); Loraine V. Upham, Albuquerque, NM (US)

(73) Assignee: CureDM Group Holdings, LLC, Wilmington, DE (US)

( * ) Notice: Subject to any disclaimer, the term of this patent is extended or adjusted under 35 U.S.C. 154(b) by 1157 days.

This patent is subject to a terminal disclaimer.

(21) Appl. No.: 11/943,991

(22) Filed: Nov. 21, 2007

(65) Prior Publication Data

US 2009/0068145 A1 Mar. 12, 2009

Related U.S. Application Data

(60) Provisional application No. 60/867,005, filed on Nov. 22, 2006.

(51) Int. Cl.
A61K 38/10 (2006.01)
A61K 38/00 (2006.01)

(52) U.S. Cl.
USPC .............................. 514/21.5; 514/6.8; 514/6.9

(58) Field of Classification Search
None
See application file for complete search history.

(56) References Cited

U.S. PATENT DOCUMENTS

| | | | |
|---|---|---|---|
| 4,444,887 A | 4/1984 | Hoffmann | |
| 4,716,111 A | 12/1987 | Osband et al. | |
| 4,816,397 A | 3/1989 | Boss et al. | |
| 4,816,567 A | 3/1989 | Cabilly et al. | |
| 5,223,409 A | 6/1993 | Ladner et al. | |
| 5,225,539 A | 7/1993 | Winter | |
| 5,403,484 A | 4/1995 | Ladner et al. | |
| 5,427,908 A | 6/1995 | Dower et al. | |
| 5,436,169 A | 7/1995 | Iovanna et al. | |
| 5,516,637 A | 5/1996 | Huang et al. | |
| 5,530,101 A | 6/1996 | Queen et al. | |
| 5,565,332 A | 10/1996 | Hoogenboom et al. | |
| 5,571,698 A | 11/1996 | Ladner et al. | |
| 5,580,717 A | 12/1996 | Dower et al. | |
| 5,580,859 A | 12/1996 | Felgner et al. | |
| 5,585,089 A | 12/1996 | Queen et al. | |
| 5,631,224 A | 5/1997 | Efendic et al. | |
| 5,658,727 A | 8/1997 | Barbas et al. | |
| 5,698,426 A | 12/1997 | Huse | |
| 5,733,743 A | 3/1998 | Johnson et al. | |
| 5,750,753 A | 5/1998 | Kimae et al. | |
| 5,766,886 A | 6/1998 | Studnicka et al. | |
| 5,780,225 A | 7/1998 | Wigler et al. | |
| 5,807,715 A | 9/1998 | Morrison et al. | |
| 5,821,047 A | 10/1998 | Garrard et al. | |
| 5,834,590 A | 11/1998 | Vinik et al. | |
| 5,840,531 A | 11/1998 | Vinik et al. | |
| 5,959,086 A | 9/1999 | Iovanna et al. | |
| 5,969,108 A | 10/1999 | McCafferty | |
| 6,311,415 B1 | 11/2001 | Lind | |
| 6,407,213 B1 | 6/2002 | Carter et al. | |
| 6,645,934 B1 | 11/2003 | Rodemann et al. | |
| 6,946,151 B2 | 9/2005 | Chatterji | |
| RE39,062 E | 4/2006 | Vinik et al. | |
| RE39,299 E | 9/2006 | Vinik et al. | |
| 7,166,439 B2 | 1/2007 | Vinik et al. | |
| 7,393,919 B2 | 7/2008 | Levetan et al. | |
| 7,576,121 B2 * | 8/2009 | Campbell et al. | 514/422 |
| 2003/0035803 A1 * | 2/2003 | McMichael | 424/146.1 |
| 2003/0212000 A1 | 11/2003 | Van Antwerp | |
| 2004/0132644 A1 | 7/2004 | Vinik et al. | |
| 2005/0084449 A1 | 4/2005 | Landes et al. | |
| 2006/0198839 A1 * | 9/2006 | Levetan | 424/130.1 |
| 2007/0087971 A1 | 4/2007 | Levetan et al. | |
| 2007/0184504 A1 | 8/2007 | Vinik et al. | |
| 2008/0300190 A1 | 12/2008 | Levetan et al. | |
| 2009/0142338 A1 * | 6/2009 | Levetan | 424/133.1 |
| 2010/0093605 A1 | 4/2010 | Levetan et al. | |

FOREIGN PATENT DOCUMENTS

| | | |
|---|---|---|
| EP | 0303233 A2 | 2/1989 |
| EP | 239400 | 8/1994 |
| EP | 1329458 A | 12/2000 |
| EP | 0592106 | 11/2004 |
| EP | 0519596 | 2/2005 |
| WO | WO 90/02809 | 3/1990 |
| WO | WO 91/09967 | 7/1991 |
| WO | WO 91/10737 | 7/1991 |
| WO | WO 91/10741 | 7/1991 |
| WO | WO 91/16428 A1 | 10/1991 |
| WO | WO 92/01047 | 1/1992 |
| WO | WO 92/18619 | 10/1992 |
| WO | WO 92/22324 | 12/1992 |
| WO | WO 93/11236 | 6/1993 |
| WO | WO 9317105 | 9/1993 |
| WO | WO 95/15982 | 6/1995 |

(Continued)

OTHER PUBLICATIONS

Wang et al. 2000. Genomics. 66:333-6.*
de Pril et al. 2007. Mol and Cell. Neuroscience 34:10-19.*
Rosenberg 2000. Current Gastroenterology Reports. 2:165-172.*
Hao et al., Beta-cell differentiation from nonendocrine epithelial cells of the adult human pancreas, 2006, Nature Medicine 12(3):310-316.
Levetan et al., Reduced Glucose Fluctuations Following 4 Weeks of Pramlintide Treatment in Patients with Type 1 Diabetes Intensively Treated with Insulin Pumps, 2002, Diabetes 51(suppl. 2):429-P.
Want et al., Reduced Postprandial Glucose, Glucagon and Triglyceride Excursions Following 4 Weeks of Pramlintide Treatment in Patients with Type 1 Diabetes Treated Intensively with Insulin Pumps, 2002, Diabetes 51(suppl. 2):474-P.

(Continued)

Primary Examiner — Shulamith H Shafer
(74) Attorney, Agent, or Firm — Pepper Hamilton LLP

(57) ABSTRACT

The present invention provides methods and kits for treating diseases and conditions associated with impaired pancreatic function. The present invention further provides methods of stimulating islet cell neogenesis and stimulating islet cell differentiation from progenitor cells.

16 Claims, 11 Drawing Sheets
(11 of 11 Drawing Sheet(s) Filed in Color)

(56) References Cited

FOREIGN PATENT DOCUMENTS

| | | |
|---|---|---|
| WO | WO 95/20401 | 8/1995 |
| WO | WO 96/19236 A1 | 6/1996 |
| WO | WO 96/26215 A | 8/1996 |
| WO | WO 96/33735 | 10/1996 |
| WO | WO 96/34096 | 10/1996 |
| WO | WO 97/13844 | 4/1997 |
| WO | WO 98/16654 | 4/1998 |
| WO | WO 98/24893 | 6/1998 |
| WO | WO 98/46645 | 10/1998 |
| WO | WO 98/50433 | 11/1998 |
| WO | WO 03/033808 A2 | 4/2003 |
| WO | WO 03/105897 A1 | 12/2003 |
| WO | WO 2006/096565 A | 9/2006 |
| WO | WO 2006/128083 A2 | 9/2006 |

OTHER PUBLICATIONS

Levetan et al., Impact of Pramlintide on the Amplitude of Glycemic Excursions, 2001, Diabetes 50(suppl. 2):2105-PO.

Levetan et al., Impact of Pramlintide on Glucose Fluctuations and Postprandial Glucose, Glucagon, and Triglyceride Excursions Among Patients with Type 1 Diabetes Intensively Treated with Insulin Pumps, 2003, Diabetes Care 26(1):1-8.

Herold et al., Anti-CD3 Monoclonal Antibody in New-Onset Type 1 Diabetes Melitus, May 30, 2002, NEJM 346(22):1692-1698.

Rosenberg et al., Trophic Stimulation of the Ductular-Islet Cell Axis: A New Approach to the Treatment of Diabetes, 1992, Adv. Exp. Med. Biol. 321:95-104.

Rosenberg et al., Islet-cell regeneration in the diabetic hamster pancreas with restoration of normoglycaemia can be induced by a local growth factor(s) Mar. 1996, Diabetologia 39(3):256-262.

Rosenberg et al., Induction of Islet Cell Differentiation and New Islet Formation in the Hamster-Further Support for a Ductular Origin, Jul. 1996, Pancreas 13(1):38-46.

Rosenberg et al., A Pentadecapeptide Fragment of Islet Neogenesis-Associated Protein Increases Beta-Cell Mass and Reverses Diabetes in C57BL/6J Mice, Nov. 2004, Ann. Surg. 240(5):875-884.

Vinik et al., Induction of Pancreatic Islet Neogenesis, Jun. 1997, Horm. Metab. Res. 29(6):278-293.

Young et al., Amylin's physiology and its role in diabetes, 1997, Curr. Opin. Endocrin. Diabetes 4(4):282-290.

Marquez et al., Inositolphosphoglycans Possibly Mediate the effects of Glucagon-Like Peptide-1(7-36)amide on Rat Liver and Adipose Tissue, 1998, Cell Biochem. Funct. 16(1):51-56.

Dupre et al., Exendin-4 Normalized Postcibal Glycemic Excursions in Type 1 Diabetes, 2004, J. Clin. Endocrin. Metab. 89(7):3469-3473.

Edwards et al., Glucagon-Like Peptide 1 Has a Physiological Role in the Control of Postprandial Glucose in Humans, 1999, Diabetes 48:86-93.

Xu et al., Exendin-4 Stimulates Both β-Cell Replication and Neogenesis, Resulting in Increased β-Cell Mass and Improved Glucose Tolerance in Diabetic Rats, 1999, Diabetes 48:2270-2276.

Andersen et al., Oral Glucose Augmentation of Insulin Secretion, 1978, J. Clin. Invest. 62:152-161.

Creutzfeldt et al., Inhibition of Gastric Inhibitory Polypeptide (GIP) Release by Insulin and Glucose in Juvenile Diabetes, 1980, Diabetes 29(2):140-145.

Dupre et al., Stimulation of Insulin Secretion by Gastric Inhibitory Polypeptide, 1973, J. Clin. Endocrin. Metab. 37:826-828.

Ebert et al., Gastric Inhibitory Polypeptide, 1980, Clin. in Gastroenterology 9(3):679-698.

Elahi et al., Pancreatic α-and β-cell responses to GIP infusion in normal man, 1979, Am. J. Physiol. 237:E185-E191.

Krarup et al., Diminished Immumoreactive Gastric Inhibitory Polypeptide Response to a Meal in Newly Diagnosed Type 1 (Insulin-Dependent) Diabetics, Jun. 1983, J. Clin. Endocrin. Metab. 56(6):1306-1312.

Krarup et al., Effect of Porcine Gastric Inhibitory Polypeptide on β-cell Function in Type I and Type II Diabetes Mellitus, 1987, Metabolism 36(7):677-682.

Krarup et al., Gastric Inhibitory Polypeptide in Newly Diagnosed Ketotic Type 1 (Insulin-dependent) Diabetics, 1988, Acta Med. Scand. 223(5):437-441.

Lynn et al., A novel pathway for regulation of glucose-dependent insulinotropic polypeptide (GIP) receptor expression in β cells, 2003, FASEB 17:91-93.

Meir et al., Gastric Inhibitory Polypeptide: the neglected incretin revisited, 2002, Regulatory Peptides 107:1-13.

Nauck et al., Additive Insulinotropic Effects of Exogenous Synthetic Human Gastric Inhibitory Polypeptide and Glucagon-Like Peptide-1-(7-36) Amide Infused at Near-Physiological Insulinotropic Hormone and Glucose Concentrations, 1993, J. Clin. Endocrin. Metab. 76(4):912-917.

Jones et al., A supplementary infusion of glucose-dependent insulinotropic polypeptide (GIP) with a meal does not significantly improve the β cell response or glucose tolerance in type 2 diabetes mellitus, Nov. 6, 1989, Diabetes Res. Clin. Prect. 7(4):263-269.

Elahi et al., The insulinotropic actions of glucose-dependent insulinotropic polypeptide (GIP) and glucagon-like peptide-1 (7-37) in normal and diabetic subjects, 1994, Regulatory Peptides 51(1):63-74.

Gutniak et al., Subcutaneous Injection of the Incretin Hormone Glucagon-Like Peptide 1 Abolishes Postprandial Glycemia in NIDDM, 1994, Diabetes Care 17(9):1039-1044.

Kreymann et al., Glucagon-Like Peptide-1 7-36: A Physiological Incretin in Man, 1987, Lancet 2:1300-1304.

Larsen et al., One-Week Continuous Infusion of GLP-1(7-37) Improves the Glycaemic Control in NIDDM, 1996, Diabetes 45(Suppl. 2):233A (860) (Abstract).

Larsen et al., Glucagon-Like Peptide-1 Infusion Must be Maintained for 24h/day to Obtain Acceptable Glycemia in Type 2 Diabetic Patients Who Are Poorly Controlled on Sulphonylurea Treatment, 2001, Diabetes Care 24(8):1416-1421.

List et al., Glucagon-like peptide 1 agonists and the development and growth of pancreatic β-cells, 2004, Am. J. Physiol. Endocrin. Metab. 286(6): E875-E881.

Lugari et al., Effect of Nutrient Ingestion on Glucagon-Like Peptide 1 (7-36 Amide) Secretion in Human Type 1 and Type 2 Diabetes, 2000, Horm. Metab. Res. 32:424-428.

Meier et al., Intravenous glucagon-like peptide 1 normalizes blood glucose after surgery inpatients with type 2 diabetes, Mar. 2004, Critical Care Medicine 32(3):848-851.

Meneilly et al., Effects of 3 Months of Continuous Subcutaneous Administration of Glucagon-Like Peptide 1 in Elderly Patients with Type 2 Diabetes, 2003, Diabetes Care 26(10):2835-2841.

Nauck et al., Effects of subcutaneous glucagon-like peptide 1 (GLP-1 [7-36]) in patients with NIDDM, 1996, Diabetologia 39(12):1546-1553.

Thorens et al., Glucagon-Like Peptide-1 and Control of Insulin Secretion, Dec. 1995, Diabetes Metab. 21(5):311-318.

Vilsboll et al., Incretion Secretion in Relation to Meal Size and Body Weight in Healthy Subjects and People with Type 1 and Type 2 Diabetes Mellitus, 2003, J. Clin. Endocrin. Metab. 88(6):2706-2713.

Wang et al., Glucagon-like peptide-1 Can Reverse the Age-related Decline in Glucose Tolerance in Rats, 1997, J. Clin. Invest. 99:2883-2889.

Zander et al., Effect of 6-week course of glucagon-like peptide 1 on glycaemic control, insulin sensitivity, and β-cell function in type 2 diabetes: a parallel-group study, 2002, Lancet 359:824-830.

Ausubel et al. eds., Current Protocols in Molecular Biology, John Wiley & Sons, 2008 (TOC).

Kriegler, Gene Transfer and Expression, A Laboratory Manual, Stockton Press, NY, 1990 (TOC).

Haines et al., eds., Current Protocols in Human Genetics, vol. 3, John Wiley & Sons, New York, 1994 Ch. 12: Vectors for Gene Therapy.

Haines et al., eds., Current Protocols in Human Genetics, vol. 4, John Wiley & Sons, New York, 1994 Ch. 13: Ex Vivo and in Vivo Gene Delivery to the Brain.

Colbere-Garapin et al., A New Dominant Hybrid Selective Marker for Higher Eukaryotic Cells, 1981, J. Mol. Biol. 150:1-14.

Merrifield, Solid Phase Peptide Synthesis, The Synthesis of a Tetrapeptide, 1963, J. Am. Chem. Soc. 85:2149-2154.

(56) References Cited

OTHER PUBLICATIONS

Bonner-Weir et al., The pancreatic ductal epithelium serves as a potential pool of progenitor cells, 2004, Pediatric Diabetes 5(Suppl 2):16-22.
Jamal et al., Morphogenetic plasticity of adult human pancreatic islets of Langerhans, Jul. 2005, Cell Death Differ. 12(7):702-712.
Rafaeloff et al., Cloning and Sequencing of the Pancreatic Islet Neogenesis Associated Protein (INGAP) Gene and Its Expression in Islet Neogenesis in Hamsters, J. Clin. Invest., May 1997, 99(9):2100-2109.
Lewis et al., Improved glucose control in nonhospitalized pregnant diabetic patients, 1976, Obstet. Gynecol. 48(3):260-267.
Ilic et al., Is the paradoxical first trimester drop in insulin requirement due to an increase in C-peptide concentration in pregnant Type I diabetic women? 2000, Diabetologia 43:1329-1330.
Jovanovic et al., Declining Insulin Requirement in the Late First Trimester of Diabetic Pregnancy, 2001, Diabetes Care 24:1130-1136.
Holick et al., Prevalence of Vitamin D Inadequacy among Postmenopausal North American Women Receiving Osteoporosis Therapy, 2005, J. Clin. Endocrinol. Metab. 90(6):3215-3224.
Riachy et al., 1,25-dihydroxyvitamin $D_3$ protects human pancreatic islets against cytokine-induced apoptosis via down-regulation of the fas receptor, Feb. 2006, Apoptosis 11(2):151-159.
Holick, High Prevalence of Vitamin D Inadequacy and Implications for Health, Mar. 2006, Mayo Clin. Proc. 81(3):353-373.
Grant, Epidemiology of disease risks in relation to vitamin D insufficiency, Feb. 28, 2006, Prog. Biophys. Mol. Biol. 92:65-79.
Dicesar et al., Vitamin D Deficiency is More Common in Type 2 Than in Type 1 Diabetes, Jan. 2006, Diabetes Care, 29(1):174.
Reis et al., Vitamin D endocrine system and the genetic susceptibility to diabetes, obesity and vascular disease: A review of evidence, 2005, Diabetes Metab. 31(4 pt 1):318-325.
Pozzilli et al., Low Levels of 25-hydroxyvitamin $D_3$ and 1,25-dihydroxyvitamin $D_3$ in Patients with Newly Diagnosed Type 1 Diabetes, 2005, Horm. Metab. Res. 37(11):680-683.
Heaney et al., Human serum 25-hydroxycholecalciferol response to extended oral dosing with cholecalciferol$^{1-3}$, 2003, Am. J. Clin. Nutr. 77:204-210.
Vieth et al., Efficacy and safety of vitamin $D_3$ intake exceeding the lowest observed adverse effect level $^{1-3}$, 2001, Am. J. Clin. Nutr. 73:288-294.
Yoon et al., Selective β-Cell Loss and α-Cell Expansion in Patients with Type 2 Diabetes Mellitus in Korea, 2003, J. Clin. Endocrinol. Metab. 88:2300-2308.
Li et al., Islet loss and alpha cell expansion in type 1 diabetes induced by multiple low-dose streptozotocin administration in mice, 2000, J. Endocrinol. 165:93-99.
Vukkadapu et al., Dynamic interaction between T cell-mediated β-cell damage and β-cell repair in the run up to autoimmune diabetes of the NOD mouse, Apr. 14, 2005, Physiol. Genomics, 21(2):201-211.
Ausubel et al. eds., Short Protocols in Molecular Biology, 2$^{nd}$ ed., A Compendium of Methods from Current Protocols in Molecular Biology, John Wiley & Sons, New York, 1992 (TOC).
Herold et al., A Single Course of Anti-CD3 Monoclonal Antibody hOKT3γ1 (Ala-Ala) Results in Improvement in C-Peptide Responses and Clinical Parameters for at Least 2 Years after Onset of Type 1 Diabetes, 2005, Diabetes 54(6):1763-1769.
Raz et al., β-cell function in new-onset type 1 diabetes and immunomodulation with a heat-shock protein peptide (DiaPep277): a randomized, double-blind, phase II trial, 2002, Lancet, 358:1749-1753.
Agardh et al., Clinical evidence for the safety of GAD65 immunomodulation in adult-onset autoimmune diabetes, 2005, J. Diabetes Complications, 19(4):238-246.
Creutzfeldt, The Incretin Concept Today, 1979, Diabetologia 16:75-85.
Holst et al., Incretin hormones-an update, 2001, Scand. J. Clin. Lab. Invest. Suppl. 234:75-85.
Bach et al., Tolerance to Islet Autoantigens in Type 1 Diabetes, Ann. Rev. Immun. 19:131-161.
Lernmark et al., Autoimmunity of Diabetes, Endocrin. Metab. Clin. N. Am. 20(3):589-617.
Mathis et al., β-Cell death during progression to diabetes, Dec. 2001, Nature 414(6865):792-798.
Davis et al., The effects of HDV-insulin on carbohydrate metabolism in Type 1 diabetic patients, 2001, J. Diabetes Comp. 15(5):227-233.
Hopp et al., Prediction of protein antigenic determinants from amino acid sequences, 1981, Proc. Natl. Acad. Sci. USA 78:3824-3828.
Harlow et al., Antibodies: A Laboratory Manual, Cold Spring Harbor Laboratory Press, 2$^{nd}$ ed., New York, 1988 (TOC).
Hammerling et al., Monoclonal Antibodies and T-Cell Hybridomas 563 681, Elsevier, New York, 1981 (TOC).
Brinkmann et al., Phage display of disulfide-stabilized Fv fragments, 1995, Immunol. Methods 182:41-50.
Ames et al., Conversion of murine Fabs isolated from a combinatorial phage display library to full length immunoglobulins, 1995, J. Immunol. Methods 184:177-186.
Kettleborough et al., Isolation of tumor cell-specific single-chain Fv from immunized mice using phage-antibody libraries and the reconstruction of whole antibodies from these antibody fragments, 1994, Eur. J. Immunol. 24:952-958.
Burton et al., Human Antibodies from Combinatorial libraries, 1994, Advances in Immunology 57:191-280.
Mullinax et al., Expression of a Heterodimeric Fab Antibody Protein in One Cloning Step 1992, BioTechniques 12(6):864-869.
Sawai et al., Direct Production of the Fab Fragment Derived from the Sperm Immobilizing Antibody Using Polymerase Chain Reaction and cDNA Expression Vectors, 1995, AJRI 34:26-34.
Better et al., *Escherichia coli* Secretion of an Active Chimeric Antibody Fragment, 1988, Science 240:1041-1043.
Morrison, Transfectomas Provide Novel Chimeric Antibodies, 1985, Science 229:1202-1207.
Oi et al., Chimeric Antibodies, 1986, BioTechniques 4(3):214-221.
Gillies et al., High-level expression of Chimeric antibodies using adapted cDNA variable region cassettes, 1989, J. Immunol. Methods 125:191-202.
Padlan, A Possible Procedure for Reducing the Immunogenicity of Antibody Variable Domains While Preserving Their Ligand-Binding Properties, 1991, Molecular Immunology 28(4/5):489-498.
Studnicka et al., Human-engineered monoclonal antibodies retain full specific binding activity by preserving non-CDR complementarity-modulating residues, 1994, Protein Engineering 7(6):805-814.
Roguska et al., Humanization of murine monoclonal antibodies through variable domain resurfacing, 1994, PNAS 91:969-973.
Tan et al., "Superhumanized" Antibodies: Reduction of Immunogenic Potential by Complementarity-Determining Region Grafting with Human Germline Sequence: Application to an Anti-CD28, 2002, J. Immunol. 169:1119-1125.
Caldas et al., Design and synthesis of germline-based hemi-humanized single-chain Fv against the CD18 surface antigen, 2000, Protein Eng. 13(5):353-360.
Morea et al., Antibody Modeling: Implications for Engineering and Design, 2000, Methods 20(3):267-279.
Baca et al., Antibody Humanization Using Monovalent Phage Display, 1997, J. Biol. Chem. 272(16):10678-10684.
Roguska et al., A comparison of two murine monoclonal antibodies humanized by CDR-grafting and cariable domain resurfacing, 1996, 9(10):895-904.
Couto et al., Designing Human Consensus Antibodies with Minimal Positional Templates, 1995, Cancer Res. 55 (23 Suppl):5973s-5977s.
Couto et al., Anti-BA46 Monoclonal Antibody Mc3: Humanization Using a Novel Positional Consensus and *in Vivo* and *in Vitro* Characterization, 1995, Cancer Res. 55(8):1717-1722.
Sandhu, A rapid procedure for the humanization of monoclonal antibodies, 1994, Gene 150(2):409-410.
Pederson et al., Comparison of Surface Accessible Residues in Human and Murine Immunoglobulin Fv Domains, 1994, J. Mol. Biol. 235(3):959-973.
Riechmann et al., Reshaping human antibodies for therapy, 1988, Nature 332(24):323-327.

(56) References Cited

OTHER PUBLICATIONS

Scopes, Protein Purification, Principles and Practice, 3rd ed., Springer-Verlag, New York, 1994 (TOC).
Wu et al., Adapters, Linkers, Methylation, 1987, Methods in Enzymol 152:343-349.
Foecking et al., Powerful and versatile enhancer-promoter unit for mammalian expression vectors, 1986, Gene 45:101-105.
Cockett et al., High Level Expression of Tissue Inhibitor of Metalloproteinases in Chinese Hamster Ovary Cells Using Glutamine Synthetase Gene Amplification, 1990, Bio/Technology 8:662-667.
Inouye et al., Up-promoter mutations in the *Ipp* gene of *Escherichia coli*, 1985, Nucleic Acids Res. 13:3101-3109.
Logan et al., Adenovirus tripartite leader sequence enhances translation of mRNAs late after infection, 1984, Proc. Natl. Acad. Sci. USA 81:3655-3659.
Bitter et al., Expression and Secretion Vectors for Yeast, 1987, Methods in Enzymol. 153:516-544.
Wu et al., Delivery systems for gene therapy, 1991, Biotherapy 3(1):87-95.
Tolstoshev, Gene Therapy, Concepts, Current Trials and Future Directions, 1993, Ann. Rev. Pharmacol. Toxicol. 32:573-596.
Mulligan, The Basic Science of Gene Therapy, 1993, Science 260:926-932.
Morgan et al., Human Gene Therapy, 1993, Ann. Rev. Biochem. 62:191-217.
Wigler et al., Transformation of mammalian cells with an amplifiable dominant-acting gene, 1980, Natl. Acad. Sci. USA 77(6):3567-3570.
Ohare et al., Transformation of mouse fibroblasts to methotrexate resistance by a recombinant plasmid expressing a prokaryotic dihydrofolate reductase, 1981, Proc. Natl. Acad. Sci. USA 78(3):1527-1531.
Mulligan et al., Selection for animal cells that express the *Escherichia coli* gene coding for xanthine-guanine phosphoribosyltransferase, 1981, Proc. Natl. Acad. Sci. USA 78(4):2072-2076.
Atherton et al., 1989, Solid Phase Peptide Synthesis: A Practical Approach, IRL Press, Oxford (TOC).
Bodanszky, 1993, Peptide Chemistry, A Practical Textbook, 2nd ed., Springer-Verlag, Berlin, (TOC).
Delovitch et al., The Nonobese Diabetic Mouse as a Model of Autoimmune Diabetes: Immune Dysregulation Gets the NOD, 1997, Immunity 7:727-738.
Van Heeke et al., Expression of Human Asparagine Synthetase in *Escherichia coli*, 1989, J. Biol. Chem. 24:5503-5509.
Rigg et al., Effects of Exogenous insulin on excursions and diurnal rhythm of plasma glucose in pregnant diabetic patients with and without residual, 1980, Am. J. Obstet. Gynecol. 136:537-544.
Buse et al., Amylin replacement with pramlintide in type 1 and type 2 diabetes: A physiological approach to overcome barriers with insulin therapy, 2002, Clin. Diab. 20:137-144.
Santerre et al., Expression of prokaryotic genes for hygromycin B and G418 resistance as dominant-selection markers in mouse L. cells, 1984, Gene 30:147-158.
Creutzfeldt, t al., New Developments in the Incretin Concept, 1985, Diabetologia 28:565-573.
Ogawa et al., Cure of Overt Diabetes in NOD Mice by Transient Treatment with Anti-Lymphocyte Setum and Exendin-4, 2004, Diabetes 53(7):1700-1705.
Persic et al., An integrated vector system for the eukaryotic expression of antibodies or their fragments after selection from phage display libraries, 1997, Gene 187:9-18.
Biron et al., A Monomeric 310-Helix is Formed in Water by a 13-Residue Peptide Representing the Neutralizing Determinant of HIV-1 on gp41, *Biochemistry* (2002) 41(42):12687-12696.
Casteels, et al., Prevention of Type I Diabetes in Nonobese Diabetic Mice by Late Intervention with Nonhypercalcemic Analogs of 1,25-Dihydroxyvitamin D3 in Combination with a Short Induction Course of Cyclosporin A, *Endocrionology* (1998) 139(1):95-102.
International Search Report and Written Opinion dated Dec. 23, 2008 (PCT/US2008/074868).
International Search Report and Written Opinion dated Feb. 26, 2007 (PCT/US2006/020644).
International Search Report and Written Opinion dated Aug. 22, 2008 (PCT/US2007/85378).
Levetan, et al., Reduced Postprandial Glucose, Glueagon and Triglyceride Excursions Following 4 Weeks of Pramlintide Treatment in Patients with Type 1 Diabetes Treated Intensively with Insulin Pumps, *Abstracts from 62nd Ann. Mtg. In San Francisco, CA, Diabetes* (Jun. 2002) 51(Sup. 2):474-P:A117 (Abstract).
Ludvigsson et al., GAD Treatment and Insulin Secretion in Recent-Onset Type 1 Diabetes, *N Engl J Med* (Oct. 30, 2008) 359(18):1909-1920.
Mishra, et al., Studies of Synthetic Peptides of Human Apolipoprotein A-I Containing Tandem Amphipathic α-Helixes, *Biochemistry* (1998) 37(28):10313-10324.
Rabinovitch, et al., Combination Therapy With Sirolimus and Interleukin-2 Prevents Spontaneous and Recurrent Autoimmune Diabetes in NOD Mice, *Diabetes* (2002) 51:638-645.
Tam, et al., INGAP Peptide improves nerve function and enhances regeneration in streptozotocin-induced diabetic C57BL/6 mice, *FASEB J.* (Sep. 2, 2004) 18(4):1-23.
Yamaoka, Regeneration therapy for diabetes mellitus, *Expert Opin. Biol. Ther* (2003) 3(3):425-433.

\* cited by examiner

|         | Total Islet Mass (μm2) | % increase |
|---------|------------------------|------------|
| Placebo | 854364                 |            |
| HIP 2   | 2161782                | 153%       |
| HIP     | 1703513                | 99%        |

|         | Total Islet # | % increase |
|---------|---------------|------------|
| Placebo | 280           |            |
| HIP 2   | 454           | 62%        |
| HIP     | 410           | 46%        |

I. Control

HIP2

METHODS AND COMPOSITIONS RELATING TO ISLET CELL NEOGENESIS

CROSS-REFERENCE TO RELATED APPLICATIONS

This application claims the benefit of U.S. Provisional Application Ser. No. 60/867,005, filed on Nov. 22, 2006, which is hereby incorporated by reference in its entirety.

GOVERNMENT INTERESTS

Not applicable

PARTIES TO A JOINT RESEARCH AGREEMENT

Not Applicable

INCORPORATION BY REFERENCE OF MATERIAL SUBMITTED ON A COMPACT DISC

Not applicable

BACKGROUND

1. Field of Invention
Not Applicable
2. Description of Related Art
Not Applicable

BRIEF SUMMARY OF THE INVENTION

Some embodiments of the present invention provide methods for stimulating islet cell neogenesis with the HIP2 peptide and pharmaceutical formulations containing the HIP2 peptide as well as related therapeutic methods for treating patients with diseases or disease conditions related to decreased pancreatic function. In one embodiment, the disease is type 1 diabetes, and in another, the disease is type 2 diabetes. In another embodiment, the patient has a condition associated with type 1 or type 2 diabetes. In various embodiments, the methods of the invention can be practiced by administration of a therapeutically effective amount of HIP2 alone, in combination with insulin, in combination with insulin and another agent, and in combination with one or more agents other than insulin.

As exemplified by the preceding paragraph, some embodiments of the present invention provide methods of stimulating islet cell neogenesis in a subject in need thereof, comprising administering to the subject a therapeutically effective amount of HIP2, or an analog or derivative thereof; and methods of stimulating islet cell neogenesis in a subject in need thereof, comprising administering to the subject a therapeutically effective amount of HIP2, or an analog or derivative thereof, and a therapeutically effective amount of an agent selected from the group consisting of: an immune therapy agent and an additional agent that stimulates islet cell regeneration. In some embodiments, the total islet number is increased. In some embodiments, the total islet number is increased by up to 50%. In some embodiments, the total islet number is increased by at least 50%. In some further embodiments, the total islet mass is increased. In some embodiments, the total islet mass is increased by up to 100%. In some embodiments, the total islet mass is increased by at least 100%.

Some embodiments of the present invention in part arise from the discovery that HIP2 is functionally more active, i.e., capable of exhibiting greater activity with respect to one or more of the functional activities associated with HIP or the hamster INGAP peptide.

Some embodiments of the present invention provide pharmaceutical formulations and unit dose forms of HIP2. In one embodiment, the pharmaceutical formulation provided contains HIP2 alone or in combination with one or more other active pharmaceutical ingredients (APIs) or agents in soluble liposome preparations that allow the HIP2 to be administered by a variety of routes, including subcutaneously, intramuscularly, intravenously, and even orally, depending on the formulation selected. In one embodiment, the formulation is for general systemic administration, but in other embodiments, the formulation comprises a targeting agent for targeted administration to specific locations, receptors, cells, tissues, organs, or organ systems within a subject.

Those of skill in the art will appreciate that the preceding paragraph exemplifies some embodiments of the invention providing pharmaceutical compositions comprising a therapeutically effective amount of HIP2 and one or more pharmaceutically acceptable excipients and/or adjuvants.

In other embodiments of the inventive method of treating a pathology associated with impaired pancreatic function in a subject in need of such treatment, the method further comprises the step of administering one or more agents for stimulating pancreatic islet cell regeneration in addition to HIP2. In one aspect of this embodiment, the agents are selected from a member of the group consisting of HIP or a HIP-related peptide other than HIP2, SYMLIN® (amylin/pramlintide), exendin-4, BYETTA® (exenatide), GIP, GLP-1, GLP-1 receptor agonists, GLP-1 analogs, hamster INGAP peptide and related peptides, Liraglutide (NN2211), and a dipeptidyl peptidase inhibitor, which blocks the degradation of GLP-1.

In another embodiment of the inventive method of treating a pathology associated with impaired pancreatic function in a subject in need of such treatment, the method further comprises one or more of the steps of (1) intensifying glycemic control; (2) administering oral vitamin D3 (cholecalciferol) to maintain 25-hydroxyvitamin levels above 40 ng/ml; (3) administering one or more immune therapies for protecting new islet cell formation, including administration of immunosuppressive agents; (4) administering HIP2 in combination with insulin but decreasing the insulin administered over time; and (5) repeatedly administering a therapy for protection of islets on a 3 to 24 month basis, depending on the selected immune therapy, in addition to the step of administering HIP2.

In another embodiment of the inventive method of treating a pathology associated with impaired pancreatic function in a subject in need of such treatment, the method further comprises one or more of the steps of: (1) intensifying glycemic control; (2) administering oral vitamin D3 (cholecalciferol) to maintain 25-hydroxyvitamin levels above 40 ng/ml; (3) administering an agent for stimulating pancreatic islet regeneration in addition to HIP2, including but not limited to HIP and HIP analogs other than HIP2; (4) co-administering an agent selected from the group consisting of SYMLIN® (amylin/pramlintide), exendin-4, BYETTA® (exenatide), Gastrin, Epidermal Growth Factor and Epidermal Growth Factor analog GIP, GLP-1, GLP-1 receptor agonists, GLP-1 analogs, INGAP, Liraglutide (NN2211), and a dipeptidyl peptidase IV inhibitor, which blocks the degradation of GLP-1; and (5) reducing, or tapering off, administration of another diabetes therapy.

In another embodiment of the inventive method of treating a pathology associated with impaired pancreatic function in a subject in need of such treatment, the method further comprises, in addition to administering HIP2, the step of administering one or more agents that inhibit, block, or destroy the autoimmune cells that target pancreatic islets. Such therapies are termed "immune therapies" above. In various aspects of this embodiment, the agents that inhibit, block, or destroy the autoimmune cells that target pancreatic islets are selected from the group consisting of Anti CD-3 antibodies (hOKT3γ1 (Ala-Ala) and ChAglyCD3) that target the immune response and specifically block the T-lymphocytes that cause beta cell death in type 1 diabetes; Sirolimus (Rapamycin); Tacrolimus (FK506); a heat-shock protein 60 (Diapep277); an anti-Glutamic Acid Decarboxylase 65 (GAD65) vaccine; Mycophenolate Mofetil alone or in combination with Daclizumab; the anti-CD20 agent, Rituximab; Campath-1H (Anti-CD52 Antibody), lysofylline; Vitamin D; IBC-VSO vaccine, which is a synthetic, metabolically inactive form of insulin designed to prevent pancreatic beta-cell destruction; interferon-alpha; and a vaccine using $CD4^+CD25^+$ antigen-specific regulatory T cells. In some embodiments, these or similar agents can be used in the combination therapies provided by the invention that utilize regulatory T cells either directly or through the use of immunotherapy to arrest the destruction of insulin-producing cells.

In another embodiment of the inventive method of treating a pathology associated with impaired pancreatic function in a subject in need of such treatment, at least one symptom of the pathology associated with impaired pancreatic function is treated or reduced as a result of the administration of HIP2. In one aspect of this embodiment, the symptom is selected from a member of the group consisting of low levels of insulin or insulin activity, insulin resistance, hyperglycemia, hemoglobin A1C level greater than 6.0%, frequent urination, excessive thirst, extreme hunger, unusual weight loss or gain, being overweight, increased fatigue, irritability, blurry vision, genital itching, odd aches and pains, dry mouth, dry or itchy skin, impotence, vaginal yeast infections, poor healing of cuts and scrapes, excessive or unusual infections, loss or worsening of glycemic control, fluctuations in blood glucose, fluctuations in blood glucagon, and fluctuations in blood triglycerides, with hyperglycemia ultimately leading to microvascular and macrovascular complications, which include visual symptoms that lead to blindness, accelerated kidney impairment that can lead to renal failure necessitating dialysis or kidney transplant and neuropathy leading to foot ulcers and amputations.

In another embodiment of the method of treating a pathology associated with impaired pancreatic function in a subject in need of such treatment, the pathology associated with impaired pancreatic function is any one of type 1 diabetes, new onset type 1 diabetes, type 2 diabetes, latent autoimmune diabetes of adulthood, pre-diabetes, impaired fasting glucose, impaired glucose tolerance, insulin resistant syndrome, metabolic syndrome/dysmetabolic syndrome, being overweight, obesity, hyperlipidemia, hypertriglyceridemia, eating disorders, anovulatory cycles and polycystic ovarian syndrome.

Some embodiments of the invention also provide an antibody which selectively binds to HIP2. In one embodiment, the antibody is a monoclonal antibody. In another embodiment, the antibody is a polyclonal antibody. In some embodiments, such antibodies can be used in diagnostic methods provided by the invention, which methods comprise detecting HIP2 levels in the serum or tissue of a mammal. In one embodiment, such methods are used to diagnose a disease or condition related to aberrant HIP2 levels. In another embodiment, the diagnostic method is used to monitor treatment with HIP2 to ensure that therapeutically effective levels are being achieved in a patient receiving such therapy.

Some embodiments of the invention also provide a kit for treating a patient having type 1 or type 2 diabetes or other condition in which there are aberrant insulin levels, perturbation in glucose metabolism or insulin resistance, comprising a therapeutically effective dose of HIP2 and optionally at least one agent for stimulating GLP-1 receptors or enhancing GLP-1 levels, promoting beta cell regeneration, increased satiety, decreased food intake and weight loss, either in the same or separate packaging, and instructions for its use. Further embodiments of the invention also provide a kit for measuring HIP2 levels in a sample, the kit comprising a HIP2-specific antibody and optionally HIP2 and optionally a labeling means.

These and other aspects and embodiments of the invention are described in greater detail below.

DESCRIPTION OF DRAWINGS

The file of this patent contains at least one drawing/photograph executed in color. Copies of this patent with color drawing(s)/photograph(s) will be provided by the Office upon request and payment of the necessary fee.

FIG. 10 is a table depicting the increased total islet number and increased total islet mass observed after treatment with HIP2.

DETAILED DESCRIPTION

Figure 1:
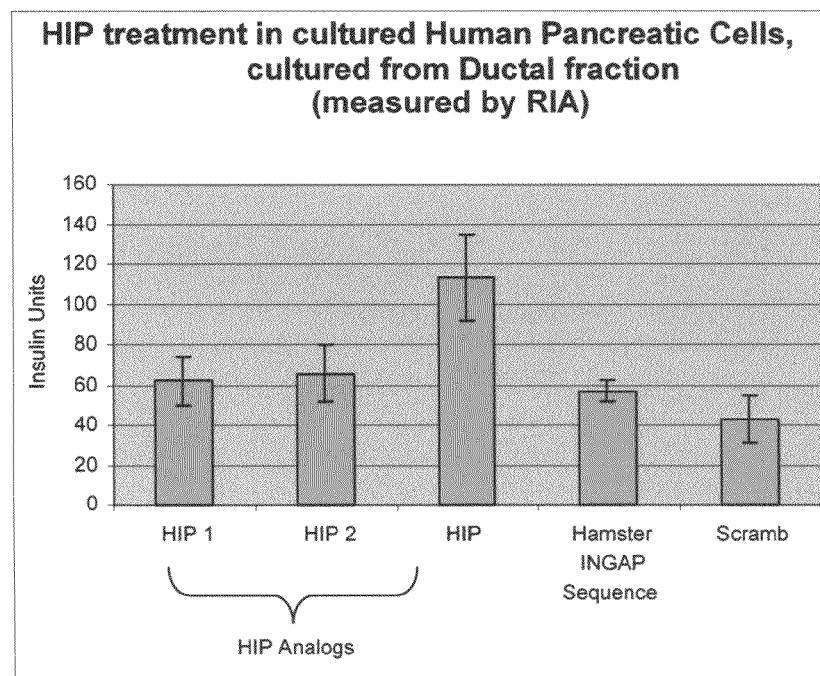
FIG. 1 is a bar graph showing increased insulin production in human pancreatic ductal tissue culture after treatment with HIP analogs, as compared with similar treatment with SEQ ID NO:1 and SEQ ID NO:2.

Insulin has been, since 1922, the primary if not the only available therapy for the treatment of type 1 diabetes and other conditions related to the lack of or diminished efficacy or production of insulin. However, diabetic patients on insulin do not have normal glucose metabolism, because insulin is only part of the missing and aberrant pancreatic function. Despite decades of research and the advent of pancreatic islet transplantation in 1974 and newer claims of success resulting from the Edmonton Protocol for islet transplantation, these approaches have not been very successful in the United States. For example, at four years post-transplant, fewer than 10% of patients who have received islet transplants remain insulin independent. Additionally, there is an 18% rate of serious side effects.

Investigators have also researched whether endogenous production of insulin can be stimulated by drug treatment. For example, over the past several decades, several therapies have been studied in which a peptide involved in glucose metabolism, or analogs of such peptides, have been administered to diabetic patients. These therapies include the administration of peptides with amino acid sequences similar to those of Glucagon Like Peptide-1 (GLP-1), and such peptides include: GLP-1 receptor analogs, Exendin-4, BYETTA® (exenatide), which is derived from the Gila Monster, JANUVIA® (sitagliptin), Gastric Inhibitory Peptide/Glucose-Dependent Insulinoptropic polypeptide (GIP), compounds homologous to GLP-1, such as Liraglutide (NN2211), Dipeptidyl Peptidase-4 Inhibitors, which inhibit the breakdown of GLP-1, Gastrin, Epidermal Growth Factor and Epidermal Growth Factor Analogs, and Hamster derived Islet Neogenesis Associated Peptide (INGAP).

In addition, hamster INGAP fragments have been identified that may be effective in facilitating pancreatic islet neogenesis. In particular, the hamster INGAP peptide identified as SEQ ID NO:1 has been identified as an agent beneficial for the stimulation of ductal cell proliferation in hamsters. However, INGAP is not a human protein, and thus proteins and peptides based on its sequence may not be as efficacious as human counterpart proteins and peptides and could even produce an adverse immune response in some subjects. U.S. Patent Application Publication No. 2003/0212000 describes a human Reg3a gene that appears to be the human counterpart of the hamster INGAP gene and identifies a 15-mer (hereinafter referred to as "HIP", a peptide of sequence identified as SEQ ID NO:2) peptide corresponding to the hamster INGAP peptide sequence but does not demonstrate that the gene product or peptide can stimulate islet cell neogenesis.

U.S. Patent Application Publication No. 20070087971A1, which is hereby incorporated herein by reference in its entirety, discloses methods for using HIP alone and in combination with other agents to stimulate islet cell neogenesis and treat various disease and disease conditions. In addition, this patent application discloses related compounds HIP1 (SEQ ID NO:3) and HIP2 (SEQ ID NO:4).

For any islet cell neogenesis agent to be effective, the pancreas must be "clastic" with respect to its ability to generate new islet cells. Proof of the elasticity of the pancreas with respect to the generation of new pancreatic islets throughout one's lifetime in response to pancreatic islet death or apoptosis has replaced the long held concept that the number of insulin producing islet structures is fixed at birth and maintained throughout life, whereas the plasticity and ability of beta cells to proliferate within existing islets has been well established. It is currently accepted that pancreatic islet neogenesis occurs from preexisting pancreatic cells through differentiation of progenitor cells found amongst both the endocrine and exocrine fractions of the pancreas. Data demonstrates that, even decades after the onset of type 1 diabetes, pancreatic islets can be regenerated.

For example, patients with type 1 diabetes are able to make normal levels of C-peptide during pregnancy. Several teams have found a paradoxical rise in C-peptide levels during the first trimester of pregnancy into the normal range in as many as one-third of all pregnant type 1. This rise in C-peptide is accompanied by a significant reduction in insulin requirements with some patients being able to discontinue insulin transiently during the first trimester of pregnancy. This rise in C-peptide during pregnancy that occurs within 10 weeks of gestation among patients, despite no measurable C-peptide prior to pregnancy, implies the restoration of functioning islet structures. It is hypothesized that the islet neogenesis that occurs during pregnancy results from the concomitant rise in endogenous steroid production and a down regulation of the immune system preventing immune attack on the fetus, which likely also plays a role in suppression of lymphocyte attack on the islets. Along with immune suppression, it is also speculated that there is an up regulation of maternal islet growth promoting factors during pregnancy to compensate for the lowering of the maternal glucose setpoint in pregnancy. Similarly, patients who have been on long term immunosuppression for kidney transplantation have been observed to regenerate insulin producing islets.

Over the past decade, clinical trials have been conducted to evaluate the impact of a number of immune modulators that may arrest the destruction of the beta cells of the pancreas. Anti CD-3 antibodies (hOKT3γ1 (Ala-Ala and ChAglyCD3) that target the immune response and specifically block the T-lymphocytes that cause beta cell death in type 1 diabetes have been utilized for this purpose, as have treatments involving the administration of Sirolimus (Rapamycin), Tacrolimus (FK506), DIAPEP277™ (a 24 amino acid fragment of heat shock protein 60), an anti-Glutamic Acid Decarboxylase 65 (GAD65) vaccine, Mycophenolate Mofetil alone or in combination with Daclizumab, the anti-CD20 agent, lysofylline, Rituximab, Campath-1H (Anti-CD52 Antibody), Vitamin D, IBC-VSO vaccine, which is a synthetic, metabolically inactive form of insulin designed to prevent pancreatic beta-cell destruction, and interferon-α vaccination using $CD4^+CD25^+$ antigen-specific regulatory T cells. These therapeutic approaches are intended to utilize regulatory T cells either directly or through the use of immunotherapy to arrest the destruction of insulin-producing cells. The aim of these trials is to determine the ability of such agents to preserve islet function by preventing further immune attack on the beta cells of the islets of the pancreas.

Additionally, recent studies have found that vitamin D may play an important immune modulating role in the prevention of type 1 diabetes. Up to 54.7% of populations in the US, regardless of latitude, have low 25 hydroxyvitamin D levels. Vitamin D deficiency has been demonstrated, not only to be associated with the increased risk of type 1 diabetes and seen at the onset of type 1 diagnosis, but also is commonly seen among both patients with type 1 and 2 diabetes. Maintaining levels above 40 ng/ml are recommended to sustain normal immune function. No adverse effects have been seen with doses up to 10,000 IU/day.

To date, however, there has been no therapy that has been successfully used to treat the underlying disease mechanisms of type 1 diabetes, type 2 diabetes or conditions in which there is a lack of or diminished insulin production and/or alterations in glucose metabolism or insulin secretion, including obesity, overweight, insulin resistant syndromes and the metabolic syndrome. There remains a need for new treatments, methods and pharmaceutical compositions that address the underlying mechanisms for the alterations in type 1 diabetes mellitus, type 2 diabetes mellitus and other conditions in which there is a decrease in insulin secretion or an increased need for insulin. Especially needed are methods and compositions that can also treat the many other conditions in which the lack of, or diminished, insulin production has a causative role or contributes to the symptoms of patients in need of treatment. The present invention meets the need for improved therapies for treating type 1 diabetes, type 2 diabetes and other conditions.

Some embodiments of the present invention provide methods and compositions for stimulating islet cell neogenesis with HIP2, a peptide fragment of the human protein regenerating islet-derived 3 alpha protein (REG3A) (NM_138937.1), also known as pancreatitis-associated protein precursor (NP 002571), located on chromosome 2p12. In some embodiments, HIP2 induces or stimulates islet neogenesis from progenitor cells resident within the pancreas. In some embodiments, this neogenesis agent is used in accordance with the methods of the invention to treat diseases associated with low or inadequate levels of insulin or insulin activity resulting in aberrant carbohydrate metabolism that may result from pancreatic islet dysfunction or immune destruction. In some embodiments, these diseases include diabetes mellitus (type 1 diabetes), type 2 diabetes (non-insulin dependent diabetes mellitus and insulin requiring adult onset diabetes, diabetes in childhood and adolescence), and Latent Autoimmune Diabetes in Adults (LADA).

Some embodiments of the invention also provide pharmaceutical compositions and therapies for the treatment of pancreatic dysfunction, including type 1 and type 2 diabetes, with such compositions. In one embodiment, these compositions comprise HIP2. In another embodiment, these compositions comprise HIP2 and other agents that affect glucose metabolism. In some embodiments, these other agents that affect glucose metabolism are agents that are involved in pancreatic islet neogenesis and agents that inhibit, block, or destroy the autoimmune cells that target pancreatic islet cells. In one embodiment, the therapies of the invention are practiced by administering a therapeutically effective amount of HIP2 to a mammal in need of such therapy. In another embodiment, the therapies of the invention are practiced by administering a therapeutically effective amount of HIP2 to a mammal in need of such therapy in combination with another agent (such as a hormone or compound) that affects glucose metabolism, including but not limited to hormones or compounds that are involved in beta cell regeneration, satiety, and gastric emptying, such as GLP-1, GIP, GLP-1 receptor analogs, GLP-1 analogs, and Dipeptidyl Peptidase-4 Inhibitors, which prevent destruction of GLP-1, and agents that inhibit, block, or destroy the autoimmune cells that target pancreatic cells. In some embodiments, the HIP2 and the other agent may be administered separately or may first be admixed to provide a combination composition of the invention and administered simultaneously.

As will be appreciated by those of skill in the art, the preceding paragraph exemplifies some embodiments of the present invention which provide methods of treating a disease or condition associated with impaired pancreatic function in a subject in need thereof, comprising administering to the subject a therapeutically effective amount of HIP2, or an analog or derivative thereof and one or more agents selected from the group consisting of: an immune therapy agent and an additional agent that stimulates islet cell regeneration. In some embodiments, the immune therapy agent is selected from the group consisting of: anti-CD3 antibodies, sirolimus, tacrolimus, a heat-shock protein 60, an anti-glutamic acid decarboxylase 65 vaccine, mycophenolate mofetil alone or in combination with daclizumab, an anti-CD20 agent, rituximab, campath-1H, lysofylline, vitamin D, IBC-VSO vaccine, interferon-alpha, and a vaccine using CD4$^+$CD25$^+$ antigen-specific regulatory T cells. In some embodiments, the additional agent that stimulates islet cell regeneration is selected from the group consisting of: a HIP or a HIP-related peptide, amylin, pramlintide, insulin, exendin-4, GIP, GLP-1, GLP-1 receptor agonists, GLP-1 analogs, hamster INGAP peptide and related peptides, liraglutide, and a dipeptidyl peptidase inhibitor which blocks the degradation of GLP-1.

The following definitions are provided to assist the reader. Unless otherwise defined, all terms of art, notations and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not necessarily be construed to represent a substantial difference over the definition of the term as generally understood in the art.

As used herein, "treating" a condition or patient refers to taking steps to obtain beneficial or desired results, including clinical results. For purposes of this invention, beneficial or desired clinical results include, but are not limited to, alleviation or amelioration of one or more symptoms of diabetes, diminishment of extent of disease, delay or slowing of disease progression, amelioration, palliation or stabilization of the disease state, and other beneficial results described below. Symptoms of diabetes include low or inadequate levels of insulin or insulin activity, frequent urination, excessive thirst, extreme hunger, unusual weight loss, increased fatigue, irritability, blurry vision, genital itching, odd aches and pains, dry mouth, dry or itchy skin, impotence, vaginal yeast infections, poor healing of cuts and scrapes, excessive or unusual infections, hyperglycemia, loss of glycemic control, fluctuations in postprandial blood glucose, fluctuations in blood glucagon, fluctuations in blood triglycerides. Diabetes may be diagnosed by methods well known to one of ordinary skill in the art. For example, commonly, diabetics have a plasma blood glucose result of greater than 126 mg/dL of glucose. Pre diabetes, which may also be treated by the compositions and methods of the invention is commonly diagnosed in patients with a blood glucose level between 100 and 125 mg/dL of glucose. Other symptoms may also be used to diagnose diabetes, related diseases and conditions, and diseases and conditions affected by diminished pancreatic function.

As used herein, "reduction" of a symptom or symptoms (and grammatical equivalents of this phrase) means decreasing of the severity or frequency of the symptom(s), or elimination of the symptom(s).

As used herein, a "pathology associated with impaired pancreatic function" is one in which the pathology is associated with a diminished capacity in a subject for the pancreas of the subject to produce and/or secrete hormones and/or cytokines. Preferably this hormone or cytokine is insulin. Pathologies that are associated with impaired pancreatic function include type 1 diabetes, new onset type 1 diabetes, type 2 diabetes, latent autoimmune diabetes of adulthood, pre-diabetes, impaired fasting glucose, impaired glucose tolerance, insulin resistant syndrome, metabolic syndrome, being overweight, obesity, hyperlipidemia, hypertriglyceridemia, eating disorders and polycystic ovarian syndrome.

As used herein, "administering" or "administration of" a drug to a subject (and grammatical equivalents of this phrase) includes both direct administration, including self-administration, and indirect administration, including the act of prescribing a drug. For example, as used herein, a physician who instructs a patient to self-administer a drug and/or provides a patient with a prescription for a drug is administering the drug to the patient.

As used herein, a "subject" or "patient" is a mammal, typically a human, but optionally a mammalian animal of veterinary importance, including but not limited to horses, cattle, sheep, dogs, and cats.

As used herein, a "manifestation" of a disease refers to a symptom, sign, anatomical state (e.g., lack of islet cells), physiological state (e.g., glucose level), or report (e.g., triglyceride level) characteristic of a subject with the disease.

As used herein, a "therapeutically effective amount" of a drug or agent is an amount of a drug or agent that, when administered to a subject with a disease or condition, will have the intended therapeutic effect, e.g., alleviation, amelioration, palliation or elimination of one or more manifestations of the disease or condition in the subject. The full therapeutic effect does not necessarily occur by administration of one dose and may occur only after administration of a series of doses. Thus, a therapeutically effective amount may be administered in one or more administrations.

As used herein, a "prophylactically effective amount" of a drug is an amount of a drug that, when administered to a subject, will have the intended prophylactic effect, e.g., preventing or delaying the onset (or reoccurrence) of disease or symptoms, or reducing the likelihood of the onset (or reoccurrence) of disease or symptoms. The full prophylactic effect does not necessarily occur by administration of one dose and may occur only after administration of a series of doses. Thus, a prophylactically effective amount may be administered in one or more administrations.

As used herein, "TID", "QD" and "QHS" have their ordinary meanings of "three times a day", "once daily," and "once before bedtime", respectively.

Administration of an agent "in combination with" includes parallel administration (administration of both the agents to the patient over a period-of time, such as administration of a monoclonal antibody and a peptide hormone such as an incretin hormone or analog on alternate days for one month), co-administration (in which the agents are administered at approximately the same time, e.g., within about a few minutes to a few hours of one another), and co-formulation (in which the agents are combined or compounded into a single dosage form suitable for oral, subcutaneous or parenteral administration).

DPP-4 Inhibitors are dipeptidyl peptidase-4 inhibitors.

Hamster INGAP is a non-human islet neogenesis associated peptide.

GIP is Gastric Inhibitory Peptide, also known as Glucose-Dependent Insulinotropic Polypeptide.

GLP-1 is Glucagon-like Peptide 1.

HIP (SEQ ID NO:2) is a Human proIslet Peptide in purified, synthetic, or recombinant form. HIP and SEQ ID NO:2 are used interchangeably herein.

HIP1 (SEQ ID NO:3) is a Human proIslet Peptide in purified, synthetic, or recombinant form. HIP1 and SEQ ID NO:3 are used interchangeably herein.

HIP2 (SEQ ID NO:4) is a Human proIslet Peptide in purified, synthetic, or recombinant form. HIP2 and SEQ ID NO:4 are used interchangeably herein.

There has been confusing nomenclature in the literature regarding the regenerative processes of the pancreas. Often the term islet "cell" has been used synonymously with beta cells, and this distinction is important, as new therapies for the treatment of diabetes are considered. The pancreatic islets are not cells, but are structures, each of which is composed an estimated 1000 cells of four distinct cell types: 1) Beta cells that make insulin and amylin and comprise 65-80% of the islet cells; 2) Alpha cells that release glucagon and make up 15-20% of the cells; 3) Delta cells that make somatostatin; and 4) Pancreatic polypeptide (PP) cells, sometimes referred to as gamma cells. Delta and PP cells comprise less than 10% of the islet structure. Islet structures comprise only 1-2% of the pancreatic mass, yet utilize 20% of the blood supply to the pancreas and are considered one of the most vascularized tissues in the body.

There is a highly organized arrangement of the four types of cells within the islet structure. The delivery of blood flow within each islet is in a centrifugal manner with the beta cells located most centrally, and therefore receiving the core blood supply, while the alpha, delta and pancreatic polypeptide cells are positioned outside the beta cells in a lower state of perfusion.

In addition to glucose levels, which affect the beta cells, beta cells are coupled electrically to other beta cells, but not to other islet or pancreas cells. This elaborate system of communication within the islet may explain a compensatory rise in alpha cells within an islet when there is a significant decline in the beta cell mass.

The Human proIslet Peptides are active fragments of human REG3A or pancreatitis-associated protein precursor, the gene for which is located on chromosome 2p12. The REG3A protein from which HIP2 is derived is shown in Table 1. The domain which provides HIP2 is shown in boldface.

TABLE 1

REG3A/Pancreatitis-associated protein precursor amino acid sequence amino acid sequence.

MLPPMALPSVSWMLLSCLMLLSQVQGEEPQRELPSARIRCPKGSKAYGSHCYALFLSPK (SEQ ID NO: 6)

SWTDADLACQKRPSGNLVSVLSGAEGSFVSSLVKSIGNSYSYVWIGLHDPTQGTEPNG

EGWEWSSSDVMNYFAWERNPSTISSPGHCASLSRSTAFLRWKDYNCNVRLPYVCKFTD

HIP is the putative human homologue of the hamster INGAP peptide. U.S. Pat. No. 5,834,590, incorporated herein by reference in its entirety, discloses a hamster islet neogenesis associated protein (INGAP) and associated peptides at least 15 amino acids in length. A BLAST2P alignment of human REG3A and hamster INGAP performed on the NCBI website is shown below in Table 2.

TABLE 2

BLAST2P alignment of REG3A (SEQ ID NO: 6) and golden hamster INGAP (SEQ ID NO: 7).

| REG3: | 1 MLPPMALPSVSWMLLSCLMLLSQVQGEEPQRELPSARIRCPKGSKAYGSHCYALFLSPKS | 60 |
|---|---|---|
| | M+ PM L  +SWMLLSCLM LS V+GEE Q++LPS+RI CP+GS AYGS+CY+L L P++ | |
| INGAP: | 1 MMLPMTLCRMSWMLLSCLMPLSWVEGEESQKKLPSSRITCPQGSVAYGSYCYSLILIPQT | 60 |
| REG3: | 61 WTDADLACQKRPSGNLVSVLSGAEGSFVSSLVKSIGNSYSYVWIGLHDPTQGTEPNGEGW | 120 |
| | W++A+L+CQ    SG+L  +LS  E +FVSSLVK+    +Y Y+WIGLHDP+ GT PNG GW | |
| INGAP: | 61 WSNAELSCQMHFSGHLAFLLSTGEITFVSSLVKNSLTAYQYIWIGLHDPSHGTLPNGSGW | 120 |
| REG3: | 121 EWSSSDVMNYFAWERNPSTISSPGHCASLSRSTAFLRWKDYNCNVRLPYVCKF | 173 |
| | +WSSS+V+ ++ WERNPS  +  G+CA LS+ + F +W+D+NC   LPY+CKF | |
| INGAP: | 121 KWSSSNVLTFYNWERNPSIAADRGYCAVLSQKSGFQKWRDFNCENELPYICKF | 173 |

In boldface in Table 2 above, is the domain in REG3A from which HIP2 SEQ ID NO:4 is derived and the corresponding hamster sequence in INGAP. In U.S. Patent Publication No. 20040132644, incorporated herein by reference in its entirety, an INGAP peptide shown in bold above in Table 2 is disclosed. This hamster INGAP peptide is purportedly being studied for its efficacy in stimulating islet neogenesis.

Microarray analysis of gene expression in NOD mice has shown the upregulation of the Reg genes specifically in islet neogenesis. In addition, Reg genes have been known to upregulate in late fetal development to populate the pancreas of a developing human to maintain its own glucose metabolism post partum. Hao et al., 2006, Nature Medicine 12(3): 310-6 showed that co-transplantation of fetal tissue with non-endocrine pancreatic epithelial cells (NEPECs) resulted in stimulation of new islet structures from the NEPEC population. The upregulation of Reg in the co-transplanted fetal material was likely the stimulus for this effect.

Hamster INGAP has been the subject of clinical trials. While hamster INGAP was apparently well tolerated in Phase I and II trials, a Phase II trial had high drop out of diabetic patients due to discomfort and bruising at the hamster INGAP injection site. Little effectiveness was found for hamster INGAP in the Phase II trial as well. The HIP2-based methods and compositions of the present invention should not have these problems because the API used in them is derived from human, as opposed to hamster, sequences. Further, HIP2 may be administered at an increased number of doses a day. The number of daily doses may be one or more, including 2, 3, 4, 5, 6, 7, 8, 9 or 10 doses per day. The doses may be given before meals to increase effectiveness in some patients. HIP2 stimulates differentiation of progenitor cells within the pancreas into new islet structures. Administration of HIP2 immediately prior to meals and its presence during hyperglycemia following ingestion of the meal mimics the wild type secretion schedule or REG3A, which provides more effective treatment to patients.

Despite the adverse effects shown in the Phase II hamster INGAP trials, INGAP did show some signs of effectiveness in the trials. Patients treated with 600 mg/day of hamster INGAP showed an increase in C-peptide secretion. In the 300 mg/day treatment group of the Phase II study, 22% of the patients had a >50% increase in GAD65 antibody titers. GAD65 antibody binds to lymphocytes which attack beta cells within the islets. Thus a rise in GAD65 antibody titers reflects new beta cell production associated with islet neogenesis stimulated by hamster INGAP. Also, hemoglobin A1C fell in type 2 diabetes patients. This is correlated to a decrease in glycemic exposure, and thus a lower average blood glucose and indicates that hamster INGAP had some positive effect on islet function in patients, despite its adverse effects.

In one embodiment, HIP2 is provided by the present invention in purified, synthetic, or recombinant form and is administered in accordance with the methods of the invention to induce pancreatic islet neogenesis. HIP2 is advantageous relative to the non-human hamster INGAP, because HIP2 does not contain any non-human peptide sequence. Thus, there is little chance for immune reaction when HIP2 is administered to humans, as opposed to the hamster INGAP peptides.

Further, HIP2, may be stably stored for long periods of time. HIP2 is stable for months when stored at 20° C. in isotonic saline.

In a specific embodiment, HIP2 is functionally hyperactive, i.e., capable of exhibiting greater activity of one or more of the functional activities associated with REG3A, other HIP peptides, and non-human HIP homologues, such as the hamster INGAP.

Due to the degeneracy of nucleotide coding sequences, a variety of DNA sequences which encode the same or a substantially similar amino acid sequence as HIP2 may be used in the practice of some embodiments of the present invention to prepare expression vectors for the production of recombinant HIP2. In some embodiments, these include, but are not limited to, nucleic acid sequences comprising all or portions of HIP2 that are altered by the substitution of different codons that encode the same or a functionally equivalent amino acid residue within the sequence, thus producing a silent change. In some embodiments the HIP2 derivatives of the invention include, but are not limited to, those containing, as a primary amino acid sequence, all or part of the amino acid sequence of HIP2 including altered sequences in which functionally equivalent amino acid residues are substituted for residues within the sequence resulting in a silent change. For example, one or more amino acid residues within the sequence can be substituted by another amino acid of a similar polarity that acts as a functional equivalent, resulting in a silent alteration. In some embodiments, substitutes for an amino acid within the sequence may be selected from other members of the class to which the amino acid belongs. In some embodiments, the nonpolar (hydrophobic) amino acids include alanine, leucine, isoleucine, valine, proline, phenylalanine, tryptophan and methionine. In some embodiments, the polar neutral amino acids include glycine, serine, threonine, cysteine, tyrosine, asparagine, and glutamine. In some embodiments, the positively charged (basic) amino acids include arginine, lysine and histidine. In some embodiments, the negatively charged (acidic) amino acids include aspartic acid and glutamic acid. In some embodiments, HIP derivatives of the invention also include, but are not limited to, those containing, as a primary amino acid sequence, all or part of the amino acid sequence of HIP including altered sequences in which amino acid residues are substituted for residues with similar chemical properties. In a specific embodiment, 1, 2, 3, 4, or 5 amino acids of HIP2 are substituted resulting in analogs and/or derivatives of HIP2.

In a specific embodiment, chimeric or fusion proteins may be used in the method of the invention. As used herein, a "chimeric protein" or "fusion protein" comprises HIP2 or an analog or derivative thereof operatively-linked to a non-HIP2 polypeptide or an analog or derivative thereof. Within the fusion protein, HIP2 and the non-HIP polypeptide are "operatively-linked", that is they are fused in-frame with one another. In some embodiments, the non-HIP polypeptide can be fused to the N-terminus or C-terminus of HIP2. In some embodiments, the fusion protein may be HIP2 containing a heterologous signal sequence at its N-terminus. In certain host cells (e.g., mammalian host cells), expression and/or secretion of HIP2 or an analog or derivative thereof can be increased through use of a heterologous signal sequence. In yet another embodiment, the fusion protein is a HIP2-immunoglobulin fusion protein in which the HIP2 sequence is fused to sequences derived from a member of the immunoglobulin protein family. In some embodiments, the HIP2-immunoglobulin fusion protein can be incorporated into pharmaceutical compositions and administered to a subject to inhibit an immunological response according to the present invention.

In some embodiments, HIP2 or an analog or derivative thereof, or a HIP2-chimeric or fusion protein for use in the methods of the invention may be chemically modified for the purpose of improving bioavailability, and/or increasing efficacy, solubility and stability. For example, the protein may be covalently or non-covalently linked to albumin, transferrin or polyethylene glycol (PEG).

In some embodiments, HIP2 or an analog or derivative thereof, or a HIP2-chimeric or fusion protein for use in the method of the invention can be produced by standard recombinant DNA techniques in accordance with the teachings of the invention. For example, DNA fragments coding for the different polypeptide sequences may be ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In further embodiments, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence. Moreover, many expression vectors are commercially available that already encode a fusion moiety (e.g., a GST polypeptide). In some embodiments, a HIP2-encoding nucleic acid can be cloned into such an expression vector such that the fusion moiety is linked in-frame to HIP2. In some embodiments, the fusion protein can be HIP2 fused to a His tag or epitope tag (e.g. V5) to aid in the purification and detection of the recombinant HIP2, or to mask the immune response in a subject. The short amino acid sequences of HIP2 and its analogs and derivatives make synthetic production of these valuable peptides readily practicable as well, and a variety of automated instruments for peptide synthesis are commercially available, and synthetic methods for peptide synthesis not requiring automation have long been known and can be used in accordance with the teachings herein to prepare HIP2 or an analog or derivative thereof.

In some embodiments, HIP2 or an analog or derivative thereof, or a HIP2-chimeric or fusion protein can be modified so that it has an extended half-life in vivo using any methods known in the art. For example, the Fc fragment of human IgG or inert polymer molecules such as high molecular weight polyethyleneglycol (PKG) can be attached to HIP2 or an analog or derivative thereof with or without a multifunctional linker either through site-specific conjugation of the PEG to the N- or C-terminus of the protein or via epsilon-amino groups present on lysine residues. In some embodiments, linear or branched polymer derivatization that results in minimal loss of biological activity will be used. The degree of conjugation can be closely monitored by SDS-PAGE and mass spectrometry to ensure proper conjugation of PEG molecules to HIP2 or an analog or derivative thereof. Unreacted PEG can be separated from HIP2-PEG conjugates by size-exclusion or by ion-exchange chromatography. PEG-derivatized conjugates can be tested for in vivo efficacy using methods known to those of skill in the art.

In some embodiments, the present invention provides HIP2-based therapies and methods for delivery of HIP2 in the treatment of diabetes and the various other indications involving impaired pancreatic function. As exemplified by the preceding statement, some embodiments of the present invention provide methods of treating a disease or condition associated with impaired pancreatic function in a subject in need thereof, comprising administering to the subject a therapeutically effective amount of HIP2, or an analog or derivative thereof. In some embodiments, the disease or condition associated with impaired pancreatic function is selected from the group consisting of: type 1 diabetes, new onset type 1 diabetes, type 2 diabetes, Latent Autoimmune Diabetes in Adults, pre-diabetes, impaired fasting glucose, fasting hyperinsulinemia, impaired glucose tolerance, insulin resistant syndrome, insulin deficiency, metabolic syndrome, obesity, anorexia, bulimia, neuropathic pain, pancreatitis, pancreatic cancer, hyperlipidemia, hypertriglyceridemia, eating disorders, anovulatory cycles, lack of or diminished insulin production resulting in aberrant glucose metabolism, and polycystic ovarian syndrome. In further embodiments, the disease or condition associated with impaired pancreatic function is selected from the group consisting of: type 1 diabetes, type 2 diabetes, Latent Autoimmune Diabetes in Adults, pre-diabetes, and metabolic syndrome.

In one embodiment of the invention, the therapeutically effective dose of HIP2 administered alone or in combination with other agents to treat diabetes or other conditions is in the range of 0.1 to 100 mg/day of HIP2 per kg of patient weight (0.1 to 100 mg/kg/day) when administered subcutaneously. In one embodiment, the dose is in the range of 1 to 50 mg/kg/day. In one embodiment, the dose is in the range of 5 to 25 mg/kg/day. In one embodiment, the dose is 10 mg/kg/day. In other embodiments, the HIP2 is administered by a route other than subcutaneous administration, and the dose is adjusted to equal a dose bioequivalent to the subcutaneous dose. In another embodiment, the invention provides unit dose forms of HIP2 that provide a dose that allows the practitioner to practice the method conveniently. In some embodiments, such unit dose forms of the invention include those containing 50, 100, 150, 200, 250, 300, 350, 400, 450, and 500 mg of HIP2 in unit dose form.

Thus, some embodiments of the invention provide a method for administering a therapeutically effective dose of HIP2. In one embodiment, the method involves administering a therapeutically effective dose of HIP2 in the range of 0.1 to 100 mg/kg/day with or without adjunct therapy (such as administration of a GLP-1 receptor agonist, a GLP-1 analog, and/or a dipeptidyl peptidase inhibitor). In some embodiments, the dose of HIP2 may be conveniently administered via subcutaneous or intramuscular injection to stimulate islet differentiation from progenitor cells and endogenous insulin production within the pancreas of patients to treat type 1 diabetes, type 2 diabetes, prediabetes/impaired fasting glucose and insulin resistant syndromes, polycystic ovarian syndrome and associated infertility, obesity, metabolic syndrome, hypertriglyceridemia, hypercholesterolemia, and/or other conditions in which there is a lack of or diminished insulin production and/or alterations in glucose metabolism or insulin secretion.

In one embodiment of the method, a therapeutically effective dose of HIP2 alone or in combination with other agents is administered to a patient via subcutaneous or intramuscular injection 10 minutes to 60 minutes (for example, 20 minutes or a half an hour) prior to each meal and at bedtime. In another embodiment of the method of the invention especially beneficial for patients with diabetes, a therapeutically effective dose of HIP2 is administered alone or in combination with other agents via subcutaneous or intramuscular injection at least twice daily, prior to the two largest meals.

In another embodiment of the method especially beneficial for patients with the metabolic syndrome, polycystic ovarian syndrome, impaired fasting glucose/prediabetes and other conditions, who have previously been untreated with diabetes medications or medications associated with hypoglycemia, HIP2 will be administered subcutaneously or intramuscularly 10 minutes to 60 minutes (i.e., 20 minutes) prior to the two largest meals ingested per day. In some embodiments, patients treated pursuant to this method check glucose levels 2 hours after the meals that were preceded by an injection of HIP2. In some embodiments, if there are two distinct episodes in which the 2-hour postprandial glucose level is less than 70 mg/dL for a given meal (breakfast, lunch or dinner), then the dose prior to that meal will be reduced by half in future administrations. In some embodiments, if there are glucose levels of less than 70 mg/dL after the dose has been reduced by half, HIP2 dosing will be completely discontinued for that meal thereafter.

In another embodiment of the method especially beneficial for newly diagnosed type 2 diabetes patients, who have previously been untreated with diabetes medications, HIP2 is administered subcutaneously or intramuscularly 10 minutes to 60 minutes (i.e., 20 minutes) prior to each meal and at bedtime. In some embodiments, patients treated pursuant to this method check glucose levels before and 2 hours after each meal. In some embodiments, if there are two distinct episodes in which the 2-hour postprandial glucose level is less than 70 mg/dL for a given meal, then the dose prior to that meal will be reduced by half in the future. In some embodiments, if there are glucose levels less than 70 mg/dL after the dose has been reduced by half, HIP2 administration will be completely discontinued prior to that meal in the future.

In another embodiment of the method especially beneficial for patients with type 1 and 2 diabetes who are treated with insulin, HIP2 is administered subcutaneously or intramuscularly as described above. In some embodiments, patients treated per this embodiment of the method will check glucose levels immediately before meals, 2 hours after meals, and at bedtime. In some embodiments, to minimize the risk of hypoglycemia when HIP2 therapy is initiated, patients are instructed to reduce their mealtime insulin doses by 10% from their baseline dosage during the first week of therapy. In some embodiments, if any patient has an episode of symptomatic hypoglycemia with a glucose level of less than 70 mg/dL, all of the pre-meal insulin doses will be reduced by 10%. In some embodiments, if there are two distinct episodes in which the 2-hour postprandial glucose level is less than 70 mg/dL for a given meal, the dosage of pre-meal insulin for that meal will be reduced by an additional 10% beginning at the next meal after the episode. In some embodiments, if the fasting glucose is less than 70 mg/dL, the evening long-acting insulin or basal rate, if the patient is on an insulin pump, will be reduced by 10%. In some embodiments, during weeks 2-12 of HIP2 therapy, the pre-meal insulin level will be reduced by an additional 5% each week from the previous dosage before each meal. In some embodiments, if any patient has an episode of symptomatic hypoglycemia with a glucose level of less than 70 mg/dL, all of the pre-meal insulin doses will be reduced by 10%. In some embodiments, if there are two distinct episodes in which the 2-hour postprandial glucose level is less than 70 mg/dL for a given meal, the dose of pre-meal insulin for that meal in the future will be reduced by an additional 10% beginning at the next meal after the episode. In some embodiments, if the fasting glucose is less than 70 mg/dL, the evening long-acting insulin or basal rate, if the patient is on an insulin pump, will be reduced by 10%.

In another embodiment of the method especially beneficial for patients on a combination of insulin and oral medications, those patients on pre-meal and/or basal insulin will be instructed to reduce their mealtime insulin doses by 10% from their baseline dose during the first week of therapy to minimize the risk of hypoglycemia when HIP2 therapy is initiated. In some embodiments, if any patient has an episode of symptomatic hypoglycemia with a glucose level of less than 70 mg/dL, the pre-meal insulin doses will be reduced by 10%. In some embodiments, if there are two distinct episodes in which the 2-hour postprandial glucose level is less than 70 mg/dL for a given meal, the dose of pre-meal insulin for that meal in the future will be reduced by an additional 10% beginning at the next meal after the episode. In some embodiments, if the fasting glucose is less than 70 mg/dL, the evening long-acting insulin will be reduced by 10%. In some embodiments, during weeks 2-12 of HIP2 therapy, the pre-meal insulin level will be reduced by an additional 5% each week from the previous dose before each meal. In some embodiments, if any patient has an episode of symptomatic hypoglycemia with a glucose level of less than 70 mg/dL, all of the pre-meal insulin doses will be reduced by 10%. In some embodiments, if there are two distinct episodes in which the 2-hour postprandial glucose level is less than 70 mg/dL for a given meal, the dose of pre-meal insulin for that meal will be reduced by an additional 10% beginning at the next meal after the episode. In some embodiments, if the fasting glucose is less than 70 mg/dL, the evening long-acting insulin will be reduced by 10%.

In another embodiment of the method especially beneficial for patients on sulfonylureas, meglitinides or other diabetic medications that can result in hypoglycemia, the dose of such medication will be reduced by 50% when HIP2 therapy is initiated. In some embodiments, patients will check glucose levels two-hours after the meal before which HIP2 has been administered. In some embodiments, if any patient has an episode of symptomatic hypoglycemia with a glucose level of less than 70 mg/dL, or if there are two distinct episodes in which the 2-hour postprandial glucose level is less than 70 mg/dL for a given meal, administration of the oral agent (sulfonylurea, meglitinides, and the like) will be discontinued. In some embodiments, if there is another episode of symptomatic hypoglycemia or two distinct episodes in which the 2-hour postprandial glucose level is less than 70 mg/dL, then dosing of HIP2 will be discontinued prior to that particular meal in the future.

In another embodiment especially beneficial for patients with new onset type 1a diabetes, HIP2 will be administered over an 18-week period during which time insulin administration is tapered down, and glucose levels are maintained in a narrow window. In some embodiments, prior to treatment with HIP2, patients with new onset type 1a diabetes must first optimize their glucose levels in addition to usage of a targeted immune suppressant (such as treatment with anti-CD3 antibody at 5 ug/day intravenously for 5 consecutive days prior to treatment). In some embodiments, newly diagnosed type 1a patients will go through a protocol of intensive glucose management, which may include, but is not limited to, use of continuous glucose sensing, continuous subcutaneous insulin administration, and/or pramlintide therapy concomitantly with insulin.

In some embodiments, following the optimization of glucose levels, HIP2 can be administered over an 18 week evaluation period as described above. In some embodiments, avoidance of hypoglycemia is a primary goal, with a target upper limit for glucose of 180 mg/dL. In some embodiments, HIP2 is administered prior to meals and at bedtime. In some embodiments, HIP2 is dosed at 0.1 to 100 mg/kg/day, such as 1 to 25 mg/kg/day, or 5 to 15 mg/kg/day, or about 9 mg/kg/day. In one embodiment, the daily dose is administered in 4 divided doses. In some embodiments, these doses are given before meals and during the night, for example, at 3 a.m. In some embodiments, the present invention also provides methods for dosing HIP and HIP1 to treat the same diseases and conditions amenable to HIP2 treatment. In one embodiment, HIP1 is dosed at 0.1 to 100 mg/kg/day, such as 1 to 25 mg/kg/day, or 5 to 15 mg/kg/day, or about 8 mg/kg/day. In some embodiments, the daily dose can be administered in multiple divided doses, including 4 divided doses, as described above. In some embodiments, HIP is dosed at 0.1 to 100 mg/kg/day, such as 1 to 25 mg/kg/day, or 5 to 15 mg/kg/ day, or about 10 mg/kg/day, and again, the daily dose can be administered in multiple divided doses, including 4 divided doses, as described above.

In accordance with the one embodiment of the invention, HIP2 can be administered in combination with insulin. In some embodiments, the dose of insulin will be decreased over time ("tapered"), with close monitoring of stimulated C-peptide levels. In some embodiments, when normal C-peptide levels are achieved and glucose levels are within the desired target range, insulin administration will be discontinued. In some embodiments, HIP2 administration can be subsequently discontinued. In some embodiments, immune therapy to protect new islets can be administered in accordance with the method of the invention. Recent studies with humanized anti-CD3 antibodies have demonstrated that, among newly diagnosed type 1a patients, immune protection may be rendered for as long as 24-months.

In another embodiment especially beneficial for patients with existing type 1a diabetes and patients with Latent Autoimmune Diabetes of Adulthood (LADA), HIP2 is administered over at least an 18-week period during which time insulin administration is tapered down and glucose levels are maintained in a narrow window. In some embodiments, prior to treatment with HIP2, patients with existing type 1a diabetes or LADA will in some instances optimize their glucose levels in addition to use a targeted immune suppressant (such as treatment with anti-CD3 antibody at 5 ug/day intravenously for 5 consecutive days prior to treatment). In some embodiments, following the optimization of glucose levels, HIP2 is administered over an 18 week period as mentioned above. In some embodiments, avoidance of hypoglycemia is a primary goal, with a target upper limit of glucose of 180 mg/dL. In some embodiments, HIP2 is administered prior to meals and at bedtime. In some embodiments, HIP2 will continue to be administered while insulin administration is being tapered, with close monitoring of stimulated C-peptide levels. In some embodiments, when normal C-peptide levels are achieved and glucose levels are within the target range, insulin will be discontinued, and subsequently, HIP2 administration can in some patients be discontinued. In some embodiments, immune therapy to protect new islets will be dosed based upon the therapy type in accordance with the methods of the invention.

In another embodiment of the method especially beneficial for patients with new onset type 2 diabetes, HIP2 is administered to aid in replenishing lost beta cells, a loss that is progressive in type 2 diabetes. In some embodiments, to overcome the problem of insulin resistance associated with type 2 diabetes, HIP2 is administered at the onset of type 2 diabetes, optionally in combination with one or more additional pharmacological agents, to replenish the beta cell population and reduce the risk of further beta cell strain from hyperinsulinemia. In some embodiments, the agents that may be used in combination with HIP2 in the treatment of type 2 diabetes include, but are not limited to: exendin-4, GLP-1, GLP-1 analogues, Dipeptidyl Peptidase-4 Inhibitors, and Pramlintide. HIP2 is administered prior to meals and at bedtime. In some embodiments, HIP2 will be dosed at 0.1 to 100 mg/kg/day, such as 1 to 25 mg/kg/day, or 5 to 25 mg/kg/day, or about 16 mg/kg/day, optionally in 4 divided doses, as described above (before meals and in the nighttime, e.g. 3 a.m.). In some embodiments, HIP1 is dosed at 0.1 to 100 mg/kg/day, such as 1 to 25 mg/kg/day, or 5 to 25 mg/kg/day, or about 14 mg/kg/day, optionally in 4 divided doses, as described above. In some embodiments, HIP is dosed at 0.1 to 100 mg/kg/day, such as 1 to 25 mg/kg/day, or 5 to 25 mg/kg/day, or about 18 mg/kg/day, optionally in 4 divided doses, as described above.

In another embodiment of the method especially beneficial to patients with pre-existing type 2 diabetes and patients with type 1b diabetes being treated with an oral or injectable anti-diabetic agent, such as insulin, Pramlintide or exenatide, HIP2 is administered to aid in replenishing the beta cell loss, which is progressive in type 1b and type 2 diabetes. In some embodiments, to overcome the problem of insulin resistance associated with type 1b and type 2 diabetes, HIP2 is utilized in the treatment of patients with existing type 2 diabetes or patients with type 1b diabetes. In some embodiments, HIP2 is administered in conjunction with one or more pharmacological agents as a means of both replenishing the beta cell population and reducing the risk of further beta cell strain from hyperinsulinemia. In some embodiments, the agents that may be used in conjunction with HIP2 in the treatment of type 2 diabetes or type 1b diabetes wherein the patient is treated with oral or injectable anti-diabetic agents, may include, but are not limited to: exendin-4, GLP-1, GLP-1 analogues, Dipeptidyl Peptidase-4 Inhibitors, and Pramlintide. In some embodiments, HIP2 is dosed at 0.1 to 100 mg/kg/day, such as 1 to 25 mg/kg/day, or 5 to 25 mg/kg/day, or about 16 mg/kg/day, optionally in 4 divided doses, as described above. In some embodiments, HIP1 is dosed at 0.1 to 100 mg/kg/day, such as 1 to 25 mg/kg/day, or 5 to 25 mg/kg/day, or about 14 mg/kg/day, optionally in 4 divided doses, as described above. In some embodiments, HIP is dosed at 0.1 to 100 mg/kg/day, such as 1 to 25 mg/kg/day, or 5 to 25 mg/kg/day, or about 18 mg/kg/day, optionally in 4 divided doses, as described above. In some embodiments, the mode of delivery and dosage of the other pharmacological agent(s) administered in combination with HIP1, HIP2 and/or HIP will be determined based upon the selected agent.

In another embodiment of the method especially beneficial to patients with obesity, insulin resistance, metabolic syndrome/dymetabolic syndrome, polysistic ovarian syndrome and anovulatory cycles, HIP2 is administered in combination with other pharmacological agent(s) beneficial in the reduction or reversal of insulin resistance. Because reduced physical activity and dietary indiscretion are associated with obesity, insulin resistance, metabolic syndrome/dysmetabolic syndrome, polycystic ovarian syndrome and anovulatory cycles, in addition to restoring islet mass, it will be critical in some embodiments to address the problem of insulin resistance, which taxes the beta cell to over secrete insulin to overcome the insulin resistance. In some embodiments, HIP2 is therefore utilized in the treatment of obesity, insulin resistance, metabolic syndrome/dysmetabolic syndrome, polycystic ovarian syndrome and anovulatory cycles in combination with one or more pharmacological agents beneficial in the reduction or reversal of insulin resistance. In some embodiments, the agents that may be used in combination with HIP2 include, but are not limited to: exendin-4, GLP-1, GLP-1 analogues, Dipeptidyl Peptidase-4 inhibitors, and Pramlintide. In some embodiments, HIP2 is delivered either orally or subcutaneously prior to meals and at bedtime. In some embodiments, HIP2 is dosed at 0.1 to 100 mg/kg/day, such as 1 to 25 mg/kg/day, or 5 to 25 mg/kg/day, or about 16 mg/kg/day, optionally in 4 divided doses, as described above. In some embodiments, HIP1 is dosed at 0.1 to 100 mg/kg/day, such as 1 to 25 mg/kg/day, or 5 to 25 mg/kg/day, or about 14 mg/kg/day, optionally in 4 divided doses, as described above. In some embodiments, HIP is dosed at 0.1 to 100 mg/kg/day, such as 1 to 25 mg/kg/day, or 5 to 25 mg/kg/day, or about 18 mg/kg/day, optionally in 4 divided doses, as described above.

In another embodiment of the method, HIP2 is administered in a pharmaceutical composition of the invention in which the HIP2 is encapsulated, alone or in combination with one or more other agents, in a soluble liposome formulation. In one embodiment, this liposome formulation is administered orally.

In one embodiment of the liposome formulation, HIP2 is admixed in a soluble liposome preparation with other agents, wherein those other agents are selected from the group consisting of amylin and/or an amylin analog, such as Pramlintide, GIP, GLP-1 and/or homologous compounds and analogs, GLP-1 receptor analogs, which include Exendin-4, Liraglutide (NN2211), hamster INGAP or analogs thereof, another biologically active HIP peptide in addition to HIP2, and/or a Dipeptidyl Peptidase-4 inhibitor, which delays the degradation of GLP-1. In some embodiments, the other agent may affect beta cell regeneration, gastric emptying, satiety, insulin requirements (through their effect on the GLP-1 and amylin receptor sites in the pancreas, nucleus accumbens, area postrema, and gut).

In some embodiments, practice of the methods of the invention can involve multiple rounds, or "cycles," of treatment. For example, HIP2 can be administered until no further therapeutic benefit is observed, and then dosing can be discontinued until symptoms of the disease or condition being treated reoccur, at which time dosing can be readministered. In some embodiments, the dose of HIP2 administered can be reduced as evidence of therapeutic benefit appears.

Those of skill in the art will recognize upon review of the present disclosure that certain agents, when administered in combination with HIP2, can enhance the biological activity of HIP2 and therefore when administered in combination with such agents, the HIP2 dose may in some instances be titrated so as to reach a HIP2 concentration that yields the desired therapeutic effect. Those of skill in the art will also appreciate, in view of the disclosure herein, that the skilled artisan may select particular doses of and agents to be used in combination with HIP2 based on the disease and condition being treated and the medical status of the patient.

In one embodiment, the method of the invention is practiced to treat type 1or type 2 diabetes mellitus and related conditions in which there is a lack of or diminished insulin production in a patient resulting in aberrant glucose metabolism. In some embodiments, the method comprises administering to that patient an agent that stimulates pancreatic islet regeneration and/or differentiation from pancreatic progenitor cells into islet structures. In some embodiments, this agent is HIP2 or an analog or derivative thereof. In some embodiments, optionally HIP2 or a HIP2 analog or derivative is administered with the simultaneous or contemporaneous administration of an agent that inhibits the activity of and or blocks or destroys the autoimmune cells that target pancreatic islet beta cells and optionally another agent which may also stimulates pancreatic beta cell regeneration and/or result in elevation of GLP-1 or GLP-1 receptor stimulation or is a GLP-1 analog, or is a Dipeptidyl Peptidase-4 Inhibitor, which inhibits the degradation of GLP-1.

As exemplified by the preceding paragraph, some embodiments of the present invention provide methods of stimulating islet cell differentiation from progenitor cells into islet structures in a subject in need thereof, comprising administering to the subject a therapeutically effective amount of HIP2, or an analog or derivative thereof, and a therapeutically effective amount of one or more agents selected from the group consisting of: an immune therapy agent and an additional agent that stimulates islet cell regeneration.

In some embodiments, the therapeutic methods provided by the present invention address several different underlying mechanisms that result in either the absence of, or diminished or inadequate amounts of, insulin and other hormones, or which are otherwise produced in aberrant quantities. In some embodiments, the HIP2 based combination therapies provided by the present invention can restore more normal glucose metabolism, including achieving and maintaining appropriate levels of insulin, amylin, postprandial glucose, triglycerides, and glucagon levels and ameliorate the significant weight gain and increased risk for serious hypoglycemia that is associated with tight glycemic control using insulin or oral diabetic medications.

Some embodiments of the present invention also provide single agent therapies for treating insulin deficiency, including diabetes and related conditions. In some embodiments, these single agent therapies include methods for the administration of HIP2 or an analog or derivative thereof that stimulate pancreatic islet cell regeneration and/or transformation of new insulin producing islet cells from pancreatic progenitor cells located within the adult pancreas. In some embodiments, the islet cell neogenesis resulting from such administration with HIP2 can be used to treat diabetes and other diseases and conditions relating to aberrant glucose regulation. In various embodiments, these methods comprise the administration of HIP2 alone or in combination with an immune blocking agent and/or co administered with a GLP-1 receptor agonist, GLP-1, GLP-1 analog, or Dipeptidyl peptidase-inhibitor in the case for type 1 diabetes or HIP2 in combination with GLP-1 receptor agonist, GLP-1, GLP-1 analog, or dipeptidyl peptidase-inhibitor without the need for an immune blocker in the case of type 2 diabetes. In some embodiments, disease conditions amenable to treatment with this methodology include, but are not limited to, type 1 and 2 diabetes, where these treatments can be used to improve glycemic control, as measured by hemoglobin A1C, and to reduce bolus insulin before meals by at least 10-20%, with reduced fluctuations and decreased postprandial glucose, glucagon, and triglycerides. In some embodiments, these methods can also be used to prevent progression of impaired glucose tolerance to diabetes and to prevent progression of impaired fasting glucose to progression to impaired glucose tolerance and diabetes and to reverse newly diagnosed type 2 diabetes. It yet other embodiments, these methods can also be used to treat type 2 diabetes.

Exogenous injectable insulin is a therapy for patients with type 1 diabetes and other conditions in which insulin is either absent or present in diminished or inadequate amounts relative to the glucose content in the bloodstream. Insulin therapy does not treat the underlying mechanisms of disease resulting in type 1 diabetes and other such conditions in which there is diminished endogenous insulin production. The therapies, methods, modalities, and treatments described herein address the many facets of the causes and complications of diabetes. The unique therapies provided by the invention encompass diverse aspects of diabetology, metabolism, and immunology. In some embodiments, these therapies include those that restore normal levels of the many different hormones, in addition to insulin, that are diminished or absent in type 1 diabetes. In some embodiments, the methods of the invention provide for the regeneration of new pancreatic islet structures. In some embodiments, these new islet structures provide for the proliferation of new insulin producing cells, thereby ameliorating, diminishing, or abolishing the need for exogenous insulin among patients with type 1 diabetes and other conditions associated with inadequate insulin production and secretion.

In type 1 diabetes, there are several underlying mechanisms that result in significant reduction in the production of insulin. These include autoimmune destruction of the beta cells and reduction in regeneration capacity not only within the beta cells, but an inability of progenitor cells to differentiate into new islets may be due to the altered glucose milieu. In some embodiments, the present invention also provides combination treatment methods that are especially efficacious, because when the autoimmune response is blocked by the co-administration with HIP2 or a HIP2 analog or derivative of an immunosuppressant, the autoimmune cells that attack the pancreatic islet cells are blocked, and as peptides or other compounds that stimulate regeneration of the pancreatic islet cells are administered and exert their therapeutic effect, the patient becomes less dependent on insulin administration.

In some embodiments, the methods of the invention can even render some patients completely free of their dependence on administered insulin for both type 1 and 2 diabetes. Other studies (see the references Levetan et al., 2002, *Diabetes* 51 (supple 2):429, Levetan et al. *Diabetes* 2002, 51(suppl. 2):474, Levetan *Diabetes* 2001; 50(supple 2):2105PO, and Levetan et al., 2003, *Diabetes Care* 26:1-8, each incorporated herein by reference) show that, when diminished hormones other than insulin are replaced, insulin requirements in type 1 patients are significantly diminished with improved glucose control. By stimulating differentiation of new insulin producing islet structures and optionally blocking the immune cells that can destroy their function, the methods of the present invention have even greater promise of therapeutic benefit, because they result in sustained, endogenous production of insulin itself, and other co-secreted hormones such as amylin.

As exemplified by the preceding paragraph, some embodiments of the present invention provide methods of reducing insulin requirements in a subject in need thereof, comprising administering to the subject a therapeutically effective amount of HIP2, or an analog or derivative thereof. In some embodiments, the present invention provides methods of reducing insulin requirements in a subject in need thereof, comprising administering to the subject a therapeutically effective amount of HIP2, or an analog or derivative thereof and one or more agents selected from the group consisting of: an immune therapy agent and an additional agent that stimulates islet cell regeneration.

There is a demonstrated need for the therapeutic benefits provided by the present invention. There are new insulin formulations and evidence to support that intensive insulin therapy prevents deaths and reduces the rate of blindness, amputations, and kidney failure necessitating dialysis. Also, recent studies have demonstrated both microvascular and macrovascular/cardiovascular risk reduction among type 1 diabetes patients who have improved glycemic control. However, intensive insulin therapy utilizing modern modalities of multiple insulin injections and continuous insulin delivery via pump therapy is associated with a two-to-three fold increased risk of serious hypoglycemia requiring assistance from another person. In a clinical study setting, despite normalization of glucose in type 1 diabetes patients by means of intravenous insulin and glucose, the standard deviation in glucose levels, both high and low, is significantly wider than non-diabetic study subjects with the same average glucose over a 24-hour period. In some embodiments, the present invention offers an alternate means to achieve the therapeutic benefit of intensive insulin therapy with reduced iatrogenic risk, because the endogenous production of insulin stimulated by the present methods should provide more normal rates of insulin production than can be effectively mimicked by intensive insulin therapy.

Thus, despite insulin's availability and new technologies, including new formulations of human insulin, self blood glucose monitoring systems, continuous glucose sensors and pump therapy, normal glucose control is not approximated by current therapies. Moreover, the underlying mechanisms causing type 1 diabetes are not impacted by the current therapies available for patients with type 1 diabetes and conditions in which there is no or diminished or inadequate or otherwise aberrant insulin or amylin production and dysregulation of glucagon.

In some embodiments, the present invention provides new methods and pharmaceutical compositions for stimulating islet neogenesis, increasing insulin or other pancreatic hormone production in a patient in need thereof, and treating type 1 diabetes mellitus, type 2 diabetes mellitus and other conditions in which the lack of or diminished insulin production is a causative factor for the disease symptoms. In some embodiments, the methods and compositions of the invention can reverse the underlying pathologic mechanisms of these disease conditions. Thus, in some embodiments, the methods of the invention diminish, and in some cases eliminate, the need for insulin administration to patients formerly in need thereof.

In one embodiment of this method, an additional agent that stimulates islet regeneration and/or differentiation from pancreatic progenitor cells into insulin producing islet structures is co-administered with HIP2 or an analog or derivative thereof, including HIP and INGAP. In some embodiments, other agents that be administered with HIP2 for the treatment of type 1 and type 2 diabetes include amylin and/or an analog, such as Pramlintide, GIP, GLP-1 and/or homologous compounds and analogs, GLP-1 receptor analogs which include Exendin-4, Liraglutide (NN2211), hamster INGAP, or HIP analogs thereof, any biologically active HIP peptide and/or the Dipeptidyl Peptidase-4 inhibitors, which delay the degradation of GLP-1. In some embodiments, the second agent may affect beta cell regeneration, gastric emptying, satiety, or insulin requirements through impacting the GLP-1 and amylin receptor sites in the pancreas, nucleus accumbens, area postrema, and gut.

In some embodiments, a method of treating type 1 diabetes and other pathologies resulting from diminished pancreatic function, includes a five step process. In some embodiments, these steps include: 1) Intensive Glycemic Management, 2) Achievement and maintenance of 25-hyrdroxyvitamin D levels to >40 ng/dl via oral cholecalciferol (Vitamin D3), 3) Immune Therapy, 4) HIP2 administration and Insulin tapering followed by discontinuation of both HIP2 and Insulin, and 5) Repeated usage of immune modulation on a quarterly or annual basis dependent on immune therapy chosen.

Those of skill in the art would appreciate that the preceding paragraph exemplifies some embodiments of the invention providing methods of treating a disease or condition associated with impaired pancreatic function in a subject in need thereof, comprising the steps of: intensifying glycemic control; administering oral cholecalciferol; administering one or more immune therapies; administering a therapeutically effective amount of HIP2 in combination with insulin, wherein the insulin administered is decreased over time; and repeating the administering of the one or more immune therapies every 3 months to every 24 months.

In some embodiments, another method of the invention includes a two step process for the treatment of type 2 diabetes, obesity, overweight, insulin resistance, hyperlipidemia, hypertriglyceridemia, and eating disorders. In some embodiments, this process includes the steps of: 1) Achievement and maintenance of 25-hyrdroxyvitamin D levels to >40 ng/dl via oral cholecalciferol (Vitamin D3), and 2) Administration of HIP2 in combination with a GLP-1 or GLP-1 receptor agonist or GLP-1 analog or Dipeptidyl Peptidase-4 Inhibitor.

The first two steps of the five step process of treating type 1 diabetes and other pathologies resulting from diminished pancreatic function are described in more detail below. In some embodiments, for the first step (a three-month time period prior to the administration of HIP2 or HIP2 analog or derivative administration and prior to or with the simultaneous or contemporaneous administration of an agent that inhibits the activity of and or blocks or destroys the autoimmune cells that target islet beta cells), there will be a period of tight/intense glucose optimization. In some embodiments, this period of tight/intense glucose optimization may include multiple daily doses of insulin administered subcutaneously or via continuous subcutaneous administration through an insulin pump and may include the administration of SYMLIN® (amylin/pramlintide), which is also absent in type 1 diabetes and aberrantly secreted in type 2 diabetes. SYMLIN® (amylin/pramlintide), has been shown to reduce glycemic excursions in type 1 patients, while reducing insulin requirements before meals.

Additionally, throughout the period of tight control, immune therapy, and HIP2 administration, the invention in one embodiment contemplates the administration of vitamin D3, cholecalciferol, at a dose of about 1000-2000 IU/day. Recent studies have demonstrated that up to 54.7% of populations in the US, regardless of latitude, have low 25-hydroxyvitamin D levels. Vitamin D deficiency has been demonstrated not only to be associated with the increased risk of type 1 diabetes and seen at the onset of type 1 diagnosis but also to be commonly seen in patients with diabetes, including both type 1 and type 2 patients, and maintaining levels above 40 ng/ml is recommended to maintain normal immune function in those with and without diabetes. No adverse effects have been seen with doses up to 10,000 IU/day. Vitamin D in doses of 1000-2000 IU/day are continued to maintain 25-hydroxyvitamin D levels> 40 ng/dl for both type 1 and 2 diabetes patients.

In one embodiment of the inventive method, prior to the administration of the HIP2 or HIP2 analog or derivative, an immune modulator will be administered in accordance with the methods for which it is otherwise prescribed. In some embodiments, such immune modulators include immunomodulatory proteins and peptides that arrest pancreatic islet cell destruction. In one embodiment, the immune modulator is a monoclonal antibody that can delay the progression of islet loss or slow or stop the onset of type 1 diabetes. Anti-CD3 antibodies constitute a general class of agents useful in the methods of the invention. For example, suitable anti-CD3 antibodies for purposes of the present invention include the TRX4 (Ala-Ala and ChAglyCD3) antibody under development by TolerRx and the humanized anti-CD3 antibody described in the reference Herold et al., 30 May 2002, *NEJM* 346(22):1692-1698, incorporated herein by reference. In one embodiment, the Bluestone humanized anti-CD3 antibody is delivered intravenously, at least 14 days per year in a dose of 1-1.42 µg/kg on day 1, 5.67 µg/kg on day 2, 11.3 µg/kg on day 3, 22.6 µg/kg on day 4 and 45.4 µg/kg on days 5-14. In some embodiments, these therapies can be repeated annually or more frequently contemporaneously or following the administration of HIP2. In some embodiments, HIP2 administration can continue for days, weeks, or months. In one embodiment, HIP2 is administered for 3 months, and in another embodiment, HIP2 is administered for 6 months. In various embodiments, insulin administration is being tapered (decreased over time) as new islet cell formation occurs. In some embodiments, during the HIP2 treatment phase, Vitamin D and/or the administration of SYMLIN® (amylin/pramlintide) may be continued in some embodiments. In some embodiments, following the discontinuation of HIP2 and insulin therapy, immune modulation can be repeated annually or more frequently or as needed. For example, for the anti-CD3 antibodies, a recent study has reported efficacy for as long as 24 months.

In another embodiment, the immuno-modulatory compound is a lysofylline or a heat shock protein that can arrest or slow islet cell destruction. In some embodiments, such proteins include DIAPEP277™ (a 24 amino acid fragment of heat shock protein 60) under development by Developen AG. In one embodiment, DIAPEP277™ (a 24 amino acid fragment of heat shock protein 60) is delivered subcutaneously by administering 1 mg in 40 mg mannitol in vegetable oil subcutaneously at baseline and at one month and then at 3 month intervals. In some embodiments, DIAPEP277™ (a 24 amino acid fragment of heat shock protein 60) is continued throughout HIP2 therapy and following HIP2 therapy at quarterly intervals to protect newly generated islets from HIP2 therapy. In one embodiment of the combination therapy of the invention, HIP2 is co-administered with DIAPEP277™ (a 24 amino acid fragment of heat shock protein 60). In some embodiments, the DIAPEP277™ (a 24 amino acid fragment of heat shock protein 60) is first administered subcutaneously at a dose of about 1 mg, about 30 days prior to the initiation of the HIP2 therapy. In some embodiments, a second administration of the DIAPEP277™ (a 24 amino acid fragment of heat shock protein 60) is then made at the time (30 days after the first administration) of initiating the HIP2 therapy. In some embodiments, the HIP2 therapy may be repeated as necessary, and the DIAPEP277™ (a 24 amino acid fragment of heat shock protein 60) is administered at a frequency of about every 3 months.

In some embodiments, the new HIP2 therapeutic methods provided by the present invention address several different underlying mechanisms that result in either the absence of, or diminished or inadequate amounts of insulin and other hormones or which are otherwise produced in aberrant quantities. In some embodiments, the HIP2 based, HIP2 analog or derivative based, or combination therapies provided by the present invention can restore more normal glucose metabolism, including achieving and maintaining appropriate levels of insulin, amylin, postprandial glucose, triglycerides, and glucagon and ameliorate the significant weight gain and increased risk for serious hypoglycemia that is associated with tight glycemic control.

Those of skill in the art will appreciate in view of the disclosure herein that more than one agent that stimulates islet neogenesis and/or progenitor cell differentiation and/or which slows the degradation of such agents can be used in combination in the methods of the invention.

Optionally, in the practice of the methods of the invention, the HIP2 or analog or derivative thereof, with or without the co-administration of another selected agent, such as SYMLIN® (amylin/pramlintide) GLP-1, a GLP-1 receptor agonist, GLP-1 agonist, or dipeptidyl-4 peptidase inhibitor, which inhibits the degradation of GLP-1, which may reduce weight, improve satiety, slow gut absorption of glucose, may be used in combination with a specific agent that inhibits, blocks the activity of, or destroys autoimmune cells that target the pancreatic beta cells. In some embodiments, such agents include, for example, peptides, proteins, and synthetic compounds.

In one embodiment, the agent is a monoclonal antibody, a heat-shock protein, or another compound that specifically delays, prevents, or halts autoimmune destruction of the islet function. Those of skill in the art will appreciate in view of the disclosure herein that more than one agent that blocks autoimmune destruction of pancreatic islet function can be used in combination in the methods of the invention. In some embodiments, agents that inhibit, block the activity of, or destroy autoimmune cells that target the pancreatic islet function include: Anti CD-3 antibodies (hOKT3γ1 Ala-Ala and ChAglyCD3), Sirolimus (Rapamycin), Tacrolimus (FK506), a heat-shock protein 60 (DiaPep277) a anti-Glutamic Acid Decarboxylase 65 (GAD65) vaccine, Mycophenolate Mofetil alone or in combination with Daclizumab, the anti-CD20 agent Rituximab, Campath-1H (Anti-CD52 Antibody), lysofylline, and Vitamin D, IBC-VSO vaccine which is a synthetic, metabolically inactive form of insulin designed to prevent pancreatic beta-cell destruction, interferon-alpha vaccination using $CD4^+CD25^+$ antigen-specific regulatory T cells or a similar agent, designed to prevent pancreatic beta-cell destruction. In this latter embodiment, interferon-α vaccination using $CD4^+CD25^+$ antigen-specific regulatory T cells or a similar agent is used in the combination therapy for utilizing regulatory T cells either directly or through the use of anti-CD3 immunotherapy. This embodiment, which includes an immune agent would specifically be used in type 1 diabetes patients to protect newly generated islet cells from immune attack.

Thus, in some embodiments, the combination therapies and related methods of the invention involve the administration of HIP2 or analogs or derivatives thereof or co-administration of HIP2 or analogs or derivatives thereof with either one or more agents that stimulate islet differentiation from cells in the adult pancreas or with one or more agents that block autoimmune destruction of pancreatic beta cells or both. As used herein, an agent is "co-administered" or "used in combination" with another agent (also referred to herein as, "compound or "hormone") when the two or three agents are administered as part of the same course of therapy. In one embodiment, a first agent is first administered prior to administration of the second agent, and treatment with both is continued throughout the course of therapy. In another embodiment, the second agent is administered after the initiation or completion of the therapy involving the first agent. In other embodiments, the first agent is administered contemporaneously with the initiation of the therapy with the second agent. In another embodiment, a third agent is administered contemporaneously or before or after the administration of the first or second agent or both. In one embodiment, a therapy involving one or more agents to block or kill autoimmune cells that target pancreatic beta cells, which make insulin and amylin, is first administered prior to administration of the therapy that stimulates islet differentiation from progenitor cells in the adult pancreas. In another embodiment, treatment with the specific autoimmune blocker is continued after the cessation of treatment with agents that stimulate islet differentiation. In some embodiments, prior to or contemporaneously administration of immune modulating agents, there will be a period of intensified/tight glycemic control, which may include multiple daily injections of insulin, insulin pump therapy and/or usage of SYMLIN® (amylin/pramlintide) and/or vitamin D therapy in doses of 1000-2000 IU/day to maintain a 25-hydroxvitamin D level above 40 ng/ml. In some embodiments, this period may last for weeks or months; in one embodiment, the period is for at least 3 months.

As noted above, practice of the methods of the invention can involve multiple rounds, or "cycles," of treatment. For example, an administration of an agent that stimulates islet differentiation from progenitor cells together with an administration of an agent that blocks autoimmune cells that target pancreatic beta cells can be viewed as one cycle of the method of the invention that involves co-administration of both types of agents. Alternatively, in some embodiments, each administration of an islet differentiation agent can be viewed as a cycle of treatment, and if an autoimmune cell blocking agent is administered, it may be administered in only a subset of such cycles, or after the last administration of the islet differentiation agent. For example, only two DIAMYD™ (GADD65 vaccine) injections of aluminum formulated human recombinant GAD65 delivered 4 weeks apart subcutaneously have been needed in some instances to stave off further beta cell destruction in patients with autoimmune diabetes. A single course of anti-CD3 monoclonal antibody hOKT3gamma1 (Ala-Ala) results in improvement in C-peptide responses and clinical parameters for at least 2 years after onset of type 1 diabetes in some patients. Thus, depending on the selected immune blocker, the cyclicity of therapy may vary to protect new islets from immune attack. It will be understood that the above examples are for illustration only and not intended to limit the invention in any fashion. Those of skill in the art will also appreciate that, in many cases, the schedule of co-administration may differ in the first or a later therapeutic cycle for the convenience of the patient.

The combination therapies and related methods of the invention uniquely target the underlying pathologic mechanisms of type 1 diabetes with agents that regenerate new islet structures and/or differentiate pancreatic progenitor cells in combination with agents that provide targeted immune therapy. In some embodiments, this combination therapy can reverse, wholly in some patients and partially in others, the underlying mechanisms of type 1 diabetes, which is an autoimmune phenomenon in which anti-self antibodies attack the pancreas. Current therapies for type 1 diabetes that rely on the administration of insulin do not reverse the underlying defects in type 1 diabetes. Moreover, current immune therapies for type 1 diabetes are based upon rejection of pancreatic beta cells and do not impact the differentiation of new fully functional islet structures containing new alpha, beta, delta, and polypeptide cells within each new islet.

Among patients with type 2 diabetes, an immune blocking agent will not be necessary as the basis of the disease is not immune destruction, although there may be some type 2 diabetic patients that will benefit from such combination therapy. Recent studies have pointed to a potentially important role of vitamin D deficiency in type 1 diabetes. A recent study found that at the time of diagnosis, more patients with type 2 diabetes are vitamin D deficient than type 1 diabetes, and maintaining levels above 40 ng/ml is recommended to maintain normal immune function. No adverse effects have been seen with vitamin D doses up to 10,000 IU/day. Thus, in some embodiments, the methods of the invention that involve vitamin D co-therapy are beneficial to type 2 diabetic patients.

In some embodiments, the new methods provided by the present invention reverse the underlying pathologic mechanisms of type 2 diabetes and diseases and conditions resulting from decreased insulin production due to an imbalance between destruction, regeneration, and sustenance of beta cells via the differentiation of new islet structures, which contain fully functional new beta cells. As exemplified by the preceding statement, some embodiments of the present invention provide methods of stimulating islet cell differentiation from progenitor cells in a subject in need thereof, comprising administering to the subject a therapeutically effective amount of HIP2, or an analog or derivative thereof. In some embodiments, the methods and compositions of the invention can reduce the insulin and diabetes medication requirements of patients currently taking insulin due to having type 2 diabetes or another disease or condition and can improve glucose control in such patients. In some patients, treatment in accordance with the methods of the invention can ameliorate or obviate the need for administered insulin. The following section describes a variety of diseases and conditions that the methods and compositions of the present invention can be used to treat with therapeutic benefit.

In some embodiments, the HIP2 or HIP2 analog or derivative therapies or combination therapies of the present invention can be used to treat any mammal, including humans and animals, suffering from a disease, symptom, or condition related to a diminished production or secretion of insulin due to the loss of or diminished beta cell function or the need for greater insulin production than can be provided to the subject via differentiation of new islet structures from progenitor cells utilizing HIP2 compounds and methods of treatment.

In some embodiments, such diseases and conditions include type 1 diabetes mellitus, type 2 diabetes, pre-diabetes, impaired fasting glucose, fasting hyperinsulinemia, including but not limited to patients with type 1a diabetes patients or patients with Latent Autoimmune Diabetes of Adulthood who may manifest antibodies (anti-GAD65 antibodies, anti-islet antibodies, or anti-insulin antibodies) or those patients with type 1 diabetes with insulin deficiency without autoimmunity directed toward the beta cells (type 1b diabetes). Moreover, some embodiments of the present invention can be practiced with therapeutic benefit for patients newly diagnosed as having type 1 diabetes, the siblings and first degree relatives of patients with type 1 diabetes, and people with positive antibodies and other autoimmune conditions that indicate a predilection to type 1 diabetes. In one embodiment, the methods of the invention are practiced to reverse type 1 diabetes in a patient in need of such treatment.

In some embodiments, the combination therapies and related methods and compositions of the invention can also be employed as adjunctive therapy to insulin therapy in type 1 diabetes in children and adults, to ameliorate glucose swings in patients with diabetes, and in patients with poorly controlled diabetes, hypoglycemic unawareness, and recurrent hypoglycemia in type 1 diabetes.

In some embodiments, the HIP2 or HIP2 analog or derivative therapies and related methods and compositions of the invention can be used to treat patients having newly diagnosed type 2 diabetes, type 2 diabetes in children and adults with hyperglycemia, type 2 diabetes being concurrently treated with insulin, oral diabetic or other subcutaneous diabetic therapies, and poorly controlled type 2 diabetes. In some patients, both children and adults, the methods and compositions of the invention can reverse type 1 and 2 diabetes. In some embodiments, the methods and compositions of the invention can also be used to treat both children and adults having atypical forms of diabetes and patients having the conditions of postprandial hyperglycemia.

In some embodiments, the HIP2 or HIP2 analog or derivative therapies and related methods and compositions of the invention can also be used to treat patients who are children, as well, as adult patients, in need of weight loss, reduction in triglycerides, LDL cholesterol, including but not limited to achieve weight loss or treat obesity, overweight in patients having diabetes as well as those who do not have type 1 or 2 diabetes. In one embodiment, the methods and compositions of the invention are used to treat a patient having morbid obesity. In other embodiments, the methods and compositions of the invention are used to treat a patient having morbid obesity or patients having anorexia, bulimia, or other eating disorders.

In some embodiments, the single agent HIP2 therapies and related methods and compositions of the invention can also be used to treat children and adults having dysmetabolic syndrome or metabolic syndrome, as well as patients exhibiting the conditions of neuropathic pain syndromes secondary to altered glucose metabolism, and those with hypertriglyceridemia with and without diabetes, and postprandial hypertriglyceridemia. In one embodiment, these methods are practiced to treat polycystic ovarian syndrome in a patient in need of such treatment.

In some embodiments, other patients that can benefit from the HIP2 or HIP2 analog or derivative therapies and related methods of the invention include children and adult patients diagnosed as having conditions such as fasting hyperglycemia, pre-diabetes, impaired fasting glucose, impaired glucose tolerance, and hyperglycemic conditions generally.

In some embodiments, the HIP2 or HIP2 analog or derivative therapies and related methods and compositions of the invention can also be used to treat patients having neuropathic pain syndromes and neuropathy, regardless of whether the patient is diagnosed as diabetic.

In some embodiments, the HIP2 or HIP2 analog or derivative therapies and related methods and compositions of the invention can also be used to treat patients having recurrent pancreatitis or pancreatic cancer and can be used in all modalities aimed at achieving new islet structures derived from progenitor cells in the pancreas.

The following sections describe the agents useful in some embodiments of the methods of the invention. Those of skill in the art will appreciate, in view of the disclosure herein, that the skilled artisan may select particular agents based on the disease and condition being treated and the health and medical status of the patient.

In one embodiment of the methods of the invention, the agent that stimulates islet differentiation from pancreatic progenitor cells into insulin producing islet structures is selected from the group consisting of HIP2 or an analog or derivative thereof. In another embodiment, a combination of HIP2 and another agent may be administered to stimulate islet cell neogenesis. In some embodiments, this additional agent can be, for example, amylin and/or an analog, including but not limited to SYMLIN® (amylin/pramlintide), GLP-1 receptor analogs, exendin-4, BYETTA® (exenatide), Liraglutide (NN2211), GLA-1, GLP-1 analogs GIP, GLP-1, hamster INGAP, other incretin-mimetic hormones, and/or similarly acting compounds and agents, and agents that extend the half-life or increase the level or activity of any of the foregoing compounds and agents, such as, for example, dipeptidyl peptidase-4 inhibitors, which delay the degradation of GLP-1. There are numerous GLP-1 mimetics that act via direct agonist activity on the GLP-1 receptors or by inhibiting the degradation of GLP-1. These agents are useful in the methods of the invention. In some embodiments, GLP-1 mimetics can be used in conjunction with HIP and/or targeted immune therapy for the treatment of type 1 diabetes, and, as provided by the present invention, they can be used to improve glycemic control, increase satiety, delay gut glucose absorption and lead to a reversal of the underlying mechanisms resulting in type 1 diabetes. In some embodiments, these agents and methods may prevent progression of impaired glucose tolerance in diabetes; to prevent pre-diabetes, progression of impaired fasting glucose to impaired glucose tolerance and diabetes; to reverse newly diagnosed type 2 diabetes; to treat type 2 diabetes, and to treat or prevent overweight, obesity, polycystic ovarian syndrome, and neuropathic pain syndromes.

In some embodiments, methods, agents, and pharmaceutical formulations useful in the practice of the present invention to achieve pancreatic islet differentiation from progenitor cells in the adult pancreas include those described for other purposes in the following references, each of which is incorporated herein by reference: Rosenberg et al., 1992, *Adv. Exp. Med. Biol.* 321: 95-104; March 1996, *Diabetologia* 39(3): 256-62; July 1996, *Pancreas* 13(1):38-46; and November 2004, *Ann. Surg.* 240(5):875-84; Vinik et al., June 1997, *Horm. Metab. Res.* 29(6):278-93. In some embodiments, the successful stimulation of islet regeneration or differentiation of pancreatic progenitor cells can be shown through the increased production and/or secretion of insulin in a subject.

In one embodiment of the invention, amylin or an analog of amylin such as SYMLIN® (amylin/pramlintide) is employed prior to administration or in concomitant administration with HIP2. In some embodiments, amylin may be administered prior to islet regeneration and continued through the islet regeneration period administration in accordance with the teachings of the reference Young el al., 1997, *Curr. Opin. Endocrin. Diabetes* 4: 282-290, incorporated herein by reference. In one embodiment of the invention, amylin and/or an analog, including but not limited to Pramlintide, is administered subcutaneously to optimize glycemic control prior to the initiation of HIP2 and may then be used alone or in conjunction with other islet stimulating peptides, such as HIP2 or a HIP2 analog or derivative. In one embodiment, amylin or Pramlintide is dosed at 0.3-0.8 micrograms per kilogram patient weight. In one embodiment, this dose is administered subcutaneously before meals, for example, QHS and 3 AM. In one embodiment, the therapeutically effective dose is delivered subcutaneously or via an infusion device/pump and/or a transdermal, intranasal, buccal, microneedle delivery system, oral encapsulation method. In another embodiment, the therapeutically effective dose is administered utilizing sustained release formulations requiring administration by injection or other delivery method no more frequently than once a week, once every 2 weeks, or once monthly. As noted above, in some embodiments, amylin or Pramlintide is co-administered with another islet stimulating agent.

In one embodiment of the invention, a GLP-1 receptor analog, including exendin-4 or an analog of exendin 4 is employed in the method with HIP2 at doses of 5-10 mcg with meals. In some embodiments, exendin-4 can be formulated and administered for purposes of the present invention in accordance with the teachings of the following references, each of which is incorporated herein by reference: Alcantara et al., 1998, *Cell Biochem. Fund.* 16(1): 51-6; Dupre et al., 2004, *J. Clin. Endocrin. Metab.* 89(1): 3469-73; Edwards et al., 1999, *Diabetes* 48: 86-93; and Xu et al., 1999, *Diabetes* 48: 2270-76. In one embodiment, exendin-4 is dosed in the range of 5-10 micrograms before meals. In one embodiment, exendin-4 is administered subcutaneously alone or in conjunction with HIP2 and/or other islet stimulating peptides. In one embodiment, the therapeutically effective dose is administered subcutaneously. In another embodiment, delivery of exendin-4 is via transdermal, buccal, oral encapsulation methods, intranasal or microneedle delivery systems. In another embodiment, the therapeutically effective dose is contained in a sustained release formulation that requires administration no more frequently than once a week, once every 2 weeks, or once monthly. In one embodiment, exendin-4 is co-administered with HIP2 or another islet cell neogenesis or progenitor cell transformation agent among patients with type 1 or 2 diabetes, or those with obesity, overweight, insulin resistant syndrome, impaired fasting glucose, pre-diabetes, polycystic ovarian syndrome, the metabolic syndrome or eating disorders.

GIP and GLP-1 belong to the incretin family of growth hormones, and in one embodiment of the invention, an incretin hormone or analog with or without the concomitant usage of HIP2 is employed in the method to stimulate differentiation to islets from progenitor cells in the adult pancreas.

In various embodiments of the invention, GIP or a GIP analog is employed with HIP2. In some embodiments, GIP can be formulated and administered for purposes of the present invention in accordance with the teachings of the following references, each of which is incorporated herein by reference: Andersen et al., 1978, *J. Clin. Invest.* 62: 152-161; Creutzfeldt et al., February 1980, *Diabetes* 29(2): 140-5; Dupré et al., 1973, *J. Clin. Endocrin. Metab.* 37: 826-828; Ebert et al., 1980, *Clinical Gastroenterology* 9(3): 679-98; Elahi et al., 1979, *Am. J. Physiol.* 237: E185-E191, and 1994, *Regulatory Peptide* 51(1): 63-74; Krarup et al., June 1983, *J. Clin. Endocrin. Metab.* 56(6): 1306-12; Krarup et al., 1987, *Metabolism* 36(7): 677-82; Krarup et al., 1988, *Acta Med. Scand.* 223(5): 437-41; Lynn et al., 2003, *FASEB* 77:19-93; Meir et al., 2002, *Regulatory Peptides* 107:1-3; and Nauk et al., 1993, *J. Clin. Endocrin. Metab.* 76(4): 912-7.

In one embodiment, GIP is administered intravenously or subcutaneously in combination with HIP2 or an analog or derivative thereof and dosed at 2-10 nanograms per kilogram patient weight to provide a 30-minute continuous infusion by either intravenous or subcutaneous delivery time beginning 3-5 minutes before meals, before bedtime, and beginning at 3 AM. In one embodiment GIP is administered subcutaneously before meals, QHS, and 3 AM. In one embodiment, GIP is administered orally or using an infusion device or a transdermal, buccal, intranasal or microneedle delivery systems. In another embodiment, a sustained release formulation requiring administration no more frequently than once every week, once every 2 weeks, or once monthly injections is employed. Suitable compositions for administering GIP in accordance with some embodiments of the methods of the invention are described for other purposes in the reference Jones et al., 6 Nov. 1989, *Diabetes Res. Clin. Pract.* 7(4):263-9.

In various embodiments of the invention, GLP-1 or an analog, or a GLP-1 receptor agonist or a Dipeptidyl Peptidase-4 Inhibitor is employed in combination with HIP2 or an analog or derivative thereof, in the method to stimulate islet differentiation from progenitor cells. In some embodiments, GLP-1, GLP-1 receptor agonists, GLP-1 analogs and DPP-4 inhibitors can be formulated and administered for purposes of the present invention in accordance with the teachings of the following references, each of which is incorporated herein by reference: Elahi et al., 1994, *Regulatory Peptides* 5/(1): 63-74; Gutniak et al., 1994, *Diabetes Care* 17:1039-44; Kreymann et al., 1987, *Lancet* 2:1300-1304; Larsen et al., 1996, *Diabetes* 45(Suppl. 2): 233A (Abstract); Larsen et al., 2001, *Diabetes Care* 24(8): 1416-21; List et al., 2004, *Am. J. Physiol. Endocrin. Metab.* 286(6): E875-81; Lugari et al., 2000, *Horm. Metab. Res.* 32: 424-428; Marquez et al., March 1998, *Cell. Biochem. Funct.* 76(1):51-6; Meier et al., March 2004, *Critical Care Medicine* 32(3): 848-851; Meneilly et al., 2003, *Diabetes Care* 26: 2835-41; Nauk et al., 1996, *Diabetologia* 39(12): 1546-53; Thorens et al., December 1995, *Diabetes Metab.* 21(5):311-8; Vilsboll et al., 2003, *J. Clin. Endocrin. Metab.* 88(6): 2706-13; Wang et al., 1997, *J. Clin. Invest.* 99: 2883-2889; and Zander et al., 2002, *Lancet* 359: 824-30.

In various embodiments of the invention, GLP-1, a GLP-1 receptor agonist, or a GLP-1 analog is administered subcutaneously or DPP-4 inhibitors are given orally in combination with HIP2 or an analog or derivative thereof and dosed in the range of 400-800 mg per day at 8-20 mg per kilogram patient weight. In one embodiment GLP-1 is administered orally or subcutaneously before meals or QHS. In one embodiment, GLP-1 is administered using a continuous subcutaneous infusion device at a rate of 1-30 ng/kilogram body weight/minute or a transdermal, buccal, or microneedle delivery system to provide a 30-minute continuous infusion by either intravenous or subcutaneous delivery time beginning 3-5 minutes before meals, before bedtime, and beginning at 3 AM. In another embodiment, a sustained release formulation requiring administration no more frequently than once every week, once every 2 weeks, or once monthly injections is employed.

In one embodiment, Liraglutide (NN2211) is administered subcutaneously in combination with HIP2 or an analog or derivative thereof in doses of 10-40 micrograms per kilogram body weight. In another embodiment Liraglutide is administered subcutaneously before meals, QHS, and 3 AM. In another embodiment, Liraglutide is administered using an infusion device or a transdermal, buccal, or microneedle delivery system to provide a 30-minute continuous infusion by either intravenous or subcutaneous delivery time beginning 3-5 minutes before meals, before bedtime, and beginning at 3 am. In another embodiment, a sustained release formulation requiring administration no more frequently than once every week, once every 2 weeks, or once monthly injections is employed.

In one embodiment of the combination therapies of the invention, Liraglutide or NN2211 is administered at a dose of about 20 micrograms per kg of patient weight daily in combination with HIP2. In some embodiments, this dose will provide patients the ability to reduce bolus insulin before meals by 10-20% with reduced fluctuations and decreased postprandial glucose, glucagon, and triglycerides. Administration of Liraglutide in accordance with some embodiments of the methods of the invention can be used to improve glycemic control, as measured, for example and without limitation, by hemoglobin A1C, in type 1 diabetes; to prevent progression of impaired glucose tolerance in diabetes; to prevent progression of impaired fasting glucose to impaired glucose tolerance and diabetes; to reverse newly diagnosed type 2 diabetes; and to treat type 2 diabetes.

In an embodiment of the combination therapy of the invention, Liraglutide or NN2211 is administered at a dose of about 20 micrograms per kg of patient weight to an adult patient in the morning, about 4 hours before food intake, and at bedtime for three consecutive weeks during HIP2 therapy. In some embodiments, for patients initiating treatment with C-peptide levels lower than about 1.0 ng/mL, C-peptide levels are monitored, and when they rise above 0.5 ng/mL, the antibody hOKT3g1 (ala-ala) is administered for 12 consecutive days.

In the combination therapies of some embodiments of the invention, exendin-4 or synthetic exendin-4 or another GLP-1 analog, GLP-1 receptor agonist, or Dipeptidyl Peptidase-4 Inhibtor is administered prior to meals alone or with HIP2 or another islet differentiation agent to improve glycemic control prior to or during the initiation of HIP2 therapies. In some embodiments, such agents, when delivered prior to meals may result in a reduction in the need for insulin of at least 20% and appropriate tapering of insulin and diabetic medications will be conducted while HIP2 is administered. In some embodiments, as HIP2 and/or other agents are delivered in both type 1 and type 2 patients, careful tapering of insulin and other diabetes medications will take place to protect against hypoglycemia as new islet cells are differentiated from progenitor cells. In some embodiments, insulin and diabetes medications, including HIP2, will be ultimately tapered off, as the pancreas is repopulated with new functional islets. In some embodiments, for patients initiating treatment with C-peptide levels lower than about 1.0 ng/mL, C-peptide levels are monitored, and when they rise above 0.5 ng/mL, careful monitoring and tapering of exogenous insulin doses will occur.

In some embodiments, among patients with type 1 diabetes, immune therapy will be administered to protect newly formed islets prior to initiation of HIP2 and/or other peptide compounds SYMLIN® (amylin/pramlintide) hamster rNGAP, GLP-1, GLP-1 receptor agonists, GLP-1 analogs, DPP-4 inhibitors are used with (preceding, during, or following). In some embodiments, for example, the antibody hOKT3g1 (ala-ala) is administered for 12 consecutive days with its efficacy demonstrated following the first treatment out to 24 months, whereas a similar humanized monoclonal antibody, ChAglyCD3 may be administered for 6 consecutive days, then repeated yearly. In some embodiments, Diamyd's GAD65 compound is delivered in two subcutaneous injections, one month apart. In some embodiments, DIA-PEP277™ (a 24 amino acid fragment of heat shock protein 60), has demonstrated success among newly diagnosed diabetes patients utilizing a subcutaneous injections of 1 mg with 40 mg mannitol in vegetable oil at study entry, 1 month, and 6 months. In some embodiments, the cyclicity of treatment will be determined based upon the immune modulator selected. In another embodiment, DIAPEP277™ (a 24 amino acid fragment of heat shock protein 60), and IBC-VSO vaccine, which is a synthetic, metabolically inactive form of insulin designed to prevent pancreatic beta-cell destruction, interferon-alpha, or vaccination using CD4$^+$CD25$^+$ antigen-specific regulatory T cells or a similar agent is used in the combination therapy. In another embodiment, immunomodulation agents, including, but not limited to, anti-CD3 immunotherapy agents, are used in combination with HIP2. In some embodiments, such agents also include: Sirolimus (Rapamycin), Tacrolimus (FK506), DIAPEP277™) (a 24 amino acid fragment of heat shock protein 60), anti-Glutamic Acid Decarboxylase65 (GAD65) vaccine, Mycophenolate Mofetil alone or in combination with Daclizumab, the anti-CD20 agent Rituximab, Campath-1H (Anti-CD52 Antibody) and/or Vitamin D.

Some autoimmune cells target pancreatic beta cells and so play a causative role in some of the diseases and conditions treatable in accordance with the methods of the invention.

Prior methods of treatment involving the introduction of immune agents among patients with type 1 diabetes, protect only those islet cells which have yet been destroyed by immune attack and do not address to need to repopulate the pancreas with new islet structures with fully functionally beta cells. In some embodiments, methods of the present invention combine generalized and specific immune modulation aimed at reducing destruction of beta cells and a methodology of differentiating new islet cells from progenitor cells within the adult pancreas.

In some embodiments, the methods of the present invention may employ agents that specifically inhibit the activity of or block or destroy the autoimmune cells that target pancreatic beta cells that produce insulin, amylin, or glucagon. In some embodiments, such agents include immunomodulatory peptides that arrest pancreatic islet cell destruction. In some embodiments, for example, one such agent is a monoclonal antibody that can delay the progression of islet cell loss or slow or stop the onset of type 1 diabetes. In some embodiments, anti-CD3 antibodies constitute a general class of agents useful in the methods of the invention. In some embodiments, for example, suitable anti-CD3 antibodies for purposes of the present invention include the TRX4 (Ala-Ala and ChAglyCD3) antibody under development by TolerRx and the humanized anti-CD3 antibody described in the reference Herold et al., 30 May 2002, *NEJM* 346(22):1692-1698, incorporated herein by reference. In one embodiment, the humanized anti-CD3 antibody is delivered intravenously, 14 days per year in the dosage of 1-1.42 µg/kg on day 1, 5.67 µg/kg on day 2, 11.3 µg/kg on day 3, 22.6 µg/kg on day 4 and 45.4 µg/kg on days 5-14. In some embodiments, these therapies may be repeated annually following the 3-6 month usage of HIP2, while insulin is being tapered as new islet cell formation occurs. During the HIP2 treatment phase in some embodiments, Vitamin D and the usage of SYMLIN® (amylin/pramlintide) may be continued. Following the discontinuation of HIP2 and insulin therapy in some embodiments, immune modulation may be repeated annually for the anti-CD3 antibodies, though recent study has found their efficacy to continue for as long as 24 months.

In another embodiment, the immuno-modulatory compound is a heat shock protein that can arrest or slow islet cell destruction. In some embodiments, such proteins include DIAPEP277™ (a 24 amino acid fragment of heat shock protein 60) under development by Develogen AG.

In one embodiment, DIAPEP277™ (a 24 amino acid fragment of heat shock protein 60) is delivered subcutaneously by giving 1 mg in 40 mg mannitol in vegetable oil subcutaneously at baseline and at one month and then twice at 3 month intervals. In one embodiment of the combination therapy of the invention, HIP2 or a HIP2 analog or derivative is co-administered with DIAPEP277™ (a 24 amino acid fragment of heat shock protein 60) as follows. In some embodiments, the DIAPEP277™ (a 24 amino acid fragment of heat shock protein 60) is first administered subcutaneously at a dose of about 1 mg, about 30 days prior to the initiation of the HIP2 or analog or derivative-based therapy. In some embodiments, a second administration of the DIAPEP277™ (a 24 amino acid fragment of heat shock protein 60) is then made at the time (90 days after the first administration) of initiating the HIP2 or analog or derivative-based therapy.

In some embodiments, the HIP2 or analog or derivative thereof may be delivered via subcutaneous injection, orally via hepatic targeted vesicle, or other liposomal agent, or via 24 hour continuous subcutaneous infusion at a therapeutically effective dose, as described above. In one embodiment, the daily dose is about 5 to 20 mg per kg of patient body weight per 24 hours. In one embodiment, the daily dose is ~600-800 mg. In some embodiments, the HIP2 or analog or derivative-based therapy is continued for a 3-6 month period and monitored closely by C-peptide production. In some embodiments, the immune therapy will be delivered cyclically based upon the immune agent selected. In some embodiments, for example, the DIAPEP277™ (a 24 amino acid fragment of heat shock protein 60) is administered at 3 month intervals for a total of 6 months, and would initially be delivered 3 months prior to HIP2 or analog or derivative-based therapy.

In some embodiments, the immuno-modulatory agents useful in the methods of the invention can be formulated, administered, and dosed as known in the art or as described herein. Pharmaceutical formulations and additional dosing and administration protocols for practice of some embodiments of the methods of the invention are described below.

In some embodiments, compositions of HIP2 or an analog or derivative thereof, e.g., and pharmaceutically acceptable salts and esters thereof, are synergistically or additively effective to differentiate progenitor cells into new islet cells in treating diabetes or similar disorders when combined with various other compounds. In some embodiments, these compounds include HIP2 and analogs or derivatives thereof, amylin and/or an analog, including but not limited to SYMLIN® (amylin/pramlintide), GLP-1, GLP-1 receptor agonists, such as exendin-4, Liraglutide (NN2211), GLP-1 analogs, Dipeptidyl Peptidase-4 Inhibitors, GIP, hamster INGAP, and other incretin-mimetic hormones, and/or similarly acting compounds and agents, and agents that extend the half-life or increase the level or activity of any of the foregoing compounds and agents, such as, for example, dipeptidyl peptidase inhibitors, which delay the degradation of GLP-1, and agents that inhibit, block, or destroy the autoimmune cells that target beta cells including but not limited to: anti CD-3 antibodies (hOKT3γ1 Ala-Ala and ChAglyCD3), Sirolimus (Rapamycin), Tacrolimus (FK506), DIAPEP277™ (a 24 amino acid fragment of heat shock protein 60), a anti-Glutamic Acid Decarboxylase 65 (GAD65) vaccine, Mycophenolate Mofetil alone or in combination with Daclizumab, the anti-CD20 agent Rituximab, Campath-1H (Anti-CD52 Antibody), lysofylline, and Vitamin D, IBC-VSO vaccine which is a synthetic, metabolically inactive form of insulin designed to prevent pancreatic beta-cell destruction, and interferon-α vaccination using $CD4^+CD25^+$ antigen-specific regulatory T cells or a similar agent designed to prevent pancreatic beta-cell destruction. In another embodiment, interferon-α vaccination using $CD4^+CD25^+$ antigen-specific regulatory T cells or a similar agent is used in the combination therapy for utilizing regulatory T cells either directly or through the use of anti-CD3 immunotherapy.

In some embodiments, compounds such as Sirolimus (Rapamycin), Tacrolimus (FK506), TRX4 antibody, humanized anti-CD3 antibody, DYAMID™ (GADD65 vaccine) anti-GAD65 antibody, and DIAPEP277™ (a 24 amino acid fragment of heat shock protein 60) are also synergistically or additively effective when added to usage of HIP2 or an agent to differentiate progenitor cells into new islet cells in treating diabetes or similar disorders.

Synergy is defined as the interaction of two or more agents so that their combined effect is greater than the sum of their individual effects. For example, if the effect of drug A alone in treating a disease is 25%, and the effect of drug B alone in treating a disease is 25%, but when the two drugs are combined the effect in treating the disease is 75%, the effect of A and B is synergistic.

Additivity is defined as the interaction of two or more agents so that their combined effect is similar to the average of their individual effects. For example, if the effect of drug A alone in treating a disease is 25%, and the effect of drug B alone in treating a disease is 25%, but when the two drugs are combined the effect in treating the disease is about 50% or at least greater than 25%, the effect of A and B is additive.

An improvement in a drug therapeutic regimen can be obtained by the combined administration of two agents having therapeutic effect, if the interaction of the two or more agents is such that their combined effect reduces the incidence of adverse event (AE) of either or both agents used in the co-therapy. This reduction in the incidence of adverse effects can be a result of, e.g., administration of lower doses of either or both agent used in the co-therapy. For example, if the effect of drug A alone is 25% and has an adverse event incidence of 45% when used at the labeled dose; and the effect of drug B alone is 25% and has an adverse event incidence of 30% when used at the labeled dose, but when the two drugs are combined at lower than labeled doses of each, if the overall effect is 35% and the adverse incidence rate is 20%, there is an improvement in the drug therapeutic regimen. The combination therapies provided by the present invention include those exhibiting such improvements.

In some embodiments, dosing and administration of the agents useful in the methods of the invention as described herein provide accelerated islet differentiation from adult progenitor cells to optimize an individual's ability to secrete insulin from endogenous, newly formed islet structures with used in conjunction with immune therapy or therapies, which give the lowest toxicity while providing protection of the new islets from destruction. In some embodiments, pharmaceutical compositions of the invention provide for kinetic delivery of these agents, ease of delivery, and enhanced efficacy.

In one embodiment, HIP2 peptide is dosed subcutaneously or intramuscularly, at a daily dose of 0.1 to 100 mg/kg, which daily dose is subdivided and dosed four times daily, preprandially, before each meal and a dose at bedtime. In another embodiment, HIP2 peptide is dosed at a daily dose of about 5 to 25 mg/kg, which daily dose is subdivided and dosed four times daily, pre-prandially, before each meal and a dose at bedtime. In another embodiment, HIP2 peptide is dosed at a daily dose of 10 to 15 mg/kg, which dose is subdivided and delivered in four separate subcutaneous injections.

In other embodiments, the HIP2 peptide is administered only once, twice, or thrice daily, and in another embodiment, HIP2 peptide is administered by continuous infusion.

The agents useful in the methods of the invention can be administered by a variety of routes. Known agents useful in the methods of the invention can be administered by routes and using pharmaceutical formulations previously developed for other indications. Such delivery routes include, at least for most known agents, oral delivery, targeted and untargeted liposomal drug delivery systems for oral or subcutaneous delivery, which may include the hepatic-directed vesicle (AMDG/SDG) attached to HIP2 or compounds used in the methodologies described herein, topical delivery, including micelle and nanosphere topical delivery systems, subcutaneous delivery including pump-assisted continuous infusion by either intravenous or subcutaneous delivery and disposable micro-pumps and micro-needles (including but not limited to those available from Animas Corp.), and buccal delivery.

The particular route of administration and pharmaceutical formulation of an agent used in the practice of the methods of the invention will be selected by the practitioner based on a patient's disease or condition being treated and the agent employed. A wide variety of pharmaceutical compositions can be employed in the methods of the invention. In some embodiments, extended use preparations can be used for ease of administration and increased efficacy.

In one embodiment, one or more of the agents employed in the method is formulated as a micelle. In some embodiments, ease of administration is best achieved by oral delivery. While small molecule pharmaceutical agents can often be readily formulated for oral delivery, peptide and protein-based pharmaceutical agents can be more difficult to formulate for oral delivery. However, suitable formulation technology exists, and in one important aspect, the present invention provides pharmaceutical compositions of proteins and peptides formulated for oral delivery. In one embodiment, the pharmaceutical compositions useful in the methods of the invention suitable for oral delivery are formulated generally in accordance with known TECHNOSPHERE™ technology developed by MannKind Corp., ELIGEN® Technology developed by Emisphere, a nasal delivery systems developed by Nastech, an oral liposome with specificity to the liver (HDV) developed by AMDG/SDG.

Other oral delivery and encapsulation technology suitable for use in making the pharmaceutical compositions of some embodiments of the invention includes the hepatic delivery vesicle (HDV). In some embodiments, pancreatic delivery vesicle (PDV) technology may be used in accordance with the methods of the invention to prepare pharmaceutical formulations of the invention containing HIP2 or HIP2 in combination with GLP-1 for delivery of HIP2 directly to the pancreas. In some embodiments, HDV technology can be used to deliver compounds directly to the liver, and the present invention provides pharmaceutical compositions of HIP2 optionally in combination with GLP-1 in HDV liposomes targeted directly to the liver.

In some embodiments, agents that can be formulated for oral delivery and employed in the methods of the invention include HIP2 or an analog or derivative thereof, SYMLEN® (amylin/pramlintide), Exendin-4, Liraglutide (NN2211), GLP-1 receptor agonists, GLP-1, GLP-1 analogs, hamster INGAP and its analogs, GIP, Dipeptidyl peptidase-4 inhibitors and peptide and proteins or non-peptidic mimetics with similar action or homology to the preceding agents. In some embodiments, these agents can be used in accordance with the methods of the invention with monoclonal antibodies and other specific and general immune agents designed to delay the progression of beta cell loss or prevent the onset of type 1 diabetes in both children and adults. In some embodiments, these include, but are not limited to, anti CD-3 antibodies (hOKT3γ1(Ala-Ala and ChAglyCD3) that target the immune response and specifically block the T-lymphocytes that cause islet cell death in type 1 diabetes, as well as Sirolimus (Rapamycin), Tacrolimus (FK506), a heat-shock protein 60 (DIA-PEP277™) (a 24 amino acid fragment of heat shock protein 60), an anti-Glutamic Acid Decarboxylase 65 (GAD65) vaccine, Mycophenolate Mofetil alone or in combination with Daclizumab, the anti-CD20 agent, Rituximab, Campath-1H (Anti-CD52 Antibody), lysofylline, Vitamin D, IBC-VSO vaccine which is a synthetic, metabolically inactive form of insulin designed to prevent pancreatic beta-cell destruction, interferon-alpha vaccination using $CD4^+CD25^+$ antigen-specific regulatory T cells or similar agents. In some embodiments, these agents are used in the combination therapies of the invention to utilize regulatory T cells either directly or through the use of immunotherapy to arrest the destruction of insulin-producing cells.

In some embodiments, the invention further relates to kits for treating patients having type 1 or type 2 diabetes or other glucose metabolism disorders in children and adults including pre-diabetes, impaired fasting glucose, insulin resistant syndromes, the metabolic syndrome, obesity, overweight, polycysistic ovarian syndrome, hyperlipidemia, hypertriglyceridemia comprising one or more therapeutically effective methods of HIP2 or an analog or derivative modes of treatment thereof. Optionally, the kit may also contain other agents as described above for use in the combination therapies of the invention, either in the same or separate packaging, and instructions for use.

As exemplified by the preceding paragraph, some embodiments of the present invention provide kits for treating a disease or condition associated with impaired pancreatic function in a subject in need thereof, comprising: a therapeutically effective amount of HIP2 in a first dosage unit; optionally a therapeutically effective amount of one or more immune therapies; optionally a therapeutically effective amount of one or more additional agents that stimulate islet cell regeneration in a third dosage unit; and instructions for use.

Any techniques known in the art can be used in synthesizing and purifying HIP2 or an analog or derivative thereof, including, but not limited to, de novo chemical synthesis and purification by precipitation, adsorption (e.g., column chromatography, membrane adsorbents, radial flow columns, batch adsorption, high-performance liquid chromatography, ion exchange chromatography, inorganic adsorbents, hydrophobic adsorbents, immobilized metal affinity chromatography, affinity chromatography), or gel filtration, electrophoresis, liquid phase partitioning, detergent partitioning, organic solvent extraction, and ultrafiltration. During purification, the biological activity of HIP2 or an analog or derivative thereof may be monitored by one or more in vitro or in vivo assays. The purity of HIP2 or an analog or derivative thereof can be assayed by any methods known in the art, such as but not limited to, gel electrophoresis. See Scopes, supra. In some embodiments, HIP2 or an analog or derivative thereof employed in a composition of the invention can be in the range of 80 to 100 percent of the total mg protein, or at least 80%, at least 85%, at least 90%, at least 95%, or at least 98% of the total mg protein. In one embodiment, HIP2 or an analog or derivative thereof employed in a composition of the invention is at least 99% of the total protein. In another embodiment, HIP2 or an analog or derivative thereof is purified to apparent homogeneity, as assayed, e.g., by sodium dodecyl sulfate polyacrylamide gel electrophoresis. In one embodiment, HIP2 is synthesized and tested by HPLC to a purity greater than 95%.

Methods known in the art can be utilized to produce HIP2 or an analog or derivative thereof recombinantly. A nucleic acid sequence encoding HIP2 or an analog or derivative thereof can be inserted into an expression vector for propagation and expression in host cells.

An expression construct, as used herein, refers to a nucleic acid sequence encoding a HIP2 or an analog or derivative thereof operably associated with one or more regulatory regions that enable expression of HIP2 or an analog or derivative thereof in an appropriate host cell. "Operably-associated" refers to an association in which the regulatory regions and the HIP2 or an analog or derivative thereof to be expressed are joined and positioned in such a way as to permit transcription, and ultimately, translation.

In some embodiments, the regulatory regions that are necessary for transcription of HIP2 or an analog or derivative thereof can be provided by the expression vector. In some embodiments, a translation initiation codon (ATG) may also be provided if a HIP2 or an analog or derivative thereof gene sequence lacking its cognate initiation codon is to be expressed. In a compatible host-construct system, cellular transcriptional factors, such as RNA polymerase, will bind to the regulatory regions on the expression construct to effect transcription of the HIP2 sequence in the host organism. The precise nature of the regulatory regions needed for gene expression may vary from host cell to host cell. Generally, a promoter is required which is capable of binding RNA polymerase and promoting the transcription of an operably-associated nucleic acid sequence. Such regulatory regions may include those 5' non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites.

In some embodiments, in order to attach DNA sequences with regulatory functions, such as promoters, to a HIP2 or an analog or derivative thereof gene sequence or to insert a HIP2 or an analog or derivative thereof gene sequence into the cloning site of a vector, linkers or adapters providing the appropriate compatible restriction sites may be ligated to the ends of the cDNAs by techniques well known in the art. In some embodiments, cleavage with a restriction enzyme can be followed by modification to create blunt ends by digesting back or filling in single-stranded DNA termini before ligation. Alternatively, a desired restriction enzyme site can be introduced into a fragment of DNA by amplification of the DNA using PCR with primers containing the desired restriction enzyme site.

An expression construct comprising a HIP2 or an analog or derivative thereof sequence operably associated with regulatory regions can be directly introduced into appropriate host cells for expression and production of a HIP2 or an analog or derivative thereof without further cloning. The expression constructs can also contain DNA sequences that facilitate integration of a HIP2 or an analog or derivative thereof sequence into the genome of the host cell, e.g., via homologous recombination. In this instance, it is not necessary to employ an expression vector comprising a replication origin suitable for appropriate host cells to propagate and express HIP2 or an analog or derivative thereof in the host cells.

A variety of expression vectors may be used, including but not limited to, plasmids, cosmids, phage, phagemids or modified viruses. Such host-expression systems represent vehicles by which the coding sequences of a HIP2 or an analog or derivative thereof gene may be produced and subsequently purified, but also represent cells which may, when transformed or transfected with the appropriate nucleotide coding sequences, express HIP2 or an analog or derivative thereof in situ. These include, but are not limited to, microorganisms such as bacteria (e.g., *E. coli* and *B. subtilis*) transformed with recombinant bacteriophage DNA, plasmid DNA or cosmid DNA expression vectors containing HIP2 or an analog or derivative thereof coding sequences; yeast (e.g., *Saccharomyces, Pichia*) transformed with recombinant expression vectors containing HIP2 or an analog or derivative thereof coding sequences; insect cell systems infected with recombinant virus expression vectors (e.g., baculovirus) containing HIP2 or an analog or derivative thereof coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing HIP2 or an analog or derivative thereof coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli* and eukaryotic cells are used for the expression of a recombinant HIP2 or an analog or derivative thereof. For example, mammalian cells such as Chinese hamster ovary cells (CHO) can be used with a vector bearing promoter element from major intermediate early gene of cytomegalovirus for effective expression of a HIP2 or an analog or derivative thereof sequence.

In bacterial systems, a number of expression vectors may be advantageously selected depending upon the use intended for the HIP2 or an analog or derivative thereof being expressed. For example, when a large quantity of a HIP2 or an analog or derivative thereof is to be produced, for the generation of pharmaceutical compositions of a HIP2 or an analog or derivative thereof, vectors that direct the expression of high levels of fusion protein products that are readily purified may be desirable. Vectors include, but are not limited to, the *E. coli* expression vector pCR2.1 TOPO (Invitrogen); pIN vectors, and the like. Series of vectors like pFLAG (Sigma), pMAL (NEB), and pET (Novagen) may also be used to express the foreign proteins as fusion proteins with FLAG peptide, malE-, or CBD-protein. These recombinant proteins may be directed into periplasmic space for correct folding and maturation. The fused part can be used for affinity purification of the expressed protein. Presence of cleavage sites for specific proteases like enterokinase allows one to cleave off the HIP2 or an analog or derivative thereof. The pGEX vectors may also be used to express foreign proteins as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, many vectors to express foreign genes can be used, e.g., *Autographa californica* nuclear polyhedrosis virus (AcNPV) can be used as a vector to express foreign genes. The virus grows in cells like *Spodoptera frugiperda* cells. A HIP2 or an analog or derivative thereof coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, a HIP2 or an analog or derivative thereof coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing HIP2 or an analog or derivative thereof in infected hosts. Specific initiation signals may also be required for efficient translation of inserted HIP2 or an analog or derivative thereof coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, and the like.

In addition, a host cell strain may be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript and post-translational modification of the gene product, e.g., glycosylation and phosphorylation of the gene product, may be used. Such mammalian host cells include, but are not limited to, PC12, CHO, VERY, BHK, HcLa, COS, MDCK, 293, 3T3, W138, BT483, Hs578T, HTB2, BT2O and T47D, NS0 (a murine myeloma cell line that does not endogenously produce any immunoglobulin chains), CRL7030, and HsS78Bst cells. Expression in a bacterial or yeast system can be used if post-translational modifications are found to be non-essential for a desired activity of HIP2 or an analog or derivative thereof.

For long-term, high-yield production of properly processed HIP2 or an analog or derivative thereof, stable expression in cells is preferred. Cell lines that stably express HIP2 or an analog or derivative thereof may be engineered by using a vector that contains a selectable marker. By way of example and not limitation, following the introduction of the expression constructs, engineered cells may be allowed to grow for 1-2 days in an enriched media, and then are switched to a selective media. The selectable marker in the expression construct confers resistance to the selection and may, depending on the vector construct and host cell employed, allow cells to stably integrate the expression construct into their chromosomes and to grow in culture and to be expanded into cell lines. Such cells can be cultured for a long period of time while HIP2 or an analog or derivative thereof is expressed continuously.

A number of selection systems may be used, including but not limited to, antibiotic resistance (markers like Neo, which confers resistance to geneticine, or G-418; Zeo, for resistance to Zeocin; and Bsd, for resistance to blasticidin); antimetabolite resistance; gpt, which confers resistance to mycophenolic acid; and hygro, which confers resistance to hygromycin. In addition, mutant cell lines including, but not limited to, tk–, hgprt– or aprt– cells, can be used in combination with vectors bearing the corresponding genes for thymidine kinase, hypoxanthine, guanine- or adenine phosphoribosyl-transferase. Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); Chapters 12 and 13, Dracopoli et al. (eds), of Current Protocols in Human Genetics, John Wiley & Sons, NY (1994); and Colberre-Garapin et al., 1981, J. Mol. Biol. 150:1.

The recombinant cells may be cultured under standard conditions of temperature, incubation time, optical density and media composition. However, conditions for growth of recombinant cells may be different from those for expression of HIP2 or an analog or derivative thereof. Modified culture conditions and media may also be used to enhance production of HIP2 or an analog or derivative thereof. Any techniques known in the art may be applied to establish the optimal conditions for producing HIP2 or an analog or derivative thereof.

An alternative to producing HIP2 or a fragment thereof by recombinant techniques or purification from natural sources is peptide synthesis. For example, an entire HIP2 or an analog or derivative thereof, or a protein corresponding to a portion of HIP2 or an analog or derivative thereof, can be synthesized by use of a peptide synthesizer. Conventional peptide synthesis or other synthetic protocols well known in the art may be used.

Proteins having the amino acid sequence of HIP2 or an analog or derivative thereof or a portion thereof may be synthesized by solid-phase peptide synthesis using procedures similar to those described by Merrifield, 1963, J. Am. Chem. Soc, 85:2149. During synthesis, N-α-protected amino acids having protected side chains are added stepwise to a growing polypeptide chain linked by its C-terminal and to an insoluble polymeric support, i.e., polystyrene beads. The proteins are synthesized by linking an amino group of an N-α-deprotected amino acid to an α-carboxyl group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc, which is acid labile, and Fmoc, which is base labile. Details of appropriate chemistries, resins, protecting groups, protected amino acids and reagents are well known in the art and so are not discussed in detail herein.

Purification of the resulting HIP2 or an analog or derivative thereof is accomplished using conventional procedures, such as preparative HPLC using gel permeation, partition and/or ion exchange chromatography. The choice of appropriate matrices and buffers are well known in the art and so are not described in detail herein.

The embodiments of the methods described above can be combined in any manner. Thus, features from one embodiment can be combined with features from any other embodiment. Further, various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

With the foregoing detailed description of the reagents and methods of the invention, the following Examples are provided to illustrate various aspects of the invention.

Example 1

HIP2, HIP1, HIP, controls and progenitor fractions were cultured over 10 days, according to standard protocol. Briefly, pancreata from adult human cadaveric organ donors were obtained through the local organ procurement organization. Islets were isolated according to established protocols described by Bonner-Weir and Jamal. (Bonner-Weir et al., *Pediatric Diabetes:*2004; 5 (Suppl 2): 16-22. Jamal et al., *Cell Death Differ.* 2005 July; 12(7): 702-12).

Briefly, following removal of the organ, cold ischemia time was no more than 8 hours prior to islet isolation. The main pancreatic duct was cannulated and perfused with Liberase HI (Roche Diagnostics). The perfused organ was placed in a closed system (Ricordi Apparatus) and heated to 37° C. to activate the enzyme blend. Following the appearance of free islets in samples, the system was cooled and free tissues were collected and washed. Tissues were applied to a continuous density gradient created using Ficoll (Biochrom KG) in a cell processor (COBE). Free islets with diameters ranging from 75 to 400 μm, determined to be greater than 90% pure by staining with dithizone (Sigma) a zinc chelater, were collected and washed. IHC to detect the presence of amylase and cytokeratin was negative, consistent with the absence of progenitor and exocrine tissue. The progenitor fraction from this separation was also collected for culture.

Isolated islets were embedded in a type 1 collagen matrix at a density of 2000 islet equivalents/25 cm$^2$ and cultured in DMEM/F12 containing 10% FBS, 1 μM dexamethasone, 10 ng/ml EGF, 24 mU/ml insulin and 100 ng/ml cholera toxin.

Medium was changed every other day. On day 10, culture was continued in the above medium, without the cholera toxin, with HIP2, HIP, HIP1 and INGAP in concentrations of 1.0 uM and 3.3 uM into 2 ml cultures for final concentrations of 500 nM, 167 nM and 50 nM. Medium was changed every other day. Collagen-embedded cultures were harvested by incubating with 0.25 g/L collagenase XI (Sigma) for 30 minutes at 37° C.

After culture, the human pancreatic islet and progenitor fractions were then treated in a blinded study with either HIP2, HIP, HIP 1, the hamster INGAP sequence as a positive control (SEQ ID NO:1) or a scrambled peptide sequence that was synthesized by Bachem Bioscience (95% pure, research grade) (SEQ ID NO:5). Duplicate cultures were treated on Day 10 and Day 12 and then lysed for detection of insulin content on Day 14. During 10 day culture, the insulin production decreases to negligible amounts and, after treatment with peptides, insulin is produced again.

Figure 2:
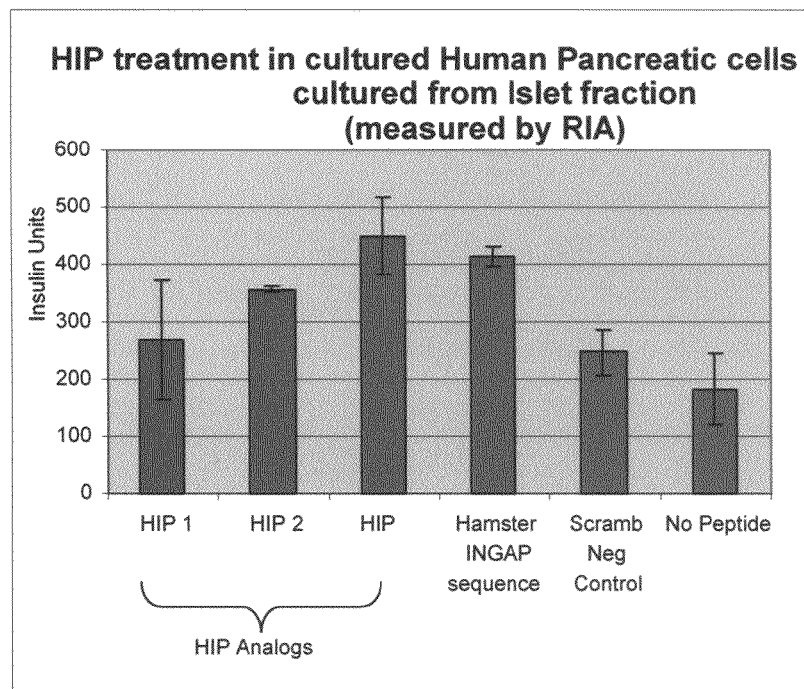
FIG. 2 is a bar graph showing increased insulin production in human pancreatic islet tissue after treatment with HIP analogs, as compared with similar treatment with SEQ ID NO:1 and SEQ ID NO:5.
Figure 4:
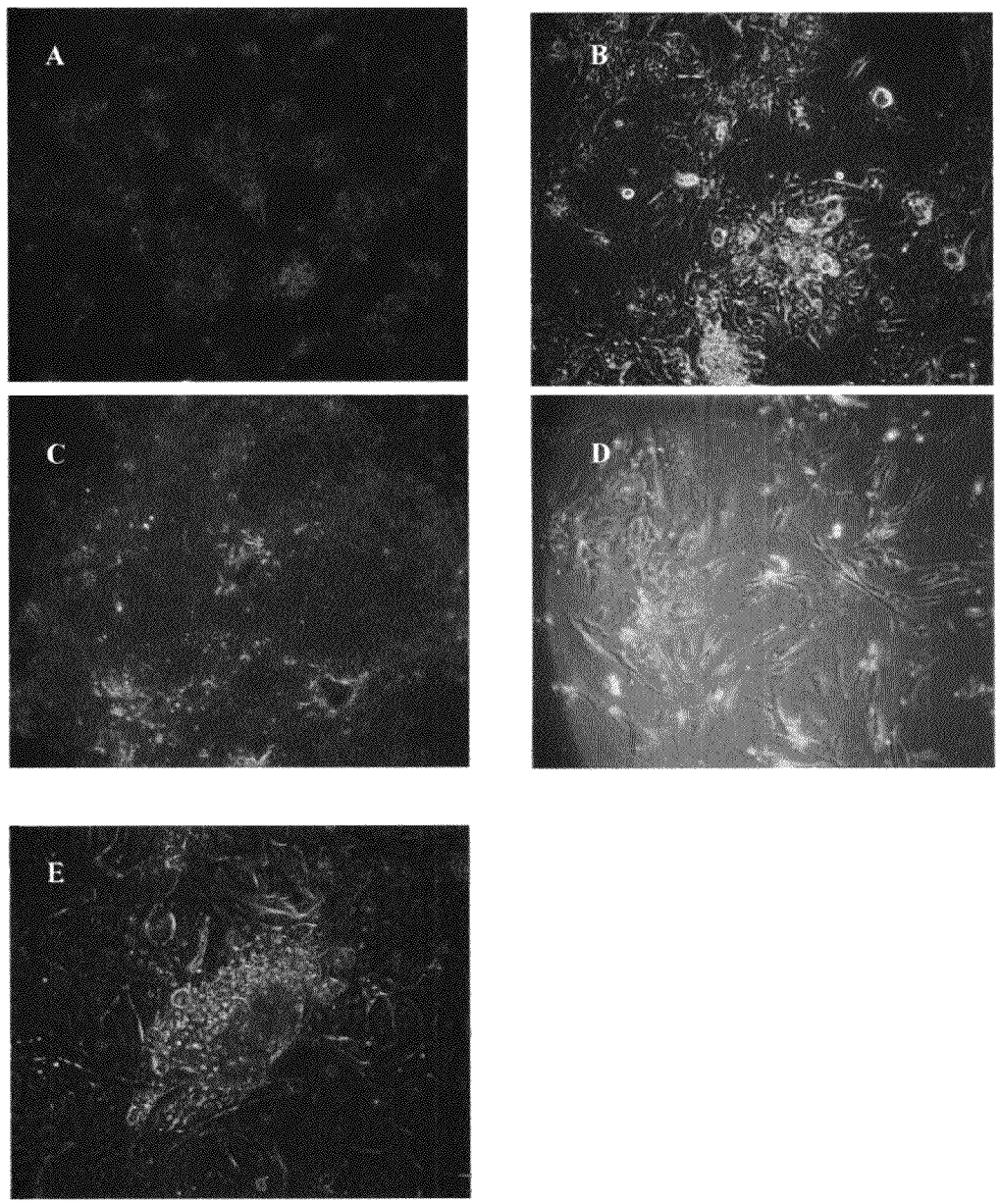
FIG. 4A shows a micrograph of a pancreatic ductal tissue fraction culture after six days of culture with SEQ ID NO:4. New islet structure has formed within the cell culture.
FIG. 4B shows a micrograph of a pancreatic ductal tissue fraction culture without culture with SEQ ID NO:4.
FIG. 4C shows a micrograph of a higher magnification micrograph of the micrograph shown in FIG. 4A.
FIG. 4D shows a micrograph of a 10 day culture of ductal tissue fraction culture not treated with SEQ ID NO:4.
FIG. 4E shows a micrograph of a 10 day culture of ductal tissue fraction culture treated with SEQ ID NO:4.

Insulin levels were detected by Radioimmunoassay (RIA) from cultures treated with saline only, scrambled peptide, HIP2, HIP1, HIP and hamster INGAP. The results for human ductal tissue fraction are shown in FIG. 1 and for human islet tissue in FIG. 2. Both fractions contain progenitor cells, which are the nidus for new islet structures and upon which HIP peptides exerts stimulatory effect. FIG. 4 shows the ductal tissue culture fraction after HIP2 treatment, just before lysis and measurement by RIA. Morphological changes show islet like structure. Consistently, greater induction of new islets is observed from the cells cultured from the ductal fraction of the pancreatic tissue. This observation is consistent with the notion that fewer progenitor cells are among the islet tissue fraction after the isolation process.

Example 2

HIP2, HIP1, HIP, controls and progenitor fractions were cultured over 10 days, according to standard protocol. Briefly, pancreata from adult human cadaveric organ donors were obtained through the local organ procurement organization. Islets were isolated according to established protocols described by Bonner-Weir and Jamal. (Bonner-Weir et al. *Pediatric Diabetes:* 2004; 5 (Suppl 2): 16-22. Jamal et al. *Cell Death Differ.* 2005 July; 12(7): 702-12). HIP2, HIP1, HIP and INGAP were synthesized by Bachem Bioscience, Malvern, Pa. and were quality tested by HPCL to be greater than 95% pure. Each peptide was provided in lyophilized powder and was resuspended in isotonic saline solution. Stock solutions were made so that only 1-2 ul aliquots were added to primary cell cultures to reach the final concentrations provided below. Stock solutions were frozen and thawed a total of three times for the six day treatment. HPLC data confirmed that the peptides remained stable in the isotonic saline after the freeze/thaw cycles.

Pancreata from adult human cadaveric organ donors were obtained through the local organ procurement organization. Islets were isolated according to established protocols. Briefly, following removal of the organ, cold ischemia time was no more than 8 hours prior to islet isolation. The main pancreatic duct was cannulated and perfused with Liberase HI (Roche Diagnostics). The perfused organ was placed in a closed system (Ricordi Apparatus) and heated to 37° C. to activate the enzyme blend. Following the appearance of free islets in samples, the system was cooled and free tissues were collected and washed. Tissues were applied to a continuous density gradient created using Ficoll (Biochrom KG) in a cell processor (COBE). Free islets with diameters ranging from 75 to 400 µm, determined to be greater than 90% pure by staining with dithizone (Sigma) a zinc chelator, were collected and washed. IHC to detect the presence of amylase and cytokeratin was negative, consistent with the absence of progenitor and exocrine tissue. The progenitor fraction from this separation was also collected for culture.

In an effort to grow less differentiated cells, isolated islets were embedded in a type 1 collagen matrix at a density of 2000 islet equivalents/25 cm$^2$ and cultured in DMEM/F12 containing 10% FBS, 1 µM dexamethasone, 10 ng/ml EGF, 24 mU/ml insulin and 100 ng/ml cholera toxin. In an effort to promote the death of more differentiated cells, TNF-α was added to cultures to stimulate nitric oxide induced apoptosis and hydro colloid dextran was added to cultures to disrupt cell adhesions. Finally, calcium levels were limited to 0.001-0.9 mM. Finally, calcium levels were limited to 0.001-0.9 mM.

Medium was changed every other day. On day 10, cultures were continued in their medium, without the cholera toxin, and with the addition of one of the following peptides HIP2, HIP, HIP1 and INGAP in concentrations of 1.0 µM and 3.3 µM into 2 ml cultures for final concentrations of 500 nM, 167 nM and 50 nM. Medium was changed every other day. Collagen-embedded cultures were harvested by incubating with 0.25 g/L collagenase XI (Sigma) for 30 minutes at 37° C.

After culture, the human pancreatic islet and progenitor fractions were then treated in a blinded study with either HIP2, HIP, HIP1, the hamster INGAP sequence as a positive control (SEQ ID NO:1) or isotonic saline only (s/0). Duplicate cultures were treated on Day 10 and Day 12 and then lysed for detection of insulin content on day 14. During 10 day culture, the insulin production decreases to negligible amounts and, after treatment with peptides, insulin is produced again.

Figure 3:
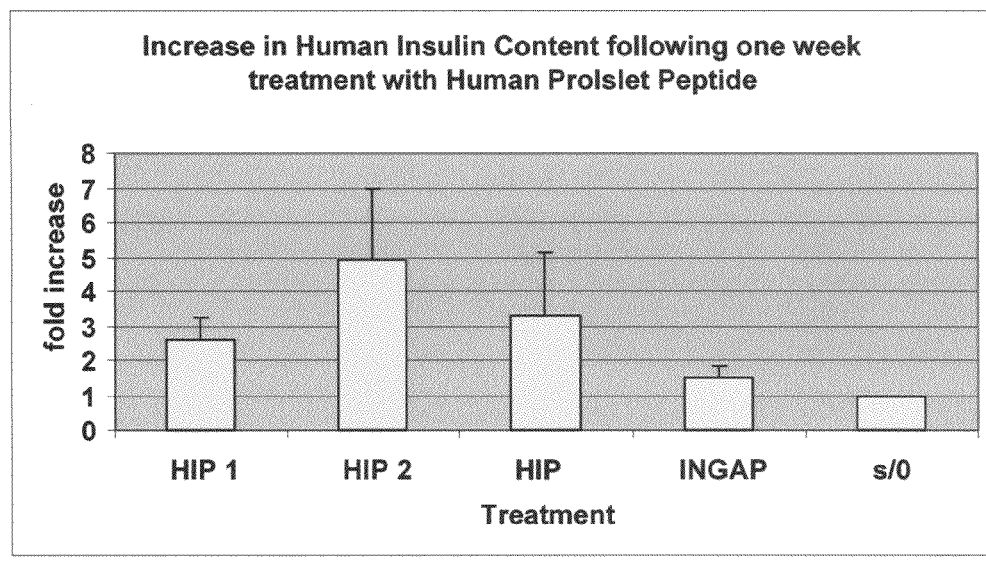
FIG. 3 is a bar graph showing increased insulin content observed following treatment with HIP analogs, compared with similar treatment with SEQ ID NO: 1 and a negative control.

Insulin levels were detected by Radioimmunoassay (RIA) from cultures treated with saline only (s/0), HIP2, HIP1, HIP and hamster INGAP. The results are shown in FIG. 3. Results here indicate that the human cell cultures (here mixed with islets and ductal tissue cultures as prepared as in Example 1) are somewhat more stimulated by the human homologs than the native hamster sequence. Specifically, the results indicate that HIP2 demonstrates an increased bioactivity (1.50-3.33 fold increase) over the other agents used in this experiment.

Example 3

Figure 5:
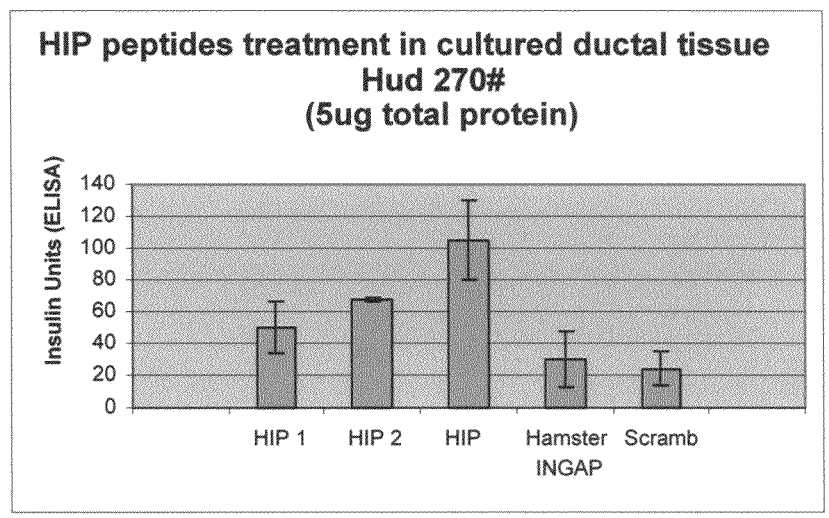
FIG. 5 is a bar graph showing increased insulin production in human pancreatic ductal tissue cultures treated with HIP2 after 10 days according to the Rosenberg protocol. This graph shows the results of treatment with SEQ ID NO:4, as compared with similar treatment with SEQ ID NO:1 and SEQ ID NO:5. Samples are 5 μg total protein in duplicate and measured by ELISA assay.
Figure 6:
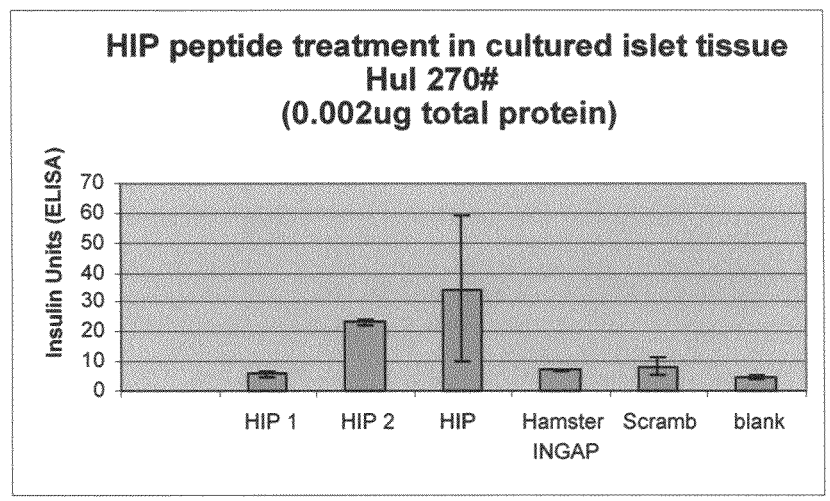
FIG. 6 is a bar graph showing increased insulin production in human pancreatic islet tissue cultures treated with HIP2 after 10 days according to the Rosenberg protocol. This graph shows the results of treatment with SEQ ID NO:4, as compared with similar treatment with SEQ ID NO:1 and SEQ ID NO:5. Samples are 0.002 μg total protein in duplicate and measured by ELISA assay.
Figure 8:
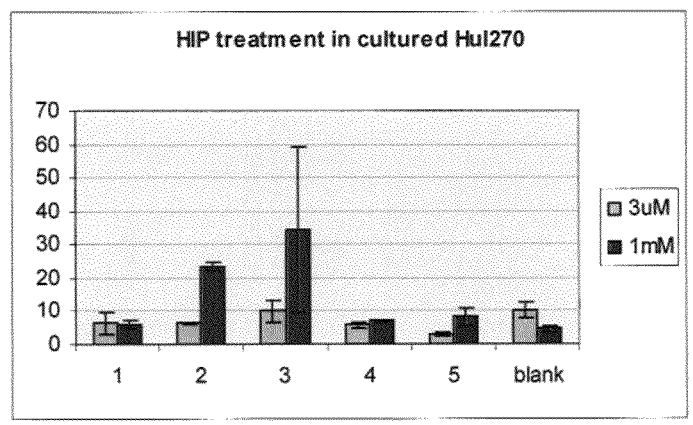
FIG. 8A is a bar graph showing increased insulin production in human pancreatic islet tissue cultures treated with two concentrations of HIP2. This graph shows the results of treatment with SEQ ID NO:4, as compared with similar treatment with SEQ ID NO:1 and SEQ ID NO:5. Values are mean insulin units (of duplicate samples) as measured by ELISA assay.
FIG. 8B is a bar graph showing increased insulin production in human pancreatic ductal tissue cultures treated with two concentrations of HIP2. This graph shows the results of treatment with SEQ ID NO:4, as compared with similar treatment with SEQ ID NO:1 and SEQ ID NO:5. Values are mean insulin units (of duplicate samples) as measured by ELISA assay.
Figure 8:
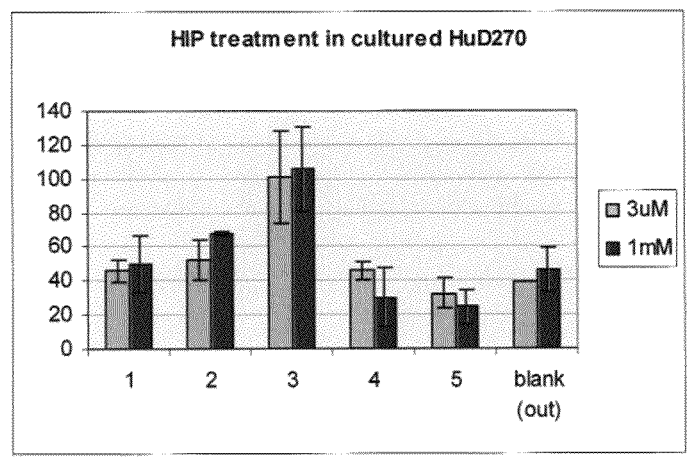
Figure 9:
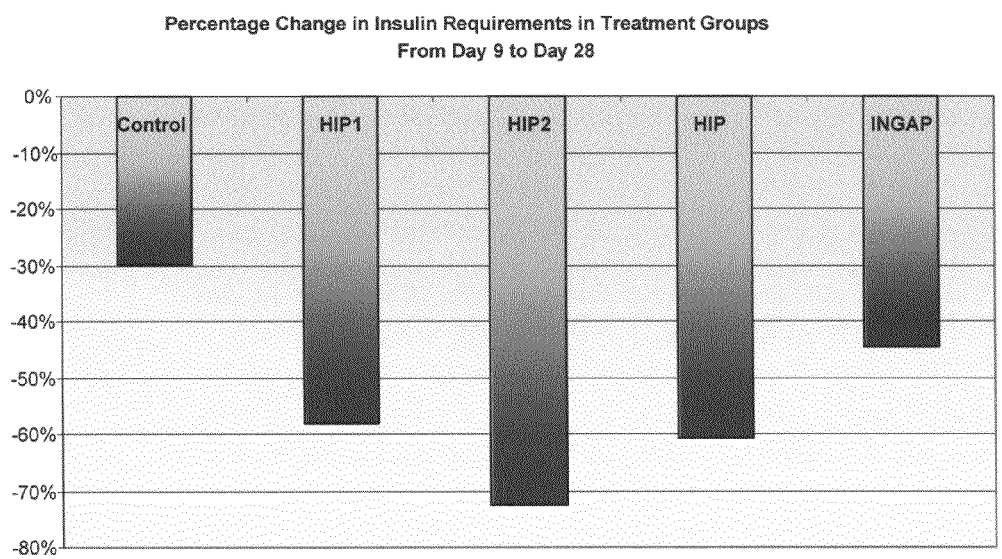
FIG. 9 is a graph depicting the insulin requirements in mice rendered diabetic with streptozocin and treated with HIP1, HIP2, HIP3, and hamster INGAP.

Human pancreatic tissue was treated as described in Example 1 and Insulin production was measured by ELISA assay. FIGS. 5 and 6 show the results of this experiment to show a dose response and to again compare the effect of HIP2 on the two different fractions of tissue as compared to the hamster INGAP sequence and a scrambled negative peptide sequence. Lane 1 shows results from Hud 270 cells human ductal cells isolated as described in Example 1, treated with HIP2. Lane 2 shows cells treated with a peptide with the INGAP sequence (SEQ ID NO: 1). Lane 3 shows cells treated with a scrambled peptide (SEQ ID NO:5). The results in FIG. 5 were generated using 5 µg of each peptide, while the results in FIG. 6 were acquired using 0.002 µg of each peptide. FIG. 8A shows results for cells cultured from the islet fraction and treated with 3 µM and 1 mM of each peptide, while FIG. 8B shows results for cells cultured from the ductal fraction and treated with 3 µM and 1 mM of each peptide.

In each of the examples, HIP2 induced insulin production more effectively than INGAP or scrambled peptide, and the higher concentration of HIP2 produced a more profound effect in ductal cultures in which progenitor cells are more concentrated. In the islet cultures, the limiting factor for the degree to which the cultures are able to produce more insulin is not the concentration of the peptide, but the number of progenitor cells per culture.

Example 4

Figure 7:
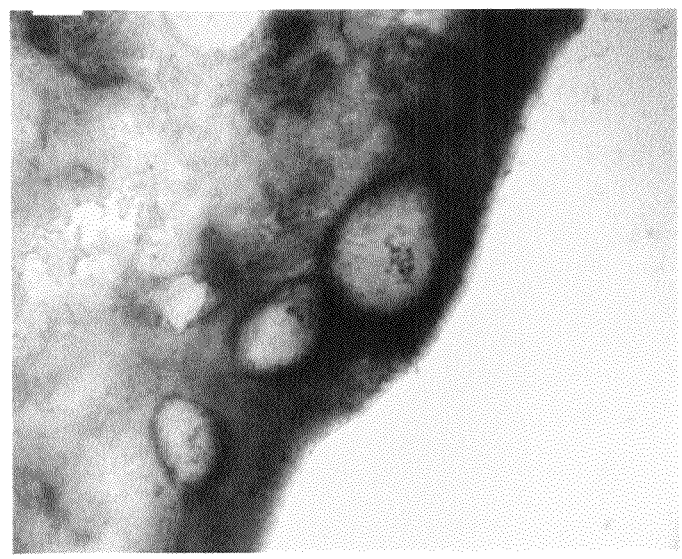
FIG. 7A is an inverted micrograph showing human pancreatic progenitor cells, forming a nidus of new insulin producing islets after two days of treatment with HIP.
FIG. 7B is an inverted micrograph showing human pancreatic progenitor cells forming insulin producing islet like structure after six days of treatment with HIP.
Figure 7:
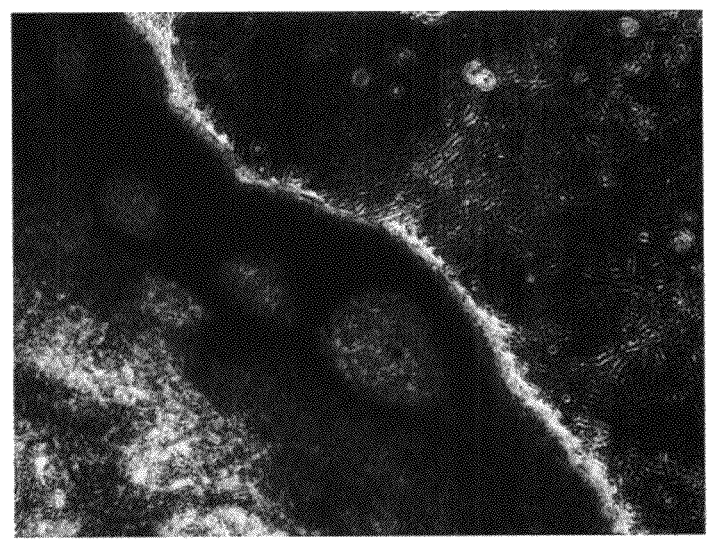

A human ductal tissue fraction was isolated and cultured as described in Example 1. After 10 days of culture, cells were treated with HIP2 for four days and observed using inverted microscopy. FIGS. 4A, 4B, and 4C shows cultures treated with HIP2, and 4D shows the negative control ductal tissue treated with no peptide. FIG. 7A shows human pancreatic progenitor tissue cultures at day 12 (day 2 of treatment with HIP2). Islets have formed what has previously been described as ductal epithelial cysts and are starting to bud at one end where a progenitor cell resides. FIG. 8B shows human pancreatic progenitor tissue cultures at day 18 (day 6 of treatment with HIP2). In this panel, the darkening of the budding portion of the ductal epithelial cyst indicates the differentiation of cells consistent with previously shown changes that occur with hamster INGAP treatment in vitro.

Example 5

The non-obese diabetic (NOD) mouse strain has long been studied as an excellent model of type 1 diabetes because it spontaneously develops a disease that is very similar to the human condition. Diabetes in NOD mice is mediated by inflammatory autoreactive T cells that recognize pancreatic islet antigens and escape central and peripheral tolerance. In a parental colony of NOD mice, incidence of diabetes in female NOD mice is typically 75-90% by 30 weeks but may exceed 90% in some cohorts. In this example, 50 female NOD mice, ranging from 13-14 weeks old at the outset of the study, are used to test the effectiveness of HIP2 as compared to other test agents. Due to the unexpected variability of the degree of onset of disease, the number used in this example (50 female mice) is considered to be the minimum needed to result in a sufficient number of mice that will onset with disease within the timeframe of the study.

Animals were group housed in compliance with the National Research Council "Guide for the Care and Use of Laboratory Animals". The animals received 12 hours light/12 hours dark, except when room lights were turned on during the dark cycle to accommodate study procedures. Room temperature was maintained between 18 to 26° C. at all times. Relative humidity was maintained between 30-70% at all times. All animals were given access to Harlan Teklad Rodent Diet or equivalent and tap water via water bottle. Animals were allowed to acclimate to their new environment for a minimum of 7 days prior to first dosing.

Procedure.

Mice were randomly divided and assigned to study groups. Each study group was assigned treatment with one of 5 test agents (see Treatment section below). Prior to being treated, each mouse was tested for diabetes via monitoring their blood glucose levels. After confirmation that the mice were diabetic (blood glucose levels greater than 16.7 mmol/L (300 mg/dL) for two consecutive days), the mice were dosed.

Treatment.

Each study group received doses of one of the following test agents: HIP2, HIP1, HIP, Hamster INGAP (SEQ ID NO:1) or isotonic saline "Vehicle" (0.9% NaCl) (negative control). Mice were given doses of their respective agent interperitoneally twice daily (am and pm, +/−2 hours for each administration) at 250 ug/dose, in 100 ul dose volume, for 28 consecutive days. Test agents were prepared once daily by dissolving the appropriate amount of test agent in isotonic saline to result in a 2.5 mg/ml solution. Concurrent to the treatment of the test agent, the mice were treated with an immunosuppressant (anti-CD3 antibody) at 5 ug/day intravenously for 5 consecutive days. Blood glucose levels were tested every 3 days, at the same time each day, using a glucometer. If the blood glucose level in any animal became too high, the animal was treated with insulin. At the end of the treatment, all surviving animals were euthanized by $CO_2$ asphyxiation following terminal blood collection. Blood samples were collected under $CO_2$ cardiocentesis. The plasma was separated and then frozen at −80° C. For histological analysis, the pancreas from each mouse was removed and snap-frozen.

Study Assessment.

Blood glucose levels are measured every 3 days and tracked to evaluate differences in glucose levels.

a. Results: NOD mice taking HIP2 display a pronounced reduction in blood glucose levels and decreased showing of insulinitis in their pancreases as compared to the NOD mice taking the other test agents.

Example 6

The streptozocin-induced diabetic mouse is a convenient animal model of type 1 diabetes because researchers are able to chemically induce diabetes under controlled conditions rather than waiting for mice to become diabetic naturally or by forcing diabetes through prescribed obesity. Based on experience with the streptozocin model in the rat, a high degree of variability was anticipated for the induction of the disease in mice and therefore 60 mice were induced with streptozocin. Mice were injected intraperitoneally with streptozocin at 40 mg/kg in citrate buffer, pH4.5, on 5 consecutive days in an attempt to render them diabetic. A mouse was considered diabetic once its blood glucose level was greater than 16.7 mmol/L (300 mg/dL) for at least 1 week. If the blood glucose level of any animal became too high (>400 mg/dL) the animal was treated with an effective amount of insulin. In this example, 60 male mice, ranging from 6-8 weeks old at the outset of the study, were treated with streptozocin as described above. Those mice that were declared diabetic were then used to test the effectiveness of HIP2 as compared to other test agents.

Animals were group housed in compliance with the National Research Council "Guide for the Care and Use of Laboratory Animals". The animals received 12 hours light/12 hours dark, except when room lights were turned on during the dark cycle to accommodate study procedures. Room temperature was maintained between 18 to 26° C. at all times. Relative humidity was maintained between 30-70% at all times. All animals were given access to Harlan Teklad Rodent Diet or equivalent and tap water via water bottle. Animals were allowed to acclimate to their new environment for a minimum of 7 days prior to first dosing.

Procedure.

Mice were randomly divided and assigned to study groups. Each study group was assigned treatment with one of 5 test agents (see Treatment section below). Prior to being treated, each mouse was tested for diabetes via monitoring their blood glucose levels. After confirmation that the mice were diabetic (blood glucose levels greater than 16.7 mmol/L (300 mg/dL) for at least 1 week) the mice were dosed with their respective test agent.

Treatment.

Each study group received doses of one of the following test agents: HIP2, HIP1, HIP, Hamster INGAP (SEQ ID NO:1) or isotonic saline "Vehicle" (0.9% NaCl) (negative control). Mice were given doses of their respective agent interperitoneally twice daily (am and pm, +/−2 hours for each administration) at 250 ug/dose, in 100 ul dose volume, for 28 consecutive days. Test agents were prepared once daily by dissolving the appropriate amount of test agent in isotonic saline to result in a 2.5 mg/ml solution. Blood glucose levels were tested every 3 days, at the same time each day, using a glucometer. If the blood glucose level in any animal became too high, the animal was treated with insulin. At the end of the treatment, all surviving animals were euthanized by CO2 asphyxiation following terminal blood collection. Blood samples were collected under CO2 cardiocentesis. The plasma was separated and then frozen at −80° C. For histological analysis, the pancreas from each mouse was removed and snap-frozen.

Study Assessment.

Blood glucose levels are measured every 3 days and tracked to evaluate differences in glucose levels.

a. Results: Streptozocin-induced diabetic mice taking HIP2 display a pronounced reduction in blood glucose levels and decreased showing of insulinitis in the pancreas as compared to the streptozocin-induced diabetic mice taking the other test agents.

Although the present invention has been described in detail with reference to specific embodiments, those of skill in the art will recognize that modifications and improvements are within the scope and spirit of the invention, as set forth in the claims which follow. All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

Significant reductions in both the insulin requirements and the rate of decrease in insulin requirements were seen among all HIP2-treated mice. The HIP2 treated mice were completely insulin-free by day 21. There was a significant reduction in mean insulin requirements among HIP-treated mice compared to placebo. Overall insulin requirements were 32% lower in the HIP-treated group and 14% lower in the INGAP treated groups compared to controls.

There was also a significant reduction in HIP2-treated mice in glucose levels from baseline compared with control. There was a 9.5% reduction in mean glucose in the placebo group, a mean reduction in glucose in the HIP treatment groups of 26.9% and hamster-derived INGAP demonstrated a 20% reduction in glucose.

Example 7

Quantitative immunohistochemistry image analysis of the pancreata of the placebo controlled and HIP treated mice showed total islet mass of the HIP treated group was 153% greater (p=0.05) than total islet mass of the placebo group. The islet mass of the placebo group was 854,362 μm (2) compared with 2,161,782 μm (2) in HIP-treated mice. While the islet sizes between the two groups were not statistically different, the number of islets counted in the pancreata of the HIP treatment groups was 62% greater than the placebo group (p=0.022) with 280 islets counted in the placebo group compared to 454 in the HIP-treated group.

This data supports the hypothesis that production is not resulting from increased stimulation of insulin production or beta cell proliferation, but a function of increased islet number supporting the proposed mechanism that HIP stimulates new islet formation.

Figure 11:
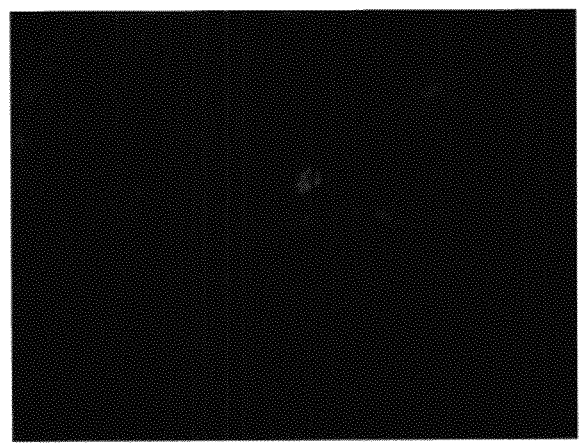
FIG. 11 is an image depicting a representative sample of the 900 images taken of the immunofluorescent staining for insulin from the histological evaluation of control versus HIP-treated mice pancreata.
Figure 11:
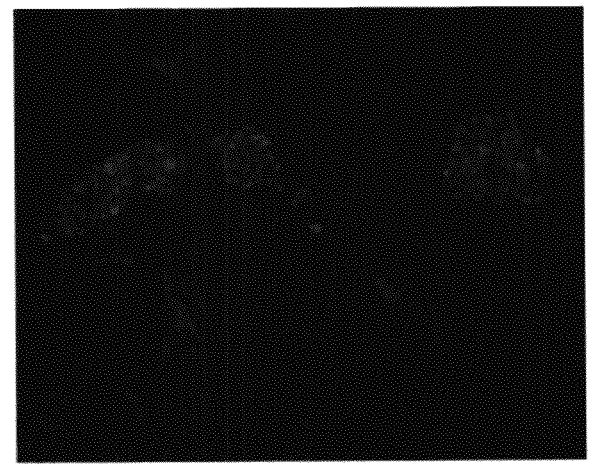

FIG. 11 demonstrates a representative sample of the 900 images taken of the immunofluorescent staining for insulin from the histological evaluation of control versus HIP-treated mice pancreata. Islet size was not different between HIP treated and control group, whereas, islet number and mass was increased.

What is claimed is:

1. A method of stimulating islet cell neogenesis in a subject in need thereof, comprising administering to said subject a therapeutically effective amount of a peptide consisting of the amino acid sequence of SEQ ID NO. 4, Human proIslet Peptide 2 (HIP2).

2. The method of claim 1, further comprising administering a therapeutically effective amount of an agent selected from the group consisting of: an immune therapy agent and an additional agent that stimulates islet cell regeneration.

3. The method of claim 2, wherein said immune therapy agent is selected from the group consisting of: anti-CD3 antibodies, sirolimus, tacrolimus, a heat-shock protein 60, an anti-glutamic acid decarboxylase 65 antibody, mycophenolate mofetil alone or in combination with daclizumab, an anti-CD20 agent, rituximab, campath-1H, lysofylline, vitamin D, IBC-VSO vaccine, interferon-alpha, and a vaccine using CD4+CD25+ antigen-specific regulatory T cells.

4. The method of claim 2, wherein said additional agent that stimulates islet cell regeneration is selected from the group consisting of: a Human ProIslet Peptide (HIP) or a HIP-related peptide, amylin, pramlintide, insulin, exendin-4, GIP, GLP-1, GLP-1 receptor agonists, GLP-1 analogs, hamster INGAP peptide and related peptides, liraglutide, and a dipeptidyl peptidase inhibitor which blocks the degradation of GLP-1.

5. A method of treating a disease or condition associated with impaired pancreatic function in a subject in need thereof, comprising administering to said subject a therapeutically effective amount of a peptide consisting of the amino acid sequence of SEQ ID NO. 4, Human proIslet Peptide 2 (HIP2).

6. The method of claim 5 wherein said disease or condition associated with impaired pancreatic function is selected from the group consisting of: type 1 diabetes, new onset type 1 diabetes, type 2 diabetes, Latent Autoimmune Diabetes in Adults, pre-diabetes, impaired fasting glucose, fasting hyperinsulinemia, impaired glucose tolerance, insulin resistant syndrome, insulin deficiency, metabolic syndrome, obesity, anorexia, bulimia, neuropathic pain, pancreatitis, pancreatic cancer, hyperlipidemia, hypertriglyceridemia, eating disorders, anovulatory cycles, lack of or diminished insulin production resulting in aberrant glucose metabolism, and polycystic ovarian syndrome.

7. The method of claim 6, wherein said disease or condition associated with impaired pancreatic function is selected from the group consisting of: type 1 diabetes, type 2 diabetes, Latent Autoimmune Diabetes in Adults, pre-diabetes, and metabolic syndrome.

8. The method of claim 5, further comprising administering a therapeutically effective amount of an agent selected from the group consisting of: an immune therapy agent and an additional agent that stimulates islet cell regeneration.

9. The method of claim 8, wherein said immune therapy is selected from the group consisting of: anti-CD3 antibodies, sirolimus, tacrolimus, a heat-shock protein 60, an anti-glutamic acid decarboxylase 65 antibody, mycophenolate mofetil alone or in combination with daclizumab, an anti-CD20 agent, rituximab, campath-1H, lysofylline, vitamin D, IBC-VSO vaccine, interferon-alpha, and a vaccine using $CD4^+CD25^+$ antigen-specific regulatory T cells.

10. The method of claim 8, wherein said additional agent that stimulates islet cell regeneration is selected from the group consisting of: a Human ProIslet Peptide (HIP) or a HIP-related peptide, amylin, pramlintide, insulin, exendin-4, GIP, GLP-1, GLP-1 receptor agonists, GLP-1 analogs, hamster INGAP peptide and related peptides, liraglutide, and a dipeptidyl peptidase inhibitor which blocks the degradation of GLP-1.

11. The method of claim 8, wherein said disease or condition associated with impaired pancreatic function is selected from the group consisting of: type 1 diabetes, new onset type 1 diabetes, type 2 diabetes, Latent Autoimmune Diabetes in Adults, pre-diabetes, impaired fasting glucose, fasting hyperinsulinemia, impaired glucose tolerance, insulin resistant syndrome, insulin deficiency, metabolic syndrome, obesity, anorexia, bulimia, neuropathic pain, pancreatitis, pancreatic cancer, hyperlipidemia, hypertriglyceridemia, eating disorders, anovulatory cycles, lack of or diminished insulin production resulting in aberrant glucose metabolism, and polycystic ovarian syndrome.

12. The method of claim 11, wherein said disease or condition associated with impaired pancreatic function is selected from: type 1 diabetes, type 2 diabetes, Latent Autoimmune Diabetes in Adults, pre-diabetes, and metabolic syndrome.

13. A method of reducing insulin requirements in a subject in need thereof, comprising administering to said subject a therapeutically effective amount of a peptide consisting of the amino acid sequence of SEQ ID NO. 4, Human proIslet Peptide 2 (HIP2).

14. The method of claim 13, further comprising administering a therapeutically effective amount of an agent selected from the group consisting of: an immune therapy agent and an additional agent that stimulates islet cell regeneration.

15. The method of claim 14, wherein said immune therapy is selected from the group consisting of: anti-CD3 antibodies, sirolimus, tacrolimus, a heat-shock protein 60, an anti-glutamic acid decarboxylase 65 antibody, mycophenolate mofetil alone or in combination with daclizumab, an anti-CD20 agent, rituximab, campath-1H, lysofylline, vitamin D, IBC-VSO vaccine, interferon-alpha, and a vaccine using $CD4^+CD25^+$ antigen-specific regulatory T cells.

16. The method of claim 14, wherein said additional agent that stimulates islet cell regeneration is selected from: a Human ProIslet Peptide (HIP) or a HIP-related peptide, amylin, pramlintide, insulin, exendin-4, GIP, GLP-1, GLP-1 receptor agonists, GLP-1 analogs, hamster INGAP peptide and related peptides, liraglutide, and a dipeptidyl peptidase inhibitor which blocks the degradation of GLP-1.

* * * * *

SEQUENCE LISTING

```
<160> NUMBER OF SEQ ID NOS: 7

<210> SEQ ID NO 1
<211> LENGTH: 15
<212> TYPE: PRT
<213> ORGANISM: Artificial
<220> FEATURE:
<223> OTHER INFORMATION: Fragment of naturally occurring hamster INGAP
      protein

<400> SEQUENCE: 1

Ile Gly Leu His Asp Pro Ser His Gly Thr Leu Pro Asn Gly Ser
1               5                   10                  15

<210> SEQ ID NO 2
<211> LENGTH: 15
<212> TYPE: PRT
<213> ORGANISM: Artificial
<220> FEATURE:
<223> OTHER INFORMATION: Fragment of naturally occurring human REG3
      protein

<400> SEQUENCE: 2
```

```
Ile Gly Leu His Asp Pro Thr Gln Gly Thr Glu Pro Asn Gly Glu
1               5                   10                  15
```

<210> SEQ ID NO 3
<211> LENGTH: 15
<212> TYPE: PRT
<213> ORGANISM: Artificial
<220> FEATURE:
<223> OTHER INFORMATION: Fragment of naturally occurring human REG3
      protein

<400> SEQUENCE: 3

```
Trp Ile Gly Leu His Asp Pro Thr Gln Gly Thr Glu Pro Asn Gly
1               5                   10                  15
```

<210> SEQ ID NO 4
<211> LENGTH: 14
<212> TYPE: PRT
<213> ORGANISM: Artificial
<220> FEATURE:
<223> OTHER INFORMATION: Fragment of naturally occurring human REG3
      protein

<400> SEQUENCE: 4

```
Ile Gly Leu His Asp Pro Thr Gln Gly Thr Glu Pro Asn Gly
1               5                   10
```

<210> SEQ ID NO 5
<211> LENGTH: 15
<212> TYPE: PRT
<213> ORGANISM: Artificial
<220> FEATURE:
<223> OTHER INFORMATION: Scrambled peptide sequence control

<400> SEQUENCE: 5

```
Asp Gly Gly Thr Pro Gln Pro Gly Asn Trp Ile Glu Leu Thr His
1               5                   10                  15
```

<210> SEQ ID NO 6
<211> LENGTH: 175
<212> TYPE: PRT
<213> ORGANISM: Artificial
<220> FEATURE:
<223> OTHER INFORMATION: Fragment of naturally occurring human REG3
      protein

<400> SEQUENCE: 6

```
Met Leu Pro Pro Met Ala Leu Pro Ser Val Ser Trp Met Leu Leu Ser
1               5                   10                  15

Cys Leu Met Leu Leu Ser Gln Val Gln Gly Glu Pro Gln Arg Glu
                20                  25                  30

Leu Pro Ser Ala Arg Ile Arg Cys Pro Lys Gly Ser Lys Ala Tyr Gly
            35                  40                  45

Ser His Cys Tyr Ala Leu Phe Leu Ser Pro Lys Ser Trp Thr Asp Ala
        50                  55                  60

Asp Leu Ala Cys Gln Lys Arg Pro Ser Gly Asn Leu Val Ser Val Leu
65                  70                  75                  80

Ser Gly Ala Glu Gly Ser Phe Val Ser Ser Leu Val Lys Ser Ile Gly
                85                  90                  95

Asn Ser Tyr Ser Tyr Val Trp Ile Gly Leu His Asp Pro Thr Gln Gly
                100                 105                 110

Thr Glu Pro Asn Gly Glu Gly Trp Glu Trp Ser Ser Ser Asp Val Met
            115                 120                 125
```

```
Asn Tyr Phe Ala Trp Glu Arg Asn Pro Ser Thr Ile Ser Ser Pro Gly
        130                 135                 140

His Cys Ala Ser Leu Ser Arg Ser Thr Ala Phe Leu Arg Trp Lys Asp
145                 150                 155                 160

Tyr Asn Cys Asn Val Arg Leu Pro Tyr Val Cys Lys Phe Thr Asp
                165                 170                 175

<210> SEQ ID NO 7
<211> LENGTH: 173
<212> TYPE: PRT
<213> ORGANISM: Artificial
<220> FEATURE:
<223> OTHER INFORMATION: Fragment of naturally occurring hamster INGAP
      protein

<400> SEQUENCE: 7

Met Met Leu Pro Met Thr Leu Cys Arg Met Ser Trp Met Leu Leu Ser
1                 5                  10                  15

Cys Leu Met Phe Leu Ser Trp Val Glu Gly Glu Ser Gln Lys Lys
            20                  25                  30

Leu Pro Ser Ser Arg Ile Thr Cys Pro Gln Gly Ser Val Ala Tyr Gly
        35                  40                  45

Ser Tyr Cys Tyr Ser Leu Ile Leu Ile Pro Gln Thr Trp Ser Asn Ala
    50                  55                  60

Glu Leu Ser Cys Gln Met His Phe Ser Gly His Leu Ala Phe Leu Leu
65                  70                  75                  80

Ser Thr Gly Glu Ile Thr Phe Val Ser Ser Leu Val Lys Asn Ser Leu
                85                  90                  95

Thr Ala Tyr Gln Tyr Ile Trp Ile Gly Leu His Asp Pro Ser His Gly
            100                 105                 110

Thr Leu Pro Asn Gly Ser Gly Trp Lys Trp Ser Ser Ser Asn Val Leu
        115                 120                 125

Thr Phe Tyr Asn Trp Glu Arg Asn Pro Ser Ile Ala Ala Asp Arg Gly
    130                 135                 140

Tyr Cys Ala Val Leu Ser Gln Lys Ser Gly Phe Gln Lys Trp Arg Asp
145                 150                 155                 160

Phe Asn Cys Glu Asn Glu Leu Pro Tyr Ile Cys Lys Phe
                165                 170
```